(12) United States Patent
Moroney et al.

(10) Patent No.: US 10,982,226 B2
(45) Date of Patent: Apr. 20, 2021

(54) GREEN ALGA BICARBONATE TRANSPORTER AND USES THEREOF

(71) Applicant: BOARD OF SUPERVISORS OF LOUISIANA STATE UNIVERSITY AND AGRICULTURAL AND MECHANICAL COLLEGE, Baton Rouge, LA (US)

(72) Inventors: James V. Moroney, Baton Rouge, LA (US); Marylou C. Machingura, Richmond Hill, GA (US); Joanna N. Bajsa-Hirschel, Oxford, MS (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 0 days.

(21) Appl. No.: 16/311,956

(22) PCT Filed: Jun. 20, 2017

(86) PCT No.: PCT/US2017/038278
§ 371 (c)(1),
(2) Date: Dec. 20, 2018

(87) PCT Pub. No.: WO2017/223055
PCT Pub. Date: Dec. 28, 2017

(65) Prior Publication Data
US 2019/0177741 A1    Jun. 13, 2019

Related U.S. Application Data

(60) Provisional application No. 62/352,278, filed on Jun. 20, 2016.

(51) Int. Cl.
*C12N 15/82* (2006.01)
*C07K 14/405* (2006.01)
*C12N 15/11* (2006.01)

(52) U.S. Cl.
CPC ........ *C12N 15/8271* (2013.01); *C07K 14/405* (2013.01); *C12N 15/11* (2013.01); *Y02A 40/146* (2018.01)

(58) Field of Classification Search
CPC ............................ C07K 14/405; Y02A 40/146
See application file for complete search history.

(56) References Cited

U.S. PATENT DOCUMENTS

2013/0007916 A1    1/2013  Spalding
2015/0299676 A1*  10/2015  Walsh ................. C12N 9/1288
                                                                    800/306

FOREIGN PATENT DOCUMENTS

WO    2015103074 A1    7/2015
WO    2016014720 A2    1/2016
WO    2016087314 A2    6/2016

OTHER PUBLICATIONS

Merchant et al (The Chlamydomonas Genome Reveals the Evolution of Key Animal and Plant Functions. Science. 318:245-252, 2007) (Year: 2007).*
Machingura et al (Identification and characterization of a solute carrier, CIA8, involved in inorganic carbon acclimation in Chlamydomonas reinhardtii. Journal of Experimental Botany, vol. 68, No. 14 pp. 3879-3890, 2017) (Year: 2017).*
GeneCopoeia Expertise (ORF Clones, Expression-Ready ORF cDNA Clones _ Genecopoeia, 1999) (Year: 1999).*
Moses (Appendix. Gene Transfer Methods Applicable to Agricultural Organisms. National Academies Press (US); 1-25, 1987) (Year: 1987).*
International Search Report and Written Opinion for PCT/US2017/038278 dated Sep. 22, 2017.
JGI Genome Portal; Mar. 4, 2009; Internet documentation downloaded from <http://genome.jgi.doe.gov/Chlre4/Chlre4.home.html> on Sep. 8, 2017; BLAST comparison of SEQ ID No. 1; pp. 1-12.
Hanschen, E.R, et al., The Gonium Pectoral Genome Demonstrates Co-Option of Cell Cycle Regulation During the Evolution of Multicellularity; Nature Communications; Apr. 22, 2016; pp. 1-11.
Jungnick et al., The carbon concentrating mechanism in Chlamydomonas reinhardtii: finding the missing pieces, Photosynthesis Research, vol. 121, No. 2-3, p. 159-173.
Price et al, The cyanobacterial CCM as a source of genes for improving photosynthetic CO2 fixation in crop species, Journal of Experimental Botany, vol. 64, No. 3, 2013.
Machingura et al., Identification and characterization of a solute carrier, CIA8, involved in inorganic carbon acclimation in Chlamydomonas reinhardtii, Journal of Experimental Botany, vol. 68, No. 14, p. 3879-3890, 2017.
Supplementary European Search Report for application EP17816042 dated Mar. 19, 2020.

\* cited by examiner

*Primary Examiner* — Ashley K Buran
*Assistant Examiner* — Wayne Zhong
(74) *Attorney, Agent, or Firm* — Thomas|Horstemeyer LLP

(57) ABSTRACT

Provided herein are green alga Cia8 polypeptides and the polynucleotides that encode them. Also provided herein are transformed cells and transgenic plants that include one or more of the polynucleotides and/or polypeptides provided herein.

4 Claims, 18 Drawing Sheets
Specification includes a Sequence Listing.

FIG. 7A
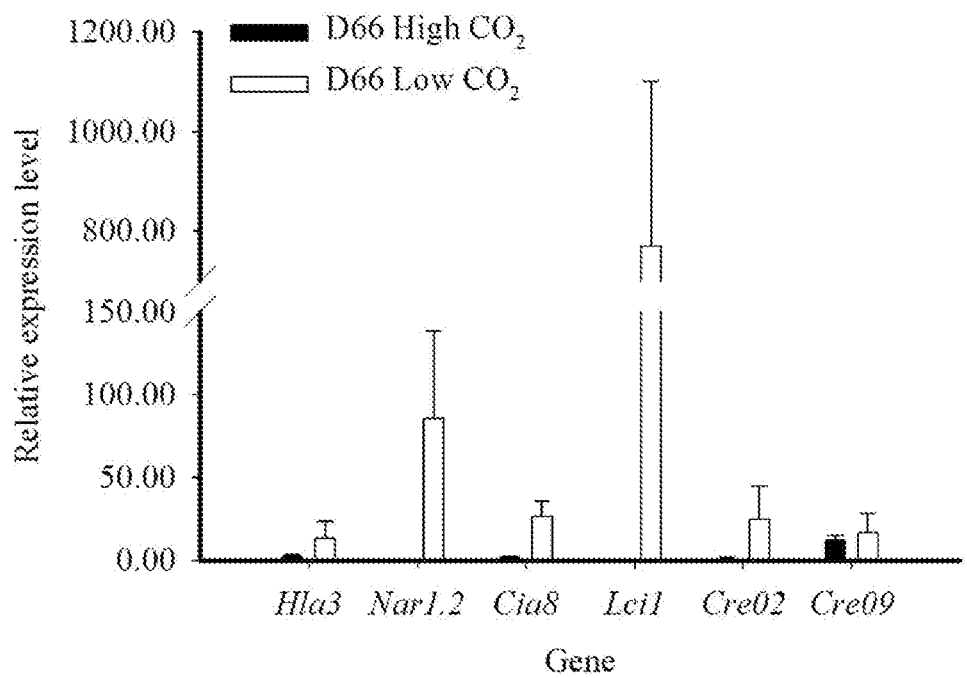
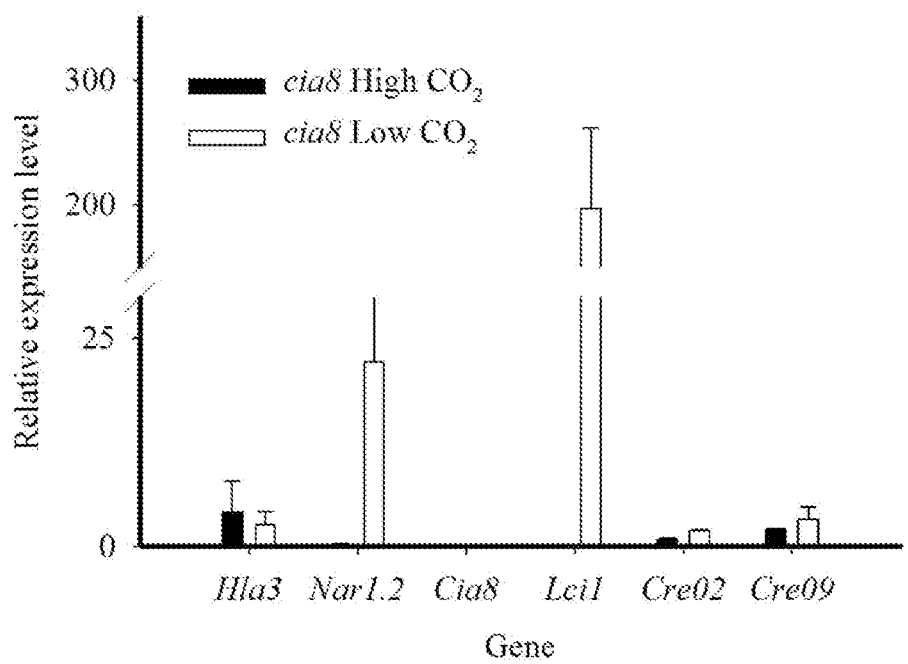
FIG. 7B

CLUSTAL OMEGA (1.2.1) Multiple Sequence Alignment

FIG. 9

CLUSTAL OMEGA (1.2.1) Multiple Sequence Alignment (cont.)

FIG. 9 (cont.)

CLUSTAL OMEGA (1.2.1) Multiple Sequence Alignment (cont.)

FIG. 9 (cont.)

SEQUENCE LISTING

```
<160> NUMBER OF SEQ ID NOS: 51

<210> SEQ ID NO 1
<211> LENGTH: 4846
<212> TYPE: DNA
<213> ORGANISM: Artificial Sequence
<220> FEATURE:
<223> OTHER INFORMATION: Cia8 Genomic DNA sequence, locus name:
      Cre09.g395700

<400> SEQUENCE: 1
gtatacatga tagcacgcct tgatatagcc caagaattgt gaaacgaaat tcggctttct         60
tgggcgcgta gggctacatt ggcaggcctt accttaaaaa aagatatatc actttcaccc       120
```

```
aacgatgtgc gccggcattc ggtcagcatc aacggcgggc ctgtcgacga cggcaatgca    180
gccgactcga gcgctcattc tatactcgca cctaaggacg gcgcctcgtt tcaatgtgct    240
tcaagagcct tgcttgcgga gttttgggtc ggtgtcggcg ttttggtcgc gccctagtca    300
tagtcggctc gtgggttgca acgccgcagc gggcgacgcc gcagcagcag gcgggcccgt    360
gcctctgccg ggcccgccac aggggccggc gccctccagc cctgcagcat ccacatcaga    420
ttctcaaaat cttaagcaca gtcatccgac gccagcagca cctgcaccag cagcctcatt    480
ggaacctgcc tccgcggcta gcggcgccgg cgtcagcacc agcaccagcg ccagcaccag    540
cgccgccagt accaacagca gcatagacag cagcgccacc acgaacggca gcagtggcgg    600
tggcgccgcg ccatcagctg tgtccacggt ggtgggctgg ctgcgcaagc tggtgacgga    660
gcagtacctg ccgctcatgc tgctggccgc gctggtggcg gcggcgctgc aggtaggtgg    720
ggacgcgcgg tcgctcggtg cgtgcgaggg aggggcaccg cgccacagcg ccccgccggc    780
gagagaaggg catgatactg cgtctggcgc gcgtgtacat cttcaatgcg aagggaaatg    840
ctaggtgatg ttagtttctc gatccgcccg cgttatcaca cggtactaac gtgtctgcgt    900
gtgttggctc cctcctccat tccgcagccg tcctggggtc tggcggcctc taagacgcag    960
ctgcagacgg cggtcacctt caccatcttc gtgctgcagg tgtgattgtc atggtgtggc    1020
tggtgagaag gttgtggacg tggtagtggt tggggcgatg atggtggtca tggtggtatt    1080
ggtggtgtga cgccgcggtc cttgtgtgcg tccggccctg aaccctggct ctagctctag    1140
tgcacctatg cacttccctg gcggaagctt tgtgttcatg tcggcacttg gtggtaagcg    1200
acccgaccac cgaaccgccg cacctgatgc cgccacctca aaacacacac acagggagtc    1260
atgctgcggc agggcgaggc gaagaaggcg cttggggcgg ccggtaagtg gccggcgggt    1320
gcgggcaggc gggggctgcc tactgctctt tgcaggtcct ggacagctgc aggccctgcc    1380
ggccatgtta ccctcgttac gcacgtgaca gcatcgcctc gctagttgca tggtcgtcaa    1440 gttttttttgc atcaccagta cacacacaca cacacacaca cacgtaccca acggcatgcc    1500
aacaccctgc accggctgtg tgtgtgtgtg ccgcgtgtgt gtgtgtgtgt gtgtgtgtgt    1560
gtgtgtgtgt gtgtcggcg tgcaggcgcc atcgcctggg gcatggcctc catcctcctc    1620
atcacgccac tgctggcgcc actggcgggg gcgctgccgc tgcagccgcc tggactggcg    1680
ctgggtgggt ggcggaggcg gtgcggtgcg ggcaggcgcg agctgcgtcg gggcgcctac    1740
atgcaagggc cgtggttgga acggcacca tagaaccaat gccagcatat gcatgcgcgc    1800
acattccatg ccgccgagtg tacttgatga cgcgttgcgc ggctccggac atttaagcac    1860
tggcatgcgg gcatcaaccc ccgcgcggcc cgccgtttgg cgccgccgct gttgcgaccc    1920
ctgccgccct tgcccctgcc gctcctgctg caggcctgct tgtgttcgga tgcatgccta    1980
ccaccctgtc cagcggcgtg gcgcttacac aggcgcgtga cacgtgtgtg tgtgtgtgtg    2040
tgactgtgtg tgtgtgcgct tacaacgcgt ctgcacagag tgccagtcac cagcgtgata    2100
ctgctgtgca cccaacgtcg ttgatgcgcg gggtccgcgt gtggggtgtg gccatacggt    2160
atggctgcgc agccatgccc ctcgtgccca cacgctgctg tgacaccaca gaacgcgcac    2220
accgacatac ccaacacacc ccacacacct tcccttgtg ctttcctcac tcacacacac    2280
gtacacacaa acgcacacac atttctgtcc tcccaggttc tgggcggcaa cacggccctg    2340
gcgctgctgc tgaccatcgc caccaacctg gcctccgtgt tcacactgcc cttcctgctg    2400
ccctgggcgc tcaaggtggg tgtagcgcgt ggggcatgag gcgctttgac tttggcaact    2460
ttgtgtgcgc ctcacgtggg ctgcacccgt gggggcagca ccccgctag ctaggtactg    2520
```

```
tagtagggc   gcggtaatgc   ggcaggggtc   ggcaccgtgc   cttcacactc   cggggaggag    2580
ggagagaatg   gattgggtgg   agtgcatggc   tggatggcag   cgacatatgc   tcaggtgcgt    2640
ggcgggtatt   gctcgccatc   accgccatca   aagccgattg   cacctccttc   ccttgcttgc    2700
ttgcgccccc   gcgggactgc   acccaaaact   gtaatgcaga   cgaccgcgtc   gatcggaggc    2760
tttggcgccg   ccgccgcggt   cgcgggcggc   tccgccgctg   ctgctgtgcg   gctggacccc    2820
gtgccgctgc   tggtgcagct   ggtgcagtgc   atcctgctgc   ccacactgct   gggcgccggc    2880
gtgcggggcg   ccagcgaggg   tgcgtgcggt   gtggtgtggt   ggggtggggt   ggggatggag    2940
ggatggaggg   cggcgtgttg   ctttgtgtgc   gcacacatgc   gcgtatggtg   gttttctccc    3000
agacggtgcc   cgaggtgtac   tgccggcgcg   tgtgcacatg   tacccacacg   cgcgccacag    3060
tgccacacgc   gcgctgaccc   cgccaccgg   ccttgctccc   tgctgtttgt   cacctgtcgc    3120
ctacgcctgt   cgcctcacat   gtcgtctcac   ctggcgcctc   acctccacac   atgacaggcc    3180
tgcgcagctg   ggtggatgcc   aaccggcgca   cactgagtgt   catcagcggc   ggcctgttgt    3240
cactggtgcc   ctggatgcag   gcgcgtgcgt   ggagggcggg   cgggcgcgag   cgcggtgccg    3300
ggttgccttg   gttgctggca   gttctggtat   tggattgccg   tgctgttgcc   aacttggggc    3360
agacgacgtg   gttccacacc   gcaagtccca   ccgcgcatgc   acgtctccac   cgtcatcctc    3420
actaaccacc   accaaccgct   ttgtacgtca   ccgtacggta   tgcatgtgtg   tgtgtacgaa    3480
ccgccgccgc   cgccgcaggt   cagcaaggcc   ctggctcagg   gcgtgacggt   ggcgccggcg    3540
gcgctggcgg   cggctgtggc   ctggtcgctg   gccttccatg   tcgtgtacct   ggggctcaac    3600
tgcggagccg   ccacggtggg   gcgcctgcct   gtgtgcctgt   gtgcctgagt   gacggcgcgg    3660
gcaggagtgg   cacgcagctg   gagtcacgcc   gccaacattc   gtgcacacac   acattgcgca    3720
tgcacacaat   gcacatacta   ttgaggtgcc   ggcggttgcc   atgagccggc   aatgcggcca    3780
aacccacaca   acggccctgg   cacgctcgca   tcacacacga   cacatgtcac   atgcaacacc    3840
ctcaacacgc   actcacgccg   tccctccaca   cgcacccacc   gtatgtgcac   acgtctgaat    3900
gacgcagctg   ttgaggttgg   gcggttctga   cccggtggcg   gcggcggcca   cgcggcgggc    3960
gctgatcatt   gtggcctcac   agaagactct   gcctgtggcc   atggcggtgc   gtggtggtgg    4020
ggtgggggtg   tcgtggaggt   gtgatgggaa   gttttgtgtg   ctacagtgta   cgtggtgggg    4080
aggcggtccg   gcataggcgg   gtgtaccctt   taggatgcgc   atattgtagt   gccagcgtgt    4140
agagatagtg   ccgcctttac   accaggttgc   ttggtgatcg   tgctgctgcg   ctcgtttgtg    4200
ctcactcacc   cactcccaca   cacgcgcgca   cgcacactcc   cggacacaggt   gctgggccgg    4260 ctggcgcctg   cggtgggcgc   cgaggcggcg   ggctgcgcgg   cggtgacggc   tgtgttcagt    4320
cacctggcgc   agacgtgtgt   ggacttcgca   ctggtgtcca   ggtgggaggg   aggagggggt    4380
agggtagttt   catgtgatcc   caagcaaccc   aagtcccaga   accagcccac   agttcttgtc    4440
gtcgttggcc   gttcatgggg   gggcgagcat   ggtggcagtc   gtaagggacg   atgggtgtgt    4500
gctttggtga   gaggcttgca   tcttttcggc   gatcgcatgc   tacttgatca   ctgagcaggt    4560
tgagcgcttg   atacgagccg   tgtgtcggac   ctgaccatgg   gacctggcca   ctactggctg    4620
gatgctgtga   tgtgtgcagg   tggctggagc   acattcagcg   gcgagacatc   aaagccaaca    4680
aggcggccta   gctggagcga   gggggcattt   gctgcaccta   gctggagtga   ggggcatat    4740 gctgcaccta   gctggagcga   ggcggcatat   gctgcagcag   caggaggcgc   tcgcatagct    4800
ggaggagggc   ctgtgcgtgg   gctcgggagg   cacgaaccta   tgaaag                    4846
```

<210> SEQ ID NO 2
<211> LENGTH: 1869
<212> TYPE: DNA
<213> ORGANISM: Artificial Sequence
<220> FEATURE:
<223> OTHER INFORMATION: Cia8 transcript sequence; Genbank Acession
      Number: Cre09.g395700.t1.1

<400> SEQUENCE: 2

| | | | | | |
|---|---|---|---|---|---|
| gtatacatga | tagcacgcct | tgatatagcc | caagaattgt | gaaacgaaat tcggctttct | 60 |
| tgggcgcgta | gggctacatt | ggcaggcctt | accttaaaaa | aagatatatc actttcaccc | 120 |
| aacgatgtgc | gccggcattc | ggtcagcatc | aacggcgggc | ctgtcgacga cggcaatgca | 180 |
| gccgactcga | gcgctcattc | tatactcgca | cctaaggacg | gcgcctcgtt tcaatgtgct | 240 |
| tcaagagcct | tgcttgcgga | gttttgggtc | ggtgtcggcg | ttttggtcgc gcccctagtca | 300 |
| tagtcggctc | gtgggttgca | acgccgcagc | gggcgacgcc | gcagcagcag gcgggcccgt | 360 |
| gcctctgccg | ggcccgccac | aggggccggc | gccctccagc | cctgcagcat ccacatcaga | 420 |
| ttctcaaaat | cttaagcaca | gtcatccgac | gccagcagca | cctgcaccag cagcctcatt | 480 |
| ggaacctgcc | tccgcggcta | gcggcgccgg | cgtcagcacc | agcaccagcg ccagcaccag | 540 |
| cgccgccagt | accaacagca | gcatagacag | cagcgccacc | acgaacggca gcagtggcgg | 600 |
| tggcgccgcg | ccatcagctg | tgtccacggt | ggtgggctgg | ctgcgcaagc tggtgacgga | 660 |
| gcagtacctg | ccgctcatgc | tgctggccgc | gctggtggcg | gcggcgctgc agccgtcctg | 720 |
| gggtctggcg | gcctctaaga | cgcagctgca | gacggcggtc | accttcacca tcttcgtgct | 780 |
| gcagggagtc | atgctgcggc | agggcgaggc | gaagaaggcg | cttggggcgg ccggcgccat | 840 |
| cgcctggggc | atggcctcca | tcctcctcat | cacgccactg | ctggcgccac tggcggggc | 900 |
| gctgccgctg | cagccgcctg | gactggcgct | gggcctgctt | gtgttcggat gcatgcctac | 960 |
| caccctgtcc | agcggcgtgg | cgcttacaca | ggttctgggc | ggcaacacgg ccctggcgct | 1020 |
| gctgctgacc | atcgccacca | acctggcctc | cgtgttcaca | ctgcccttcc tgctgccctg | 1080 |
| ggcgctcaag | acgaccgcgt | cgatcggagg | ctttggcgcc | gccgccgcgg tcgcgggcgg | 1140 |
| ctccgccgct | gctgctgtgc | ggctggaccc | cgtgccgctg | ctggtgcagc tggtgcagtg | 1200 |
| catcctgctg | cccacactgc | tgggcgccgg | cgtgcggggc | gccagcgagg gcctgcgcag | 1260 |
| ctgggtggat | gccaaccggc | gcacactgag | tgtcatcagc | ggcggcctgt tgtcactggt | 1320 |
| gccctggatg | caggtcagca | aggccctggc | tcagggcgtg | acggtggcgc cggcggcgct | 1380 |
| ggcggcgggct | gtggcctggt | cgctggcctt | ccatgtcgtg | tacctggggc tcaactgcgg | 1440 |
| agccgccacg | ctgttgaggt | tgggcggttc | tgacccggtg | gcggcggcgg ccacgcggcg | 1500 |
| ggcgctgatc | attgtggcct | cacagaagac | tctgcctgtg | gccatggcgg tgctgggccg | 1560 |
| gctggcgcct | gcggtgggcg | ccgaggcggc | gggctgcgcg | gcggtgacgg ctgtgttcag | 1620 |
| tcacctggcg | cagacgtgtg | tggacttcgc | actggtgtcc | aggtggctgg agcacattca | 1680 |
| gcggcgagac | atcaaagcca | acaaggcggc | ctagctggag | cgaggggca tttgctgcac | 1740 |
| ctagctggag | tgaggggca | tatgctgcac | ctagctggag | cgaggcggca tatgctgcag | 1800 |
| cagcaggagg | cgctcgcata | gctggaggag | ggcctgtgcg | tgggctcggg aggcacgaac | 1860 |
| ctatgaaag | | | | | 1869 |

<210> SEQ ID NO 3
<211> LENGTH: 1590
<212> TYPE: DNA

<213> ORGANISM: Artificial Sequence
<220> FEATURE:
<223> OTHER INFORMATION: Cia8 cDNA sequence; GenBank Acession Number:
    Cre09.g395700.t1.1 CDS

<400> SEQUENCE: 3

```
atgtgcgccg gcattcggtc agcatcaacg gcgggcctgt cgacgacggc aatgcagccg      60
actcgagcgc tcattctata ctcgcaccta aggacggcgc ctcgtttcaa tgtgcttcaa     120
gagccttgct tgcggagttt tgggtcgtgt cggcgttttt ggtcgcgccc tagtcatagt     180
cggctcgtgg gttgcaacgc cgcagcgggc gacgccgcag cagcaggcgg cccgtgcct      240
ctgccgggcc cgccacaggg gccggcgccc tccagccctg cagcatccac atcagattct     300
caaaatctta agcacagtca tccgacgcca gcagcacctg caccagcagc ctcattggaa     360
cctgcctccg cggctagcgg cgccggcgtc agcaccagca ccagcgccag caccagcgcc     420
gccagtacca acagcagcat agacagcagc gccaccacga acggcagcag tggcggtggc     480
gccgcgccat cagctgtgtc cacggtggtg ggctggctgc gcaagctggt gacggagcag     540
tacctgccgc tcatgctgct ggccgcgctg gtggcggcgg cgctgcagcc gtcctggggt     600
ctggcggcct ctaagacgca gctgcagacg gcggtcacct tcaccatctt cgtgctgcag     660
ggagtcatgc tgcggcaggg cgaggcgaag aaggcgcttg gggcggccgg cgccatcgcc     720
tggggcatgg cctccatcct cctcatcacg ccactgctgg cgccactggc ggggcgctg      780
ccgctgcagc cgcctggact ggcgctgggc ctgcttgtgt cggatgcat gcctaccacc      840
ctgtccagcg cgtggcgct acacaggtt ctgggcggca acacggccct ggcgctgctg       900
ctgaccatcg ccaccaacct ggcctccgtg ttcacactgc ccttcctgct gccctgggcg     960
ctcaagacga ccgcgtcgat cggaggcttt ggcgccgccg ccgcggtcgc gggcggctcc    1020
gccgctgctg ctgtgcggct ggaccccgtg ccgctgctgg tgcagctggt gcagtgcatc    1080
ctgctgccca cactgctggg cgccggcgtg cggggcgcca gcgagggcct gcgcagctgg    1140
gtggatgcca accggcgcac actgagtgtc atcagcggcg gcctgttgtc actggtgccc    1200
tggatgcagg tcagcaaggc cctggctcag ggcgtgacgg tggcgccggc ggcgctggcg    1260
gcggctgtgg cctggtcgct ggccttccat gtcgtgtacc tggggctcaa ctgcggagcc    1320
gccacgctgt tgaggttggg cggttctgac ccggtggcgg cggcggccac gcggcgggcg    1380
ctgatcattg tggcctcaca gaagactctg cctgtggcca tggcggtgct gggccggctg    1440
gcgcctgcgg tgggcgccga ggcggcgggc tgcgcggcgg tgacggctgt gttcagtcac    1500
ctggcgcaga cgtgtgtgga cttcgcactg gtgtccaggt ggctggagca cattcagcgg    1560
cgagacatca aagccaacaa ggcggcctag                                     1590
```

<210> SEQ ID NO 4
<211> LENGTH: 529
<212> TYPE: PRT
<213> ORGANISM: Artificial Sequence
<220> FEATURE:
<223> OTHER INFORMATION: Cia8 polypeptide sequence

<400> SEQUENCE: 4

```
Met Cys Ala Gly Ile Arg Ser Ala Ser Thr Ala Gly Leu Ser Thr Thr
1               5                   10                  15

Ala Met Gln Pro Thr Arg Ala Leu Ile Leu Tyr Ser His Leu Arg Thr
            20                  25                  30

Ala Pro Arg Phe Asn Val Leu Gln Glu Pro Cys Leu Arg Ser Phe Gly
        35                  40                  45
```

-continued

```
Ser Val Ser Ala Phe Trp Ser Arg Pro Ser His Ser Arg Leu Val Gly
     50                  55                  60

Cys Asn Ala Ala Ala Gly Asp Ala Ala Ala Gly Gly Pro Val Pro
 65                  70                  75                  80

Leu Pro Gly Pro Pro Gln Gly Pro Ala Pro Ser Ser Pro Ala Ala Ser
                     85                  90                  95

Thr Ser Asp Ser Gln Asn Leu Lys His Ser His Pro Thr Pro Ala Ala
                 100                 105                 110

Pro Ala Pro Ala Ala Ser Leu Glu Pro Ala Ser Ala Ala Ser Gly Ala
             115                 120                 125

Gly Val Ser Thr Ser Thr Ser Ala Ser Thr Ser Ala Ala Ser Thr Asn
             130                 135                 140

Ser Ser Ile Asp Ser Ser Ala Thr Thr Asn Gly Ser Ser Gly Gly Gly
145                 150                 155                 160

Ala Ala Pro Ser Ala Val Ser Thr Val Val Gly Trp Leu Arg Lys Leu
                 165                 170                 175

Val Thr Glu Gln Tyr Leu Pro Leu Met Leu Leu Ala Ala Leu Val Ala
             180                 185                 190

Ala Ala Leu Gln Pro Ser Trp Gly Leu Ala Ala Ser Lys Thr Gln Leu
             195                 200                 205

Gln Thr Ala Val Thr Phe Thr Ile Phe Val Leu Gln Gly Val Met Leu
210                 215                 220

Arg Gln Gly Glu Ala Lys Lys Ala Leu Gly Ala Ala Gly Ala Ile Ala
225                 230                 235                 240

Trp Gly Met Ala Ser Ile Leu Leu Ile Thr Pro Leu Leu Ala Pro Leu
                 245                 250                 255

Ala Gly Ala Leu Pro Leu Gln Pro Pro Gly Leu Ala Leu Gly Leu Leu
             260                 265                 270

Val Phe Gly Cys Met Pro Thr Thr Leu Ser Ser Gly Val Ala Leu Thr
             275                 280                 285

Gln Val Leu Gly Gly Asn Thr Ala Leu Ala Leu Leu Leu Thr Ile Ala
290                 295                 300

Thr Asn Leu Ala Ser Val Phe Thr Leu Pro Phe Leu Leu Pro Trp Ala
305                 310                 315                 320

Leu Lys Thr Thr Ala Ser Ile Gly Gly Phe Gly Ala Ala Ala Ala Val
                 325                 330                 335

Ala Gly Gly Ser Ala Ala Ala Ala Val Arg Leu Asp Pro Val Pro Leu
             340                 345                 350

Leu Val Gln Leu Val Gln Cys Ile Leu Leu Pro Thr Leu Leu Gly Ala
             355                 360                 365

Gly Val Arg Gly Ala Ser Glu Gly Leu Arg Ser Trp Val Asp Ala Asn
             370                 375                 380

Arg Arg Thr Leu Ser Val Ile Ser Gly Gly Leu Leu Ser Leu Val Pro
385                 390                 395                 400

Trp Met Gln Val Ser Lys Ala Leu Ala Gln Gly Val Thr Val Ala Pro
                 405                 410                 415

Ala Ala Leu Ala Ala Ala Val Ala Trp Ser Leu Ala Phe His Val Val
             420                 425                 430

Tyr Leu Gly Leu Asn Cys Gly Ala Ala Thr Leu Leu Arg Leu Gly Gly
             435                 440                 445

Ser Asp Pro Val Ala Ala Ala Thr Arg Arg Ala Leu Ile Ile Val
450                 455                 460
```

Ala Ser Gln Lys Thr Leu Pro Val Ala Met Ala Val Leu Gly Arg Leu
465                 470                 475                 480

Ala Pro Ala Val Gly Ala Glu Ala Ala Gly Cys Ala Ala Val Thr Ala
                485                 490                 495

Val Phe Ser His Leu Ala Gln Thr Cys Val Asp Phe Ala Leu Val Ser
            500                 505                 510

Arg Trp Leu Glu His Ile Gln Arg Arg Asp Ile Lys Ala Asn Lys Ala
        515                 520                 525

Ala

<210> SEQ ID NO 5
<211> LENGTH: 21
<212> TYPE: DNA
<213> ORGANISM: Artificial Sequence
<220> FEATURE:
<223> OTHER INFORMATION: primer CIA8-F (forward primer)

<400> SEQUENCE: 5
gcacatacta ttgaggtgcc g                                        21

<210> SEQ ID NO 6
<211> LENGTH: 19
<212> TYPE: DNA
<213> ORGANISM: Artificial Sequence
<220> FEATURE:
<223> OTHER INFORMATION: CIA8-R (reverse primer)

<400> SEQUENCE: 6
cggctgtgtt cagtcacct                                           19

<210> SEQ ID NO 7
<211> LENGTH: 20
<212> TYPE: DNA
<213> ORGANISM: Artificial Sequence
<220> FEATURE:
<223> OTHER INFORMATION: primer RIM3-1

<400> SEQUENCE: 7
cggtatcgga ggaaaagctg                                          20

<210> SEQ ID NO 8
<211> LENGTH: 26
<212> TYPE: DNA
<213> ORGANISM: Artificial Sequence
<220> FEATURE:
<223> OTHER INFORMATION: RIM3-2

<400> SEQUENCE: 8
taccggctgt tggacgagtt cttctg                                   26

<210> SEQ ID NO 9
<211> LENGTH: 23
<212> TYPE: DNA
<213> ORGANISM: Artificial Sequence
<220> FEATURE:
<223> OTHER INFORMATION: RX1

<400> SEQUENCE: 9
gccctcatag cccgccaaat cag                                      23

<210> SEQ ID NO 10
<211> LENGTH: 20
<212> TYPE: DNA
<213> ORGANISM: Artificial Sequence

```
<220> FEATURE:
<223> OTHER INFORMATION: RX2

<400> SEQUENCE: 10
aagccgataa acaccagccc                                              20

<210> SEQ ID NO 11
<211> LENGTH: 20
<212> TYPE: DNA
<213> ORGANISM: Artificial Sequence
<220> FEATURE:
<223> OTHER INFORMATION: primer CIA8CDSF2

<400> SEQUENCE: 11
cagtaccaac agcagcatag                                              20

<210> SEQ ID NO 12
<211> LENGTH: 17
<212> TYPE: DNA
<213> ORGANISM: Artificial Sequence
<220> FEATURE:
<223> OTHER INFORMATION: primer Cre09.g395700_CIA8-F2

<400> SEQUENCE: 12
atgtgcgccg gcattcg                                                 17

<210> SEQ ID NO 13
<211> LENGTH: 18
<212> TYPE: DNA
<213> ORGANISM: Artificial Sequence
<220> FEATURE:
<223> OTHER INFORMATION: primer Cre09.g395700_CIA8-R2

<400> SEQUENCE: 13
ctaggccgcc ttgttggc                                                18

<210> SEQ ID NO 14
<211> LENGTH: 20
<212> TYPE: DNA
<213> ORGANISM: Artificial Sequence
<220> FEATURE:
<223> OTHER INFORMATION: primer ACTIN F

<400> SEQUENCE: 14
gccagaagga ctcgtacgtt                                              20

<210> SEQ ID NO 15
<211> LENGTH: 20
<212> TYPE: DNA
<213> ORGANISM: Artificial Sequence
<220> FEATURE:
<223> OTHER INFORMATION: primer ACTIN R

<400> SEQUENCE: 15
cgccagagtc cagcacgata                                              20

<210> SEQ ID NO 16
<211> LENGTH: 22
<212> TYPE: DNA
<213> ORGANISM: Artificial Sequence
<220> FEATURE:
<223> OTHER INFORMATION: primer GAPDH F

<400> SEQUENCE: 16
atggcgccaa agaaggttct tc                                           22
```

<210> SEQ ID NO 17
<211> LENGTH: 22
<212> TYPE: DNA
<213> ORGANISM: Artificial Sequence
<220> FEATURE:
<223> OTHER INFORMATION: primer GAPDH R

<400> SEQUENCE: 17
ctacatcttg gccgccacga tc                                          22

<210> SEQ ID NO 18
<211> LENGTH: 31
<212> TYPE: DNA
<213> ORGANISM: Artificial Sequence
<220> FEATURE:
<223> OTHER INFORMATION: primer CIA8CDSEcoRIRnostop

<400> SEQUENCE: 18
gatcgaattc acggccgcct tgttggcttt g                                31

<210> SEQ ID NO 19
<211> LENGTH: 32
<212> TYPE: DNA
<213> ORGANISM: Artificial Sequence
<220> FEATURE:
<223> OTHER INFORMATION: primer CIA8CDSNdeIF

<400> SEQUENCE: 19
catgaccata tgatgtgcgc cggcattcgg tc                               32

<210> SEQ ID NO 20
<211> LENGTH: 16
<212> TYPE: DNA
<213> ORGANISM: Artificial Sequence
<220> FEATURE:
<223> OTHER INFORMATION: primer ShortGFP-F

<400> SEQUENCE: 20
ccaagggcga ggagct                                                 16

<210> SEQ ID NO 21
<211> LENGTH: 19
<212> TYPE: DNA
<213> ORGANISM: Artificial Sequence
<220> FEATURE:
<223> OTHER INFORMATION: primer CrGFP-R

<400> SEQUENCE: 21
cttgtacagc tcgtccatg                                              19

<210> SEQ ID NO 22
<211> LENGTH: 29
<212> TYPE: DNA
<213> ORGANISM: Artificial Sequence
<220> FEATURE:
<223> OTHER INFORMATION: primer CIA8transcr_R_BamHI

<400> SEQUENCE: 22
taggatccct ttcataggtt cgtgcctcc                                   29

<210> SEQ ID NO 23
<211> LENGTH: 29
<212> TYPE: DNA
<213> ORGANISM: Artificial Sequence
<220> FEATURE:
<223> OTHER INFORMATION: primer CIA8prom_F_SacI

```
<400> SEQUENCE: 23
cagagctcct caggcaaggt gatcaagtg                                     29

<210> SEQ ID NO 24
<211> LENGTH: 32
<212> TYPE: DNA
<213> ORGANISM: Artificial Sequence
<220> FEATURE:
<223> OTHER INFORMATION: primer CIA8prom_R_NotI

<400> SEQUENCE: 24
actagcggcc gcgtccgcat gttgcttatt tc                                 32

<210> SEQ ID NO 25
<211> LENGTH: 34
<212> TYPE: DNA
<213> ORGANISM: Artificial Sequence
<220> FEATURE:
<223> OTHER INFORMATION: primer CIA8transcr_F_NotI

<400> SEQUENCE: 25
actagcggcc gcgtatacat gatagcacgc cttg                               34

<210> SEQ ID NO 26
<211> LENGTH: 20
<212> TYPE: DNA
<213> ORGANISM: Artificial Sequence
<220> FEATURE:
<223> OTHER INFORMATION: primer HLA3_4,765F

<400> SEQUENCE: 26
gagcgttgtg tgcactgttc                                               20

<210> SEQ ID NO 27
<211> LENGTH: 20
<212> TYPE: DNA
<213> ORGANISM: Artificial Sequence
<220> FEATURE:
<223> OTHER INFORMATION: primer HLA3_4,884R

<400> SEQUENCE: 27
tctctctgcg gctacatcct                                               20

<210> SEQ ID NO 28
<211> LENGTH: 20
<212> TYPE: DNA
<213> ORGANISM: Artificial Sequence
<220> FEATURE:
<223> OTHER INFORMATION: Nar1.2_1,736F

<400> SEQUENCE: 28
agttgaggca ggttgagagc                                               20

<210> SEQ ID NO 29
<211> LENGTH: 20
<212> TYPE: DNA
<213> ORGANISM: Artificial Sequence
<220> FEATURE:
<223> OTHER INFORMATION: primer Nar1.2_1,855R

<400> SEQUENCE: 29
ccctgaccag ttgttgccat                                               20

<210> SEQ ID NO 30
```

<211> LENGTH: 20
<212> TYPE: DNA
<213> ORGANISM: Artificial Sequence
<220> FEATURE:
<223> OTHER INFORMATION: primer LCI1_1,125F

<400> SEQUENCE: 30
tggtttactg gccgcttctg                                                 20

<210> SEQ ID NO 31
<211> LENGTH: 20
<212> TYPE: DNA
<213> ORGANISM: Artificial Sequence
<220> FEATURE:
<223> OTHER INFORMATION: primer LCI1_1,244R

<400> SEQUENCE: 31
tcacacagcc aatcgaggtt                                                 20

<210> SEQ ID NO 32
<211> LENGTH: 20
<212> TYPE: DNA
<213> ORGANISM: Artificial Sequence
<220> FEATURE:
<223> OTHER INFORMATION: primer CIA8_1,745F

<400> SEQUENCE: 32
ctggagtgag ggggcatatg                                                 20

<210> SEQ ID NO 33
<211> LENGTH: 20
<212> TYPE: DNA
<213> ORGANISM: Artificial Sequence
<220> FEATURE:
<223> OTHER INFORMATION: CIA8_1,867R

<400> SEQUENCE: 33
ttcataggtt cgtgcctccc                                                 20

<210> SEQ ID NO 34
<211> LENGTH: 21
<212> TYPE: DNA
<213> ORGANISM: Artificial Sequence
<220> FEATURE:
<223> OTHER INFORMATION: primer SLC_cre09.g393250_1,874F

<400> SEQUENCE: 34
cgttactccc gtactcgtac c                                               21

<210> SEQ ID NO 35
<211> LENGTH: 20
<212> TYPE: DNA
<213> ORGANISM: Artificial Sequence
<220> FEATURE:
<223> OTHER INFORMATION: primer SLC_cre09.g393250_1,993R

<400> SEQUENCE: 35
gcccaccgaa ctacagagag                                                 20

<210> SEQ ID NO 36
<211> LENGTH: 20
<212> TYPE: DNA
<213> ORGANISM: Artificial Sequence
<220> FEATURE:
<223> OTHER INFORMATION: primer SLC_cre02.g147450_2,777F

<400> SEQUENCE: 36
ataggcggca gggaaaactc                                        20

<210> SEQ ID NO 37
<211> LENGTH: 20
<212> TYPE: DNA
<213> ORGANISM: Artificial Sequence
<220> FEATURE:
<223> OTHER INFORMATION: primer SLC_cre02.g147450_2,896R

<400> SEQUENCE: 37
tttgtggaat ccgcgtgaca                                        20

<210> SEQ ID NO 38
<211> LENGTH: 18
<212> TYPE: DNA
<213> ORGANISM: Artificial Sequence
<220> FEATURE:
<223> OTHER INFORMATION: primer CBLPF

<400> SEQUENCE: 38
cttctcgccc atgaccac                                          18

<210> SEQ ID NO 39
<211> LENGTH: 20
<212> TYPE: DNA
<213> ORGANISM: Artificial Sequence
<220> FEATURE:
<223> OTHER INFORMATION: primer CBLPR

<400> SEQUENCE: 39
cccaccaggt tgttcttcag                                        20

<210> SEQ ID NO 40
<211> LENGTH: 326
<212> TYPE: PRT
<213> ORGANISM: Ostreococcus lucimarinus

<400> SEQUENCE: 40

Phe Leu Leu Asp Asn Phe Leu Val Cys Gly Phe Cys Leu Ala Leu Leu
1               5                   10                  15

Phe Gly Leu Ser Val Pro Ala Ala Gly Lys Ala Leu Ala Lys Val Ser
            20                  25                  30

Val Ser Gly Trp Ser Val Ile Gln Thr Val Cys Val Val Ile Ile Phe
        35                  40                  45

Val Ile Ser Gly Ala Thr Leu Lys Thr Glu Glu Ile Thr Gln Ala Leu
    50                  55                  60

Lys Ala Gly Arg Gly Ala Leu Gly Tyr Gly Trp Val Ala Ile Leu Gly
65                  70                  75                  80

Leu Thr Pro Leu Leu Gly Phe Ile Leu Val Arg Val Pro Tyr Lys Pro
                85                  90                  95

Ile Glu Phe Arg Tyr Gly Leu Ala Leu Phe Cys Cys Val Pro Thr Thr
            100                 105                 110

Leu Thr Ser Gly Val Thr Leu Val Arg Asn Ala Lys Gly Asn Val Ala
        115                 120                 125

Leu Ala Leu Met Leu Thr Val Ser Thr Asn Leu Ile Gly Val Phe Thr
    130                 135                 140

Val Pro Phe Tyr Phe Asn Ala Val Val Ala Ser Gly Pro Arg Glu Met
145                 150                 155                 160

Ala Ser Ala Val Asn Gly Ala Ala Asn Asp Met Ser Thr Gln Ala Val
                165                 170                 175

Lys Leu Leu Val Lys Leu Leu Phe Thr Ile Leu Leu Pro Ile Val Leu
            180                 185                 190

Gly Lys Val Ala Arg Glu Met Ile Pro Ala Val Ala Ala Phe Ala Asn
        195                 200                 205

Ala Arg Lys Ala Glu Leu Thr Leu Thr Asn Asn Ser Cys Leu Ile Ile
210                 215                 220

Val Val Trp Met Ser Ile Ser Lys Ser Ala Lys Glu Leu Ile Asp Thr
225                 230                 235                 240

Asn Val Gly Thr Ile Phe Ala Val Leu Phe Ala Ala Val Leu Val His
                245                 250                 255

Val Val Phe Leu Ala Ile Asn Tyr Ala Ala Thr His Ala Leu Gly Leu
                260                 265                 270

Ser Gly Pro Glu Arg Val Ala Cys Val Met Met Ser Ser Gln Lys Thr
            275                 280                 285

Leu Pro Val Ala Met Thr Ile Ile Ser Tyr Leu Pro Glu Asp Val Phe
        290                 295                 300

Gly Ser Gly Gly Leu Ile Ala Ile Pro Cys Ile Val Cys His Ile Thr
305                 310                 315                 320

Gln Leu Phe Met Asp Ala
                325

<210> SEQ ID NO 41
<211> LENGTH: 407
<212> TYPE: PRT
<213> ORGANISM: Sorghum bicolor

<400> SEQUENCE: 41

Met Val Ser Tyr His Pro Ser Leu Ser Leu Leu Arg Pro Ser Val Leu
1               5                   10                  15

Thr Ala Arg Ala Ser Val Ile Gly Arg Cys Ser Thr Pro Asn Ala Phe
            20                  25                  30

Val Ser Ile Pro Val Val Ser Ala Ala Pro Leu Arg Leu Arg Pro Leu
        35                  40                  45

Leu Arg Ala Ala Ala Gly Gly Ala Ala Ser Pro Val Gly Gly Asn Gly
    50                  55                  60

Gly Lys Arg Ala Val Pro Pro Ser Ala Leu Leu Ile Asn Phe Ala Arg
65                  70                  75                  80

Ser Asn Phe Leu Pro Leu Ala Leu Ile Ser Gly Val Ile Leu Gly Leu
                85                  90                  95

Leu Asp Pro Thr Leu Gly Cys Leu Ala His Glu Tyr Ser Leu Ser Lys
            100                 105                 110

Phe Ser Thr Phe Gly Ile Phe Val Met Ser Gly Leu Thr Leu Arg Thr
        115                 120                 125

Lys Glu Leu Gly Thr Ala Leu Glu Ala Trp Pro Ala Ala Leu Tyr Gly
    130                 135                 140

Leu Gly Ser Ile Leu Leu Leu Thr Pro Phe Val Ser Gln Phe Ile Met
145                 150                 155                 160

Gln Val Gln Phe Phe Pro Arg Glu Phe Ile Thr Gly Leu Ala Ile Phe
                165                 170                 175

Cys Cys Met Pro Thr Thr Leu Ser Ser Gly Val Ile Leu Thr Gln Leu
            180                 185                 190

Val Gly Gly Asn Ser Ala Leu Ala Leu Ala Met Thr Val Ser Ser Asn
        195                 200                 205

Leu Leu Gly Ile Ile Ile Val Pro Leu Ser Leu Ala Arg Tyr Ile Gly

```
                210                 215                 220
Thr Gly Ala Gly Val Ser Leu Pro Thr Glu Lys Leu Phe Arg Ser Leu
225                 230                 235                 240

Val Thr Arg Leu Leu Ile Pro Leu Ile Ile Gly Lys Val Ala Arg Glu
                245                 250                 255

Ala Ser Lys Gly Ile Ala Asp Phe Val Asp Arg Asn Gln Gln Gly Phe
                260                 265                 270

Ser Val Gly Asn Ala Val Leu Leu Ser Leu Val Pro Trp Ile Gln Ile
                275                 280                 285

Ser Arg Ser Arg Ser Leu Ile Leu Ser Val Gln Val Glu Ala Phe Ala
                290                 295                 300

Ala Ala Ile Thr Val Gly Val Leu Ile His Leu Ala Leu Leu Ala Phe
305                 310                 315                 320

Asn Ile Ala Met Leu His Ile Leu Ser Arg Leu Gly Lys Lys Gly Asp
                325                 330                 335

Ser Val Phe Ala Lys Lys Glu Tyr Thr Arg Ala Val Ile Leu Val Ser
                340                 345                 350

Ser Gln Lys Thr Leu Pro Val Met Ile Thr Val Val Glu Gln Leu Gly
                355                 360                 365

Gly Ala Leu Gly Glu Ser Gly Leu Leu Val Ile Pro Cys Val Phe Ala
                370                 375                 380

His Ile Asn Gln Ile Ile Val Asp Ser Ile Ile Val Asn Trp Trp Arg
385                 390                 395                 400

Arg Arg Asp Gln Gln Asn Lys
                405

<210> SEQ ID NO 42
<211> LENGTH: 426
<212> TYPE: PRT
<213> ORGANISM: Picea sitchensis

<400> SEQUENCE: 42

Met Ile Met Met Ala Glu Gln Leu Arg Leu Leu Tyr Leu Val Gly Gly
1               5                   10                  15

Pro Pro Arg His Ser Leu Leu Leu Gln Arg Gly Gly His Val Thr Leu
                20                  25                  30

Pro Phe Glu Gln Arg Thr Gly Gly Arg Cys Tyr Leu Arg Leu Arg Pro
                35                  40                  45

Cys Ala Asn Ser Arg Ala Glu Ala His Gln Gly Ser His Gly Gly His
                50                  55                  60

Gln Lys Glu Asp Glu Asn His Cys Gln Pro Arg His Leu Thr Val Ala
65                  70                  75                  80

Lys Val Leu Asp Thr Val Lys Pro Val Leu Lys Phe Ala Arg Thr Asn
                85                  90                  95

Phe Leu Pro Leu Ala Leu Ile Thr Gly Val Thr Ile Gly Leu Val Asn
                100                 105                 110

Pro Val Pro Gly Cys Leu Ala Gln Lys Tyr Ser Leu Ser Asn Trp Ser
                115                 120                 125

Thr Phe Gly Ile Phe Leu Val Ser Gly Leu Thr Leu Arg Ser Gly Glu
                130                 135                 140

Met Ser Ala Ala Ile Glu Ala Trp Pro Ala Gly Ala Phe Gly Leu Val
145                 150                 155                 160

Ser Ile Leu Leu Phe Thr Pro Phe Ile Ser Arg Leu Val Leu Gln Leu
                165                 170                 175
```

Lys Leu Ile Pro Gln Glu Phe Val Thr Gly Leu Ala Met Phe Cys Cys
            180                 185                 190

Met Pro Thr Thr Leu Ser Ser Gly Val Ala Leu Thr Gln Val Val Gly
        195                 200                 205

Gly Asn Ser Ala Leu Ala Leu Ser Leu Thr Val Ala Ser Asn Leu Leu
    210                 215                 220

Gly Ile Val Thr Val Pro Phe Met Leu Ser Lys Leu Val Ala Gln Gly
225                 230                 235                 240

Val Gly Val Ser Val Pro Ala Gly Glu Leu Leu Lys Ser Leu Thr Leu
                245                 250                 255

Met Ile Leu Val Pro Leu Leu Leu Gly Lys Gly Ile Arg Asn Ser Phe
            260                 265                 270

Asn Gly Val Ala Lys Phe Val Asp Glu Arg Arg Glu Leu Phe Ser Met
        275                 280                 285

Ile Asn Ser Ile Phe Leu Ser Leu Val Pro Trp Met Gln Val Ser Gly
    290                 295                 300

Ser Arg Ala Leu Leu Leu Thr Ile Ser Pro Met Asn Phe Ile Ser Ala
305                 310                 315                 320

Ile Ala Ile Gly Met Cys Leu His Phe Ile Phe Leu Ser Leu Asn Thr
                325                 330                 335

Val Ile Met His Ser Leu Ser Leu Ile Phe Gly Gly Lys Arg Ser Thr
            340                 345                 350

Phe Gly Lys Glu Asn Asn Ala Arg Ala Ile Ile Val Ala Ser Gln
        355                 360                 365

Lys Thr Leu Pro Val Met Val Ala Ile Val Gly Arg Leu Gly Gly Val
    370                 375                 380

Leu Gly Glu Ala Gly Leu Leu Val Ile Pro Cys Val Ala Ala His Ile
385                 390                 395                 400

Asn Gln Ile Ile Met Asp Ser Phe Leu Val Asn Ile Trp Leu Gln Gln
                405                 410                 415

Asp Lys Arg Ala Leu Gln Val Lys Glu Thr
            420                 425

<210> SEQ ID NO 43
<211> LENGTH: 419
<212> TYPE: PRT
<213> ORGANISM: Vitis vinifera

<400> SEQUENCE: 43

Met Ala Ala Ile Ile Gln Thr Leu Ile Leu Arg Pro Pro His Pro Lys
1               5                   10                  15

Thr Leu Pro His Pro Thr Pro Ile Thr Ser Asn Ala Ile Arg Phe Cys
            20                  25                  30

Ile Ser Thr His Lys Cys Ser Leu Leu Leu Arg Lys Pro His Ser Val
        35                  40                  45

Ser Lys Ser Phe Pro Ile Thr Ala Ala Gln His Ser Ala Gln Gly Asp
    50                  55                  60

Asp Ala Ser Gln Ala Ala Ser Ser Gly Lys Ala Leu Ile Trp Ala Lys
65                  70                  75                  80

Pro Leu Leu Ser Phe Val Ala Asp Asn Phe Leu Pro Leu Ala Leu Val
                85                  90                  95

Ser Gly Val Ala Leu Gly Leu Ala Asn Pro Thr Leu Gly Cys Leu Ala
            100                 105                 110

Asp Arg Tyr Ser Leu Ser Lys Val Ser Thr Phe Gly Ile Phe Ile Ile
        115                 120                 125

Ser Gly Leu Met Leu Arg Ser Gly Glu Ile Gly Ala Ala Ala Glu Ala
130                 135                 140

Trp Pro Val Gly Ile Phe Gly Leu Gly Ser Ile Leu Leu Phe Thr Pro
145                 150                 155                 160

Leu Phe Ser Arg Leu Ile Leu Gln Phe Gln Leu Gln Pro Gln Glu Phe
                165                 170                 175

Ile Thr Gly Leu Ala Ile Phe Ser Cys Met Pro Thr Thr Leu Ser Ser
                180                 185                 190

Gly Val Ala Leu Thr Gln Leu Ala Gly Gly Asn Ser Ala Leu Ala Leu
                195                 200                 205

Ala Met Thr Val Ile Ser Asn Leu Leu Gly Ile Leu Ile Val Pro Phe
210                 215                 220

Ser Ile Ser Lys Phe Ile Ala Asp Gly Val Gly Val Ser Val Pro Thr
225                 230                 235                 240

Lys Gln Leu Leu Arg Ser Leu Val Val Thr Leu Leu Ile Pro Leu Ile
                245                 250                 255

Leu Gly Lys Val Leu Arg Glu Ser Phe Lys Gly Val Ala Asp Phe Val
                260                 265                 270

Asp Lys Asn Arg Lys Leu Leu Ser Met Ile Ser Ala Ile Phe Leu Ser
                275                 280                 285

Leu Val Pro Trp Ile Gln Val Ser Arg Ser Arg Ser Leu Leu Leu Met
290                 295                 300

Val Lys Pro Ala Val Phe Leu Val Ala Ile Gly Met Gly Thr Val Leu
305                 310                 315                 320

His Leu Val Leu Leu Ala Phe Asn Ala Leu Ser Ile Gln Ser Leu Ser
                325                 330                 335

Ala Val Ser Gly Gly Ser Lys Ser Pro Phe Ala Lys Arg Gln Asn Thr
                340                 345                 350

Val Ala Phe Leu Leu Val Ala Ser Gln Lys Thr Leu Pro Val Met Val
                355                 360                 365

Ala Val Val Glu Gln Leu His Gly Thr Leu Gly Glu Ser Gly Leu Leu
                370                 375                 380

Val Leu Pro Cys Val Ala Ala His Leu Asn Gln Ile Ile Met Asp Ser
385                 390                 395                 400

Phe Leu Ile Asn Ile Trp Leu Gly Lys Asp Cys Thr Ser Asp Asn Ala
                405                 410                 415

Lys Val Ala

<210> SEQ ID NO 44
<211> LENGTH: 412
<212> TYPE: PRT
<213> ORGANISM: Citrus sinensis

<400> SEQUENCE: 44

Met Ala Val Thr Leu Gln Thr Leu Ile Leu Thr Pro Arg Pro Ser Lys
1               5                   10                  15

Met Leu Ser Ser Trp His Arg Asn Ser His Phe Arg Ala Ser Gly Ser
                20                  25                  30

Leu Arg Phe Ser Pro Phe Val Thr Phe Ser Pro Gly Arg Ser Ile Ser
                35                  40                  45

Arg Pro Ile Arg Ala Cys Arg Pro Ser Asp Gln Asp Phe Ala Ser Ser
        50                  55                  60

Lys Gly Leu Asn Trp Ala Lys Pro Leu Leu Lys Ile Ala Ala Asp Asn
65                  70                  75                  80

```
Phe Leu Pro Leu Ala Leu Ile Gly Gly Val Ala Phe Gly Phe Ala Asn
                85                  90                  95

Pro Ser Leu Gly Cys Leu Ala Asp Lys Tyr Gln Leu Ser Lys Phe Ser
            100                 105                 110

Thr Phe Ala Ile Phe Ile Val Ser Gly Leu Thr Leu Arg Ser Gly Glu
        115                 120                 125

Ile Gly Ala Ala Ala Glu Ala Trp Pro Val Gly Ile Phe Gly Leu Phe
    130                 135                 140

Ser Ile Leu Leu Phe Thr Pro Tyr Phe Ser Lys Leu Ile Leu Gln Val
145                 150                 155                 160

Gln Leu Gln Pro Gln Glu Phe Val Thr Gly Leu Ala Leu Phe Ser Cys
                165                 170                 175

Met Pro Thr Thr Leu Ser Ser Gly Val Ala Leu Thr His Leu Ala Gly
            180                 185                 190

Gly Asn Ser Ala Leu Ala Leu Ala Met Thr Ile Ile Ser Asn Leu Leu
        195                 200                 205

Gly Ile Met Ile Val Pro Phe Ser Ile Ser Lys Phe Ile Ala Ala Gly
    210                 215                 220

Val Gly Ile Ser Val Pro Thr Lys Gln Leu Phe Lys Ser Leu Val Leu
225                 230                 235                 240

Thr Leu Leu Ile Pro Leu Ile Leu Gly Lys Val Leu Arg Glu Ser Ile
                245                 250                 255

Thr Gly Leu Ser Glu Phe Val Asp Gln Asn Arg Lys Leu Phe Ser Lys
            260                 265                 270

Ile Ser Ala Ile Phe Leu Ser Leu Val Pro Trp Met Gln Val Ser Arg
        275                 280                 285

Ser Arg Ser Leu Leu Leu Met Val Lys Pro Gln Val Phe Leu Val Ala
    290                 295                 300

Ile Trp Met Gly Thr Leu Leu His Leu Ile Leu Leu Ala Phe Asn Ala
305                 310                 315                 320

Phe Ser Val Trp Ser Leu Ser Val Ile Ser Gly Asp Cys Gln Ser Val
                325                 330                 335

Phe Ala Lys Lys Glu Asn Thr Asn Ala Val Leu Val Ala Ser Gln
            340                 345                 350

Lys Thr Leu Pro Val Leu Val Ala Val Val Glu Gln Leu Gly Cys Ala
        355                 360                 365

Phe Gly Glu Ser Gly Leu Leu Val Leu Pro Cys Val Ala Ala His Leu
    370                 375                 380

Thr Gln Ile Ile Met Asp Ser Phe Leu Val Asn Phe Trp Leu Arg Arg
385                 390                 395                 400

Asp Lys Asp Leu Ser Ser Asn Asn Ala Lys Val Ala
                405                 410

<210> SEQ ID NO 45
<211> LENGTH: 364
<212> TYPE: PRT
<213> ORGANISM: Musa acuminata subsp. Malaccensis

<400> SEQUENCE: 45

Phe Asp Gln Val Gly Gly Ser Gly Asn Gln Ser Ser Glu Asp Ser Val
1               5                   10                  15

Ser Gln Lys Ala Ser Thr Trp Ala Glu Pro Leu Leu Asp Phe Val Ala
            20                  25                  30

Thr Asn Phe Leu Pro Leu Ala Leu Leu Ser Gly Ile Ala Leu Gly Leu
```

```
                    35                  40                  45

Val Asn Pro Thr Pro Gly Cys Leu Ala His Lys Leu Ser Leu Ser Arg
         50                  55                  60

Phe Ser Thr Cys Gly Ile Phe Phe Ile Ser Gly Ile Met Leu His Ser
         65                  70                  75                  80

Arg Glu Leu Gly Ala Val Glu Ala Trp Pro Ala Gly Leu Phe Gly
                         85                  90                  95

Leu Gly Ser Ile Leu Leu Ile Thr Pro Phe Phe Ser Arg Leu Val Leu
                        100                 105                 110

Gln Ile Gln Leu Thr Pro His Glu Leu Ile Thr Gly Leu Ala Ala Phe
                    115                 120                 125

Cys Cys Met Pro Thr Thr Leu Ser Ser Gly Val Ala Leu Thr Gln Leu
        130                 135                 140

Val Gly Gly Asn Ser Ala Leu Ala Leu Ala Met Thr Val Leu Ser Asn
        145                 150                 155                 160

Leu Leu Gly Ile Leu Ile Val Pro Phe Ser Leu Ser Lys Leu Ile Gly
                        165                 170                 175

Ala Gly Ala Gly Ile Ser Val Pro Thr Ala Gln Leu Phe Lys Ser Leu
                    180                 185                 190

Ile Met Met Leu Leu Val Pro Leu Val Ile Gly Lys Val Ile Arg Asp
                    195                 200                 205

Ser Ser Lys Ser Val Ala Glu Tyr Val Asp Arg Asn Arg Arg Ser Phe
        210                 215                 220

Ser Met Ile Ser Ala Ile Leu Leu Gly Leu Val Pro Trp Met Gln Val
        225                 230                 235                 240

Ser Arg Ser Arg Ser Leu Leu Thr Val Lys Pro Ala Ile Phe Ala
                        245                 250                 255

Ile Ala Val Gly Met Gly Ile Leu Leu His Phe Val Leu Leu Ala Phe
                    260                 265                 270

Asn Thr Ile Ala Val Arg Ser Leu Ser Val Val Ser Gly Gly Asp Gln
                    275                 280                 285

Ser Val Phe Ser Lys Lys Glu Asn Leu Arg Ala Val Ile Ile Val Ala
        290                 295                 300

Ser Gln Lys Thr Leu Pro Val Leu Val Ala Val Val Glu Gln Leu Gln
        305                 310                 315                 320

Gly Ala Leu Gly Glu Ala Gly Leu Leu Val Leu Pro Cys Val Ala Leu
                        325                 330                 335

His Ile Asn Gln Ile Ile Ile Asp Ser Phe Leu Val Asn Trp Trp Leu
                    340                 345                 350

Arg Arg Asp Gln Ile Ser Ala Lys Ser Lys Glu Val
                    355                 360

<210> SEQ ID NO 46
<211> LENGTH: 280
<212> TYPE: PRT
<213> ORGANISM: Nelumbo nucifera

<400> SEQUENCE: 46

Met Ala Gly Thr Leu Gln Thr Leu Ala Phe Arg Pro Val Val Gly
         1               5                  10                  15

Ile Thr Val Pro Arg Leu Arg Asn Pro Phe Leu Ser Val Ile His Ile
                         20                  25                  30

His Met His Gly Tyr Ser Val Thr Ser Ser Pro Asn Leu Leu Leu Arg
                     35                  40                  45
```

Arg Asn Phe Pro Ser Thr Ser Arg Thr Ile Arg Ala Ser Glu Arg Ser
 50                  55                  60

Asp Gln Val Asn Gly Asn Gly Asn Leu His Ala Arg Ile Pro Asp Ser
 65                  70                  75                  80

Val Leu Leu Leu Thr Trp Val Lys Pro Ile Leu Ser Phe Val Gly Ser
                 85                  90                  95

Asn Phe Leu Pro Leu Ala Leu Val Ser Ala Val Ser Val Gly Leu Ala
                100                 105                 110

Asn Pro Arg Leu Gly Cys Leu Ala His Lys Tyr Ser Leu Ser Lys Phe
            115                 120                 125

Ser Thr Phe Gly Ile Phe Phe Ile Ser Gly Leu Met Leu Arg Ser Gly
130                 135                 140

Asp Val Gly Ala Ala Val Gln Ala Trp Pro Ala Gly Ile Phe Gly Leu
145                 150                 155                 160

Gly Leu Ile Leu Leu Phe Thr Pro Phe Phe Ser Arg Leu Val Leu Gln
                165                 170                 175

Leu Lys Leu Val Pro Gln Glu Phe Val Thr Gly Leu Ala Ile Phe Ser
                180                 185                 190

Cys Met Pro Thr Thr Leu Ser Ser Gly Val Ala Leu Thr Gln Leu Val
            195                 200                 205

Gly Gly Asn Ser Pro Leu Ala Leu Ala Met Thr Val Ser Asn Leu
210                 215                 220

Leu Gly Ile Leu Ile Val Pro Phe Ser Ile Ser Lys Phe Ile Ala Asp
225                 230                 235                 240

Gly Val Gly Val Arg Ile Pro Thr Glu Gln Leu Leu Arg Ser Leu Ile
                245                 250                 255

Thr Thr Leu Leu Ile Pro Leu Ile Leu Gly Lys Val Phe Arg Asp Phe
                260                 265                 270

Phe Ser Lys Val Gly Glu Tyr Val
            275                 280

<210> SEQ ID NO 47
<211> LENGTH: 649
<212> TYPE: PRT
<213> ORGANISM: Volvox carteri f. nagariensis

<400> SEQUENCE: 47

Met Ser Cys Phe Asn Gln Leu Ala Leu Pro Pro Arg Cys Arg Ala Gly
1               5                   10                  15

Pro Ser Arg Cys Ala Ala Cys Val Thr His Gln Lys Thr Thr Thr Gln
            20                  25                  30

Tyr Ala Leu Ile Ile Cys Ile Gly Leu Pro His Arg Leu Thr Gln His
        35                  40                  45

Ala Ala Thr Trp Ser Phe Arg Ala Gly His Ala Leu Pro Thr Ala Pro
 50                 55                  60

Gly Ser Pro Ser Leu Arg Cys His Ser Gln Pro Arg Asn Leu Tyr Thr
 65                 70                  75                  80

Val Leu Arg Ser Asn His His Gln Gln Thr Ala Val Ser Thr Val Arg
                 85                  90                  95

Cys Thr Asp Met Asn Arg Met Pro Cys Ser Ile Ala Val Pro Ala Ala
            100                 105                 110

Pro Arg Gly Val Ala Gly Thr Leu His Ser Thr Ile Ser Ala Ser Gly
        115                 120                 125

Val Ala Lys Ser Ala Ser Asp Gly Tyr Pro Gly Asp Asn Ser Val Thr
130                 135                 140

-continued

Gly Asn Lys Ser Ile His Gly Ser Asn Tyr Ala Thr His His Thr
145                 150                 155                 160

Thr Glu Ser Ala Ala Ala Thr Ser Thr Ala Ala Ser Ala Val Thr
            165                 170                 175

Ser Ser His Pro Asn Ile Ala Ala Ala Val Asp Ala Ala Ser Ala
            180                 185                 190

Ser Tyr Gly Ser Asp Gly Ala Pro Ala Val Thr Ala Ala Pro Ala
            195                 200                 205

Ala Ala Val Thr Gly Pro Pro Ala Gly Ser Cys Thr Ala Thr Ser Thr
210                 215                 220

Thr Ser Leu Gln Thr Ser Ala Thr Thr Trp Ala Ser Leu Val Ser Trp
225                 230                 235                 240

Phe Arg Arg Leu Val Ala Glu Gln Tyr Leu Pro Met Met Leu Leu Thr
                245                 250                 255

Ala Leu Leu Ala Ala Ala Leu Gln Val Gly Ser Arg Gly Ser Ala Met
            260                 265                 270

Leu Tyr Gly Asn Ala Gly Leu Gln Ser Ala Val Thr Phe Ala Val Phe
            275                 280                 285

Val Leu Arg Gly Val Met Leu Arg Arg Gly Glu Ala Glu Lys Ala Leu
            290                 295                 300

Gly Ala Lys Gly Ala Ile Leu Trp Gly Leu Ala Ser Ile Leu Leu Val
305                 310                 315                 320

Thr Pro Val Ala Ala Pro Val Ala Gly Ala Leu Pro Leu Gln Pro Pro
                325                 330                 335

Gly Leu Ala Leu Gly Leu Leu Val Phe Ala Cys Met Pro Thr Thr Leu
            340                 345                 350

Ser Ser Gly Val Ala Leu Thr Gln Val Leu Gly Gly Asn Thr Ala Leu
            355                 360                 365

Ala Leu Leu Leu Thr Ile Ser Thr Asn Met Ala Ser Val Phe Thr Leu
            370                 375                 380

Pro Phe Val Leu Pro Trp Ala Met Lys Ala Ser Ala Ala Leu Gly Gly
385                 390                 395                 400

Phe Gly Ala Cys Ser Gly Gly Ala Gly Val Gly Ala Ser Gly Gly
                405                 410                 415

Leu Val Val Gln Leu Asp Pro Val Pro Leu Leu Leu Gln Leu Val Gln
            420                 425                 430

Cys Ile Leu Val Pro Ala Cys Ile Gly Ala Gly Val Arg Gly Val Leu
            435                 440                 445

Pro Gly Leu Arg Arg Trp Val Asp Ser Asn Arg Arg Thr Leu Ser Val
450                 455                 460

Val Ser Gly Ala Leu Leu Ser Leu Val Pro Trp Met Gln Val Ser Lys
465                 470                 475                 480

Ala Leu Ser Gln Gly Val Val Ala Pro Gly Ala Leu Ala Ala
            485                 490                 495

Val Ser Ser Ser Leu Val Leu His Ala Ala Tyr Leu Ala Leu Asn Ala
            500                 505                 510

Thr Ala Ala Gln Val Phe Gln Leu Gly Gly Ser Asp Pro Arg Val Ala
            515                 520                 525

Ala Pro Thr Arg Arg Ala Val Val Val Ala Ser Gln Lys Thr Leu
            530                 535                 540

Pro Val Ala Met Ala Val Leu Gly Arg Leu Gly Pro Val Val Gly Ala
545                 550                 555                 560

Glu Ala Ala Gly Cys Ala Ala Val Thr Ala Val Phe Ser His Leu Ala
                    565                 570                 575

Gln Thr Cys Val Asp Phe Trp Leu Val Ser Arg Trp Leu Asp Arg Ile
            580                 585                 590

Arg Arg Arg Glu Asn Gln Leu Ala Ala Thr Arg Gln Leu Gly Ser Ala
        595                 600                 605

Ala Thr Gly Leu Asp Gly Cys Ala Thr Gly Leu Asp Gly Ser Ser Cys
    610                 615                 620

Ser Gly Gly Val Arg Gly Val Asn Gly Asp Asp Gly Asp Gly Pro Ala
625                 630                 635                 640

Ala Phe Arg Leu Gln Pro Gly Ala Gly
                645

<210> SEQ ID NO 48
<211> LENGTH: 356
<212> TYPE: PRT
<213> ORGANISM: Volvox carteri

<400> SEQUENCE: 48

Met Leu Arg Arg Gly Glu Ala Glu Lys Ala Leu Gly Ala Lys Gly Ala
1               5                   10                  15

Ile Leu Trp Gly Leu Ala Ser Ile Leu Leu Val Thr Pro Val Ala Ala
                20                  25                  30

Pro Val Ala Gly Ala Leu Pro Leu Gln Pro Pro Gly Leu Ala Leu Gly
            35                  40                  45

Leu Leu Val Gly Ala Cys Met Pro Thr Thr Leu Ser Ser Gly Val Ala
    50                  55                  60

Leu Thr Gln Val Leu Gly Gly Asn Thr Ala Leu Ala Leu Leu Leu Thr
65                  70                  75                  80

Ile Ser Thr Asn Met Ala Ser Val Phe Thr Leu Pro Phe Val Leu Pro
                85                  90                  95

Trp Ala Met Lys Ala Ser Ala Ala Leu Gly Gly Phe Gly Ala Cys Ser
            100                 105                 110

Gly Gly Gly Ala Gly Val Gly Ala Ser Gly Gly Leu Val Val Gln Leu
        115                 120                 125

Asp Pro Val Pro Leu Leu Leu Gln Leu Val Gln Cys Ile Leu Val Pro
    130                 135                 140

Ala Cys Ile Gly Ala Gly Val Arg Gly Val Leu Pro Gly Leu Arg Arg
145                 150                 155                 160

Trp Val Asp Ser Asn Arg Arg Thr Leu Ser Val Val Ser Gly Ala Leu
                165                 170                 175

Leu Ser Leu Val Pro Trp Met Gln Val Ser Lys Ala Leu Ser Gln Gly
            180                 185                 190

Val Val Ala Pro Gly Ala Leu Ala Ala Val Ser Ser Ser Leu
        195                 200                 205

Val Leu His Ala Ala Tyr Leu Ala Leu Asn Ala Thr Ala Ala Gln Val
    210                 215                 220

Phe Gln Leu Gly Gly Ser Asp Pro Arg Val Ala Ala Pro Thr Arg Arg
225                 230                 235                 240

Ala Val Val Val Val Ala Ser Gln Lys Thr Leu Pro Val Ala Met Ala
                245                 250                 255

Val Leu Gly Arg Leu Gly Pro Val Val Gly Ala Glu Ala Ala Gly Cys
            260                 265                 270

Ala Ala Val Thr Ala Val Phe Ser His Leu Ala Gln Thr Cys Val Asp
        275                 280                 285

```
Phe Trp Leu Val Ser Arg Trp Leu Asp Arg Ile Arg Arg Glu Asn
    290                 295                 300

Gln Leu Ala Ala Thr Arg Gln Leu Gly Ser Ala Ala Thr Gly Leu Asp
305                 310                 315                 320

Gly Cys Ala Thr Gly Leu Asp Gly Ser Ser Cys Ser Gly Gly Val Arg
                325                 330                 335

Gly Val Asn Gly Asp Asp Gly Asp Gly Pro Ala Ala Phe Arg Leu Gln
                340                 345                 350

Pro Gly Ala Gly
            355

<210> SEQ ID NO 49
<211> LENGTH: 353
<212> TYPE: PRT
<213> ORGANISM: Coccomyxa subellipsoidea

<400> SEQUENCE: 49

Met Pro Asn Asp Asp Arg Ala Gln Thr Gly Leu Gln Lys Ala Leu Ser
1               5                   10                  15

Phe Ile Gln Ala Gln Phe Leu Pro Leu Ala Leu Leu Ala Ala Met Ile
                20                  25                  30

Val Gly Tyr Leu Phe Pro Gly Pro Gly Leu Arg Ala Ala Asp Ala Gly
            35                  40                  45

Leu Gln Ser Leu Thr Thr Thr Gly Ile Phe Ile Ser Gly Leu Gly
        50                  55                  60

Leu Arg Arg Gly Glu Ala Leu Arg Ala Leu Ser Ala Trp Gly Ala Ile
65                  70                  75                  80

Leu Tyr Gly Phe Ala Ser Ile Leu Phe Ile Thr Pro Leu Ala Ala Leu
                85                  90                  95

Ala Val Leu Arg Leu Pro Leu Gly Ser Pro Glu Leu Ala Phe Gly Leu
                100                 105                 110

Ala Val Phe Cys Cys Met Pro Thr Thr Leu Ser Ser Gly Val Ser Leu
                115                 120                 125

Thr Gln Ala Phe Gly Gly Asn Ala Ala Leu Ala Leu Leu Leu Thr Val
    130                 135                 140

Gly Thr Asn Leu Val Gly Ile Phe Thr Met Pro Phe Met Leu Cys Trp
145                 150                 155                 160

Leu Leu Gly Ala Gly Asn Ser Ala Val Ser Leu Thr Pro Gly Pro Leu
                165                 170                 175

Leu Arg Ser Leu Met Arg Thr Ile Leu Ala Pro Leu Leu Val Gly Ala
                180                 185                 190

Ala Ala Arg Ala Phe Val Pro Gly Val Ala Gly Gln Val Asp Lys Asn
                195                 200                 205

Lys Lys Ala Leu Ala Leu Leu Ser Ala Cys Leu Leu Ala Leu Val Pro
    210                 215                 220

Trp Met Gln Ile Ser Arg Ala Val Ser Ser Thr Val Asp Val Ser Leu
225                 230                 235                 240

Thr Ala Leu Ala Lys Val Val Ala Ala Gly Val Ala Val His Leu Val
                245                 250                 255

Tyr Leu Ala Phe Asn Ser Ala Ala Val Gln Leu Leu Arg Ile Gly Gly
                260                 265                 270

Pro Pro Gly Lys Glu Ser Ala Gly Glu Arg Arg Ala Leu Ile Leu Val
                275                 280                 285

Gly Ser Gln Lys Thr Leu Pro Ile Ala Val Thr Val Leu Gly Gln Leu
```

```
            290                 295                 300
Gly Ser Val Leu Pro Gly Pro Val Gly Ile Ala Val Val Pro Cys Val
305                 310                 315                 320

Val Ser His Leu Ser Gln Ile Leu Ile Asp Ser Phe Leu Val Ser His
                325                 330                 335

Trp Leu Arg Gln Asp Ala Asp Ser Gln Gln Glu Leu Lys Gly Arg Thr
                340                 345                 350

Ala

<210> SEQ ID NO 50
<211> LENGTH: 339
<212> TYPE: PRT
<213> ORGANISM: Monoraphidium neglectum

<400> SEQUENCE: 50

Met Pro Ala Ala Ala Phe Val Gln Ala Gln Phe Leu Pro Val Val
1               5                   10                  15

Leu Val Thr Ala Ile Cys Val Gly Cys Ser Phe Pro Gln Ala Gly Val
                20                  25                  30

Ala Val Ser Gln Leu Pro Asn Leu Thr Ala Phe Val Thr Thr Ala Met
            35                  40                  45

Phe Val Ile Ser Gly Leu Gln Leu Arg Gln Gly Glu Ala Leu Gln Ala
50                  55                  60

Leu Lys Ala Arg Gly Ala Val Ala Phe Gly Ile Ile Ser Ile Leu Leu
65                  70                  75                  80

Ile Thr Pro Leu Ile Ser Leu Ala Val Leu Arg Leu Pro Leu His Pro
                85                  90                  95

Pro Glu Leu Ala Ile Gly Leu Ala Val Phe Cys Cys Met Pro Thr Ala
            100                 105                 110

Leu Ser Ser Gly Val Thr Leu Thr Gln Gln Ile Gly Gly Asn Val Ala
        115                 120                 125

Leu Ala Leu Leu Leu Thr Val Ser Thr Asn Met Leu Gly Val Phe Thr
130                 135                 140

Met Pro Phe Thr Leu Pro Ala Leu Leu Gly Pro Ala Leu Ala Gly Ser
145                 150                 155                 160

Val Arg Leu Glu Pro Leu Pro Leu Leu Val Lys Leu Val Lys Thr Ile
                165                 170                 175

Leu Val Pro Ser Leu Val Gly Ala Ser Ile Arg Ala Phe Val Pro Gly
            180                 185                 190

Ala Ala Ala Phe Val Asp Ala Arg Lys Lys Tyr Leu Thr Tyr Ser Asn
        195                 200                 205

Ala Leu Leu Leu Ala Leu Val Pro Trp Thr Gln Ile Ser Lys Ala Val
210                 215                 220

Ala Gln Arg Val Pro Leu Glu Ala Gly Ser Leu Leu Val Ala Ala Ala
225                 230                 235                 240

Ala Gly Val Gly Val His Leu Ala Phe Leu Ala Leu Asn Ile Gly Ala
                245                 250                 255

Cys Arg Leu Leu Arg Leu Gly Gly Pro Asp Pro Ala Ala Ala Leu Ala
            260                 265                 270

Val Arg Arg Ala Val Ile Leu Val Gly Ser Val Lys Thr Leu Pro Val
        275                 280                 285

Ala Val Ser Val Leu Ala Ser Leu Gly Pro Ala Leu Gly Pro Met Ala
290                 295                 300

Gly Val Ala Val Val Pro Ala Met Ser Ala His Leu Ser Gln Ile Ile
```

```
                305                 310                 315                 320
Ile Asp Ser Met Leu Val Ala Arg Trp Gln Ala Gln Asp Arg Ala Ala
                    325                 330                 335

Lys Ala Ala

<210> SEQ ID NO 51
<211> LENGTH: 456
<212> TYPE: PRT
<213> ORGANISM: Monoraphidium neglectum

<400> SEQUENCE: 51

Met Ala Gly Arg His Thr Ala Ser Leu Val Thr Ala Ser Phe Pro Ala
1               5                   10                  15

Gly Gly Ala Gly Pro Ala Ala Ser Leu Leu Arg Gln Cys Gln Leu
            20                  25                  30

Ala Ala Ala Ala Ala Arg Ala Cys Ala Pro Ala Leu Ala Phe Leu
        35                  40                  45

Asp Gln His Phe Leu Pro Leu Cys Leu Thr Ser Gly Val Ala Ala Gly
    50                  55                  60

Cys Ala Phe Pro Ala Ala Gly Val Glu Ala Ala Lys Leu Asn Leu Ser
65                  70                  75                  80

Thr Ala Val Thr Phe Cys Met Phe Val Ile Ala Gly Val Gln Leu Arg
                85                  90                  95

Gln Glu Glu Ala Phe Lys Ala Leu Gln Ala Lys Gly Ala Leu Leu Tyr
            100                 105                 110

Gly Leu Val Ser Ile Leu Phe Ile Thr Pro Leu Ile Ser Leu Ala Val
        115                 120                 125

Leu Gln Leu Pro Leu Gln Pro Arg Glu Leu Val Leu Gly Leu Ala Ile
    130                 135                 140

Phe Cys Cys Met Pro Thr Ala Leu Ser Ala Gly Ile Thr Phe Thr Gln
145                 150                 155                 160

Ala Ala Gly Gly Asn Val Ala Val Ala Leu Leu Thr Val Thr Ser
                165                 170                 175

Asn Met Leu Gly Val Phe Thr Met Pro Phe Val Leu Pro Ala Met Leu
            180                 185                 190

Gly Gly Ser Leu Gly Gly Ala Arg Leu Glu Pro Gly Pro Leu Leu Val
        195                 200                 205

Arg Leu Ile Tyr Ser Val Leu Ile Pro Thr Ile Ile Gly Ala Ala Ile
    210                 215                 220

Arg Ser Ser Val Pro Gly Ala Ala Ala Leu Ala Asp Ser Lys Lys Arg
225                 230                 235                 240

Glu Leu Ala Arg Val Ser Ala Leu Leu Leu Gly Leu Val Pro Trp Thr
                245                 250                 255

Gln Val Ser Lys Thr Val Ala Ala Gly Val Val Leu Ala Pro Gly Pro
            260                 265                 270

Leu Ala Val Met Leu Val Ala Gly Val Ala Val His Leu Ser Tyr Leu
        275                 280                 285

Ala Leu Asn Thr Ala Ala Ala Leu Arg Leu Gly Glu Val Ala Gly Pro
    290                 295                 300

Lys Gly Ala Arg Asp Ile Arg Arg Ala Val Ile Leu Thr Ala Ser Val
305                 310                 315                 320

Lys Thr Leu Pro Val Ala Val Ala Val Phe Ala Ser Leu Ala Pro Val
                325                 330                 335

Leu Gly Gly Met Leu Gly Val Ala Leu Val Pro Ala Leu Met Ala His
```

-continued

```
            340                 345                 350
Leu Ser Gln Ile Leu Ile Asp Ser Ala Ile Val Ala Arg Trp Gln Ala
            355                 360                 365

Gln Ala Arg Ala Glu Ala Ala Ala Ala Ala Ala Ala Glu Ala Ala
        370                 375                 380

Ala Ala Ala Glu Ala Glu Ala Ala Val Val Ala Gly Ala Ala Glu Gln
385                 390                 395                 400

Arg Arg Leu Gln Val Glu Arg Asp Glu Val Ala Val Val Met Ala Ala
                405                 410                 415

Ala Ala Asp Ala Ser Gly Gly Arg Arg Arg Arg His Gln Pro Ala
            420                 425                 430

Gly Gly Asp Pro Gln Gly Gln Glu Ser Gln Ser Asp Ala Val Leu Ala
            435                 440                 445

Pro Ala Ala Ala Gly Ala Val Gln
    450                 455
```

GREEN ALGA BICARBONATE TRANSPORTER AND USES THEREOF

CROSS-REFERENCE TO RELATED APPLICATIONS

This application is the 35 U.S.C. § 371 national stage application of PCT Application No. PCT/US2017/038278, filed Jun. 20, 2017, where the PCT claims priority to, and the benefit of, U.S. provisional application entitled "GREEN ALGA BICARBONATE TRANSPORTER AND USES THEREOF" having Ser. No. 62/352,278, filed Jun. 20, 2016, both of which are herein incorporated by reference in their entireties.

SEQUENCE LISTING

This application contains a sequence listing filed in electronic form as an ASCII.txt file entitled 222220-2080_ST25.txt, created on Jun. 16, 2016. The content of the sequence listing is incorporated herein in its entirety

BACKGROUND

Green algae and other photosynthetic aquatic organisms are often exposed to low and fluctuating $CO_2$ conditions in the natural environment. $CO_2$ availability for these organisms can be restricted by, among other factors: slow diffusion of gases in water, slow interconversion of the two inorganic carbon forms ($CO_2$ and $HCO_3^-$) and pH changes. Consequently, almost all aquatic photosynthetic organisms have evolved a carbon dioxide concentrating mechanism (CCM) inducible under limiting $CO_2$ conditions, to effectively concentrate inorganic carbon (Ci) for fixation by Rubisco (Giordano et al., 2005). In a current CCM model for the green alga, Chlamydomonas reinhardtii (Jungnick et al., 2014; Wang and Spalding, 2014) it is thought that bicarbonate transporters on the plasma membrane and chloroplast envelope are key components of the CCM allowing the movement of Ci, particularly $HCO_3^-$ through the membranes. Other CCM components include carbonic anhydrase enzymes that interconvert $CO_2$ and $HCO_3^-$ (Mitra et al., 2005; Moroney et al., 2011). In C. reinhardtii a compartment called the pyrenoid is at the base of the chloroplast. The pyrenoid is where Rubisco is sequestered under limiting $CO_2$ conditions (Kuchitsu et al., 1988; Rawat et al., 1996; Borkhsenious et al., 1998). An extensive network of thylakoid tubules and mini-tubules is associated with the pyrenoid (Engel et al., 2015) presumably to provide a pathway for $HCO_3^-$ to enter into the pyrenoid. The carbonic anhydrase CAH3, is found in these tubules and it is hypothesized that CAH3 converts the $HCO_3^-$ within the lumen to $CO_2$ for fixation (Moroney and Ynalvez, 2007).

C. reinhardtii cells grown under high $CO_2$ conditions (5% v/v) exhibit a low affinity for Ci. When high $CO_2$ acclimated cells are exposed to low $CO_2$ conditions (0.03% v/v), induction of high affinity transporters has been reported. While $CO_2$ will readily diffuse across membranes in the cell (Gutknecht et al., 1977), numerous studies have since established the need for an active transport system to facilitate the movement of Ci (particularly $HCO_3^-$) to the point of fixation by Rubisco in low $CO_2$ cells (Moroney et al., 1987; Sültemeyer et al., 1988; Badger et al., 1994; Ohnishi et al., 2010). In addition, molecular and physiological studies have also confirmed the occurrence of multiple forms of Ci transporters on the plasma membrane and chloroplast envelope of cells (Amoroso et al., 1998; Duanmu et al., 2009; Atkinson et al., 2015; Gao et al., 2015; Yamano et al., 2015). In marine cyanobacteria, $HCO_3^-$ transport at the plasma membrane is often coupled to the high external $Na^+$ ion concentration. In freshwater environments where Chlamydomonas is found, transport is thought to be $H^+$-coupled since $Na^+$ is relatively low (Morth et al., 2011; Taylor et al., 2012). Consequently, genomic studies with C. reinhardtii and Volvox carteri have revealed presence of both $H^+$- and $Na^+$-coupled transporters at least for sulphate and phosphate (Pootakham et al., 2010). It is not yet clear whether these molecular components also occur for bicarbonate uptake.

To date, two high and one low affinity bicarbonate transport proteins in C. reinhardtii are characterized and known to be functional under tow $CO_2$ conditions. The first, a high light activated protein (HLA3) is an ATP-binding cassette (ABC)-type transporter of the Multi-Drug Resistance protein family localized to the plasma membrane (Im and Grossman, 2002). The Hla3 transcript is induced by both high light and low $CO_2$ conditions and is controlled by the CCM1 'master regulator' encoded by the Cia5 gene. Duanmu et al., (2009) showed in HLA3 RNAi knockdown mutants, a significant reduction in Ci affinity and Ci uptake, supporting the role of the protein in $HCO_3^-$ transport. The second, the transporter LCI1, is a relatively small protein with little homology to other transmembrane proteins in the databases. LCI1 is strongly upregulated on low $CO_2$ conditions and has been localized to the plasma membrane (Ohnishi et al., 2010). In the study with LCI1, the authors also confirmed increased Ci uptake by overexpressing LCI1 protein in the Lcr1 (Chlamydomonas strain lacking a MYB-transcription factor) background. Thus, HLA3 and LCI1 are thought to be Ci transporters located on the plasma membrane.

The third transporter, NAR1.2 (also known as LCIA), is a chloroplast envelope protein of the Formate/Nitrite transporter family. Although the NAR1.2 protein has lower affinity for bicarbonate as revealed in the $K_{(0.5)}$ value which falls in the mM range, increased $HCO_3^-$ uptake is observed in Xenopus laevis oocytes when NAR1.2 is expressed in those cells (Mariscal et al., 2006; Atkinson et al., 2015). NAR1.2 has so far been attributed to Ci uptake on the chloroplast envelope even though there has been no direct evidence to support this. While the NAR1.2 protein plays an important role in Ci uptake, it may also have a regulatory function. This follows from a recent study in which Hla3 transcript did not accumulate in the absence of NAR1.2 protein hence the authors suggest that these proteins cooperate in bicarbonate accumulation (Yamano et al., 2015). In another proposed bicarbonate route into the chloroplast, NAR1.2 seems to also associate with a soluble protein LCIB (Wang and Spalding, 2014).

Two soluble proteins (LCIB/LCIC) form a complex, and are thought to be involved in recapture of $CO_2$ leaking from the pyrenoid after observations that they would closely associate with the pyrenoid when cells are acclimated to low $CO_2$ (Yamano et al., 2010; Wang et al., 2011). Other putative transporters CCP1 and CCP2, now confirmed to be mitochondrial (Atkinson et al., 2015) are yet to be resolved. In light of all this, it is evident that the Ci transport system in Chlamydomonas remains to be clarified in order to have a better understanding of the CCM.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 1C shows a graph demonstrating growth of wild-type strain D66 and the cia8 mutant in liquid culture (MIN). Cultures were grown in Erlenmeyer flasks blowing in low CO2 (0.01-0.025%). Values are expressed as the mean±SE (n=4).

FIG. 2B shows an image of a representative gel demonstrating the confirmation of AphVIII insertion in exon 10 of the cia8 gene. First lane D66 is the control genomic DNA without the cassette and the other 3 are cia8 genomic DNA. Lane 2 represents the 3'end of insertion and lane 3 represents the 5'end of insertion. Lane 4 spans the whole insertion region including the genomic region flanking the cassette using a primer pair in the gene.

FIG. 5C shows a graph demonstrating results from low $CO_2$-grown cells assayed at pH 9.0. cells were grown at high $CO_2$ and transferred to low $CO_2$ for about 4 h. Each point represents the mean and standard error of three separate experiments.

FIG. 6G shows the results of a RT-PCR analysis of the Cia8 mutant strain transformed with the fused CIA8:CrGFP protein. Analysis was done using poly (A) RNA from low $CO_2$ grown cells as templates for Reverse Transcriptase PCR. The primers shown in Table 2 amplify the GFP transcript (710 bp) from cDNA.

FIGS. 7A-7C show graphs demonstrating the quantitative RT-PCR results for Ci transporter genes under high and low $CO_2$ conditions in the wildtype (FIG. 7A) and cia8 mutant (FIG. 7B) strains. Wildtype D66 cells were grown on high $CO_2$ for 48 hr then subjected to low $CO_2$ acclimation for 4 hr. Lack of the Cia8 gene causes down-regulation of other CCM transporters and two other genes in the SBF family (FIG. 7C). The cblp gene was used as the internal control. Relative expression level is expressed as $1000/2^{\Delta Ct}$ in which $\Delta Ct = Ct_{gene} - Ct_{cblp}$.

FIG. 8B shows a graph demonstrating the results of an RT-PCR analysis showing restoration of the Cia8 transcript in the complemented strains. GAPDH was used as the loading control. FIG. 8C shows a graph demonstrating oxygen evolution (FIG. 8C) for wildtype, D66, and one complemented line, com1, at pH 9.0. Each point represents the mean and standard error of three separate experiments. FIG. 8D shows a zoomed-in view of the lower end of the bicarbonate concentration (from 0 to 500 µM) of the data presented in FIG. 8C.

FIG. 9 shows Clustal Omega alignment of the CIA8 primary protein sequence with other SBF transporters from higher plants and other chlorophytes. List of species and their accession numbers in NCBI or Phytozome: Monoraphidium neglectum XP_013904301.1 (SEQ ID NO:50); Monoraphidium neglectum, XP_013896513.1 (SEQ ID NO:51), Coccomyxa subellipsoidea C-169] XP_005649764.1 (SEQ ID NO:49), Picea sitchensis, ABR16540.1 (SEQ ID NO:42), Musa acuminata subsp. Malaccensis, XP_009404829.1 (SEQ ID NO:45), Nelumbo nucifera, XP_010271688.1 (SEQ ID NO:46), Vitis vinifera, XP_002266805.1 (SEQ ID NO:43), Citrus sinensis, XP_006485208.1 (SEQ ID NO:44) Sorghum bicolor, XP_002440278.1 (SEQ ID NO:41), Volvox carteri f. nagariensis, XP_002955170.1 (SEQ ID NO:47) Volvox carteri, locus Name Vocar.0008s0179 (SEQ ID NO:48); Ostreococcus lucimarinus locus name gwEuk.2.273.1 (SEQ ID NO:40).

(FIG. 11B) $CO_2$ fixed and (FIG. 11A) $CO_2$ remaining in the pool. Statistical analysis was done by Tukey's HSD test. Different letters indicate that means are significantly different at P=0.01.

DETAILED DESCRIPTION

Figure 1A:
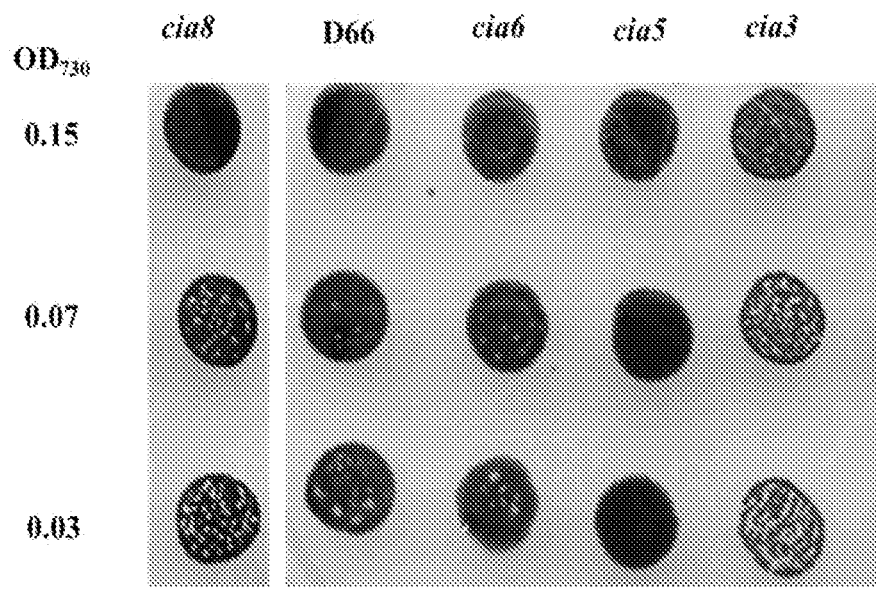
FIGS. 1A-1C show images demonstrating results from a spot test for the growth of C. reinhardtii strains in (FIG. 1A) high $CO_2$ (5% $CO_2$ in air) and (FIG. 1B) low $CO_2$ (0.01% $CO_2$ in air) pH 7.3. The strains include wild-type D66, Cia8 mutant and three known CCM mutants Cia6, Cia5 and Cia3 used as controls. The numbers to the left represent the initial $OD_{730}$ of 0.15 (~1.5×10⁶ cells) and two serial dilutions.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

In describing the disclosed subject matter, the following terminology will is used in accordance with the definitions set forth below.

As used herein, "about," "approximately," and the like, when used in connection with a numerical variable, generally refers to the value of the variable and to all values of the variable that are within the experimental error (e.g., within the 95% confidence interval for the mean) or within +−10% of the indicated value, whichever is greater.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "nucleic acid sequence" and "oligonucleotide" also encompasses a nucleic acid and polynucleotide as defined above.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "gene" refers to a hereditary unit corresponding to a sequence of DNA that occupies a specific location on a chromosome and that contains the genetic instruction for a characteristic(s) or trait(s) in an organism.

As used herein, "locus" refers to the position that a given gene or portion thereof occupies on a chromosome of a given species.

As used herein, "allele(s)" indicates any of one or more alternative forms of a gene, where the alleles relate to at least one trait or characteristic. In a diploid cell or organism, the two alleles of a given gene occupy corresponding loci on a pair of homologous chromosomes. The term "heterozygous" refers to a genetic condition where the organism or cell has different alleles at corresponding loci on homologous chromosomes.

As used herein, "homozygous" refers to a genetic condition where the organism or cell has identical alleles at corresponding loci on homologous chromosomes.

As used herein, the term "exogenous DNA" or "exogenous nucleic acid sequence" or "exogenous polynucleotide" refers to a nucleic acid sequence that was introduced into a cell, organism, or organelle via transfection. Exogenous nucleic acids originate from an external source, for instance, the exogenous nucleic acid may be from another cell or organism and/or it may be synthetic and/or recombinant. While an exogenous nucleic acid sometimes originates from a different organism or species, it may also originate from the same species (e.g., an extra copy or recombinant form of a nucleic acid that is introduced into a cell or organism in addition to or as a replacement for the naturally occurring nucleic acid). Typically, the introduced exogenous sequence is a recombinant sequence.

As used herein, the term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a "fusion protein" (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc.). Recombinant also refers to the polypeptide encoded by the recombinant nucleic acid. Non-naturally occurring nucleic acids or polypeptides include nucleic acids and polypeptides modified by man.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome.

As used herein, "transformation" or "transformed" refers to the introduction of a nucleic acid (e.g., DNA or RNA) into cells in such a way as to allow expression of the coding portions of the introduced nucleic acid.

As used herein a "transformed cell" is a cell transfected with a nucleic acid sequence.

As used herein, a "transgene" refers to an artificial gene which is used to transform a cell of an organism, such as a bacterium or a plant.

As used herein, "transgenic" refers to a cell, tissue, or organism that contains a transgene.

As used herein, "polypeptides" or "proteins" are as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein "peptide" refers to chains of at least 2 amino acids that are short, relative to a protein or polypeptide.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

As used herein, "functional variant" refers to a variant of a protein or polypeptide (e.g., a variant of a Cia8 protein) that can perform the same functions or activities as the original protein or polypeptide, although not necessarily at the same level (e.g., the variant may have enhanced, reduced or changed functionality, so long as it retains the basic function).

As used herein, "identity," can refer to a relationship between two or more polypeptide sequences or nucleotide, as determined by comparing the sequences. In the art, "identity" also refers to the degree of sequence relatedness between polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure.

As used herein, "tolerant" or "tolerance" refers to the ability of a plant to overcome, completely or to some degree, the detrimental effect of an environmental stress or other limiting factor.

As used herein, "expression" as used herein describes the process undergone by a structural gene to produce a polypeptide. It is a combination of transcription and translation. Expression refers to the "expression" of a nucleic acid to produce a RNA molecule, but it is refers to "expression" of a polypeptide, indicating that the polypeptide is being produced via expression of the corresponding nucleic acid.

As used herein, "over-expression" and "up-regulation" refers to the expression of a nucleic acid encoding a polypeptide (e.g., a gene) in a transformed plant cell at higher levels (therefore producing an increased amount of the polypeptide encoded by the gene) than the "wild type" plant cell (e.g., a substantially equivalent cell that is not transfected with the gene) under substantially similar conditions.

As used herein, "under-expression" and "down-regulation" refers to expression of a polynucleotide (e.g., a gene) at lower levels (producing a decreased amount of the polypeptide encoded by the polynucleotide) than in a wild type plant cell.

As used herein, "inhibit" or "inhibiting" expression of a gene indicates that something (e.g., antisense nucleotide, suppressor, antagonist, etc.) acts to reduce or prevent (completely or partially) the transcription, translation and/or other processing step in the expression of a gene, thereby downregulating the gene expression so that a reduced amount of the active protein encoded by the gene is produced as compared to wild type.

As used herein, "plasmid" as used herein can refer to a non-chromosomal double-stranded DNA sequence including an intact "replicon" such that the plasmid is replicated in a host cell.

As used herein, the term "vector" can be used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, "promoter" includes all sequences capable of driving transcription of a coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

As used herein, "operatively linked" can that the regulatory sequences useful for expression of the coding sequences of a nucleic acid are placed in the nucleic acid molecule in the appropriate positions relative to the coding sequence so as to effect expression of the coding sequence. This same definition is sometimes applied to the arrangement of coding sequences and transcription control elements (e.g. promoters, enhancers, and termination elements), and/or selectable markers, and/or other functional sequences in an expression vector, polynucleotide, or polypeptide.

As used herein, "selectable marker" refers to a gene whose expression allows one to identify cells that have been transformed or transfected with a vector containing the marker gene. For instance, a recombinant nucleic acid may include a selectable marker operatively linked to a gene of interest and a promoter, such that expression of the selectable marker indicates the successful transformation of the cell with the gene of interest.

As used herein, "constitutive promoter" is a promoter that allows for continual or ubiquitous transcription of its associated gene or polynucleotide. Constitutive promoters are generally are unregulated by cell or tissue type, time, or environment.

As used herein, "inducible promoter" is a promoter that allows transcription of its associated gene or polynucleotide in response to a substance or compound (e.g. an antibiotic, or metal), an environmental condition (e.g. temperature), developmental stage, or tissue type.

As used herein, "wild-type" can refer to the typical or average form of an organism, variety, strain, gene, protein, or characteristic as it occurs in nature or in a defined population, as distinguished from mutant forms that may result from natural or selective breeding or transformation with a transgene.

As used herein, "electroporation" is a transformation method in which a high concentration of plasmid DNA (containing exogenous DNA) is added to a suspension of host cell protoplasts, and the mixture shocked with an electrical field of about 200 to 600 V/cm.

As used herein, "isolated" means separated from constituents, cellular and otherwise, in which the polynucleotide, peptide, polypeptide, protein, antibody, or fragments thereof, are normally associated with in nature. In one aspect of this disclosure, an isolated polynucleotide is separated from the 3' and 5' contiguous nucleotides with which it is normally associated with in its native or natural environment, e.g., on the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated," "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the embodiments disclosed herein, it is to be understood that all of the above embodiments for each of the compositions disclosed below and under the appropriate conditions, are provided by this disclosure. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, "purified" is used in reference to a nucleic acid sequence, peptide, or polypeptide that has increased purity relative to the natural environment.

As used herein, "control" is an alternative subject or sample used in an experiment for comparison purposes and included to minimize or distinguish the effect of variables other than an independent variable. A "control" can be positive or negative.

As used herein, "concentrated" used in reference to an amount of a molecule, compound, or composition, including, but not limited to, a chemical compound, polynucleotide, peptide, polypeptide, protein, antibody, or fragments thereof, that indicates that the sample can be distinguishable from its naturally occurring counterpart in that the concentration or number of molecules per volume is greater than that of its naturally occurring counterpart and/or its efficacy and/or functionality per dose as compared to its naturally occurring counterpart in its native state.

As used herein, "diluted" used in reference to a an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "separated" refers to the state of being physically divided from the original source or population such that the separated compound, agent, particle, chemical compound, or molecule can no longer be considered part of the original source or population.

As used herein, "synthetic" refers to a compound that is made by a chemical or biological synthesis process that occurs outside of and independent from the natural organism from which the compound can naturally be found.

Discussion

Green algae and other photosynthetic aquatic organisms are often exposed to low and fluctuating $CO_2$ conditions in the natural environment. $CO_2$ availability for these organisms can be restricted by, among other factors: slow diffusion of gases in water, slow interconversion of the two inorganic carbon forms ($CO_2$ and $HCO_3^-$) and pH changes. Consequently, almost all aquatic photosynthetic organisms have evolved a carbon dioxide concentrating mechanism (CCM) inducible under limiting $CO_2$ conditions, to effectively concentrate inorganic carbon (Ci) for fixation by Rubisco (Giordano et al., 2005). To date, two high and one low affinity bicarbonate transport proteins in *C. reinhardtii* are characterized and known to be functional under low $CO_2$ conditions. HLA3 and LCI1 are thought to be Ci transporters located on the plasma membrane. The third transporter, NAR1.2 (also known as LCIA), is a chloroplast envelope protein of the Formate/Nitrite transporter family. NAR1.2 has so far been attributed to Ci uptake on the chloroplast envelope even though there has been no direct evidence to support this.

Further, two soluble proteins (LCIB/LCIC) form a complex, and are thought to be involved in recapture of $CO_2$ leaking from the pyrenoid after observations that they would closely associate with the pyrenoid when cells are acclimated to low $CO_2$ (Yamano et al., 2010; Wang et al., 2011). Other putative transporters CCP1 and CCP2, now confirmed to be mitochondrial (Atkinson et al., 2015) are yet to be resolved. In light of all this, it is evident that the Ci transport system in *Chlamydomonas* remains to be clarified in order to have a better understanding of the CCM.

With that said, described herein is a solute carrier protein from green alga that can be involved in bicarbonate transport, designated Cia8 herein, polypeptides thereof, and the nucleic acids that encode them. Also provided herein are modified cells and transgenic plants that can include and/or express a Cia8 polypeptide and/or nucleic acid encoding the Cia8 polypeptide. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Nucleic acid Sequences

Isolated Nucleotide and cDNA Sequences

The present disclosure describes isolated nucleotide and cDNA sequences, which either in whole or in part, can encode a green alga Cia8 polypeptide. In some embodiments, the green alga Cia8 polypeptide encoded by an isolated or synthetic nucleotide or cDNA sequence provided herein can bind and/or transport bicarbonate.

In some embodiments, a nucleotide encoding a green alga Cia8 polypeptide can have an isolated nucleotide sequence about 100% identical to any one of SEQ ID NOs: 1-3. In some embodiments, cDNA encoding the green alga Cia8 can have a sequence about 100% identical to SEQ ID NO: 3. The cDNA can have a sequence with at least 99% identity to any one of SEQ ID NO: 3. In some embodiments, the cDNA can a sequence having at least 98% identity to any one of SEQ ID NO: 3. In other embodiments, the cDNA can have a sequence having at least 95%, at least 90%, at least 85%, at least 80%, at least 70%, or at least 50% sequence identity to any one of SEQ ID NO: 3. In further embodiments, the cDNA sequence has between about 70% and about 80%, or between about 80% and 90%, or between about 90% and about 100% sequence identity with any one of SEQ ID NO: 3.

In some embodiments, the green alga Cia8 cDNA encodes a polypeptide having a sequence at least 90% identity to any one of SEQ ID NO: 4. In additional embodiments, the green alga Cia8 cDNA encodes a polypeptide having a sequence between about 90% and about 100% sequence identity to any one of SEQ ID NO: 4. In other embodiments, the green alga Cia8 cDNA encodes a polypeptide having a sequence between about 50% and about 100% sequence identity to any one of SEQ ID NO: 4.

The present disclosure also provides isolated nucleotide fragments, including synthetic nucleotide fragments and cDNA fragments, of at least 6 nucleotides sequences having between about 90% and 100%, between about 95% and about 100%, or between about 99% and 100% sequence identity with any sequence within any one of SEQ ID NOs: 1-3. In some embodiments, the isolated nucleotide or synthetic nucleotide fragments have about 50% to about 100% sequence identity to any one of SEQ ID NOs: 1-3.

In some embodiments, the isolated or synthetic nucleotide fragment can encode a peptide or polypeptide capable of binding and/or transporting bicarbonate across a membrane.

Recombinant Polynucleotide Sequences

Also provided are recombinant polynucleotide sequences having any of the isolated nucleotide or cDNA sequences or fragments thereof previously described and additional polynucleotide sequences operatively linked to the isolated nucleotide or cDNA sequences or fragments thereof. In some embodiments, non-coding nucleotides can be placed at the 5' and/or 3' end of the polynucleotides encoding a green alga Cia8 polypeptide without affecting the functional properties of the molecule. A polyadenylation region at the 3'-end of the coding region of a polynucleotide can be included. The polyadenylation region can be derived from the endogenous gene, from a variety of other plant genes, from T-DNA, or through chemical synthesis. In further embodiments, the nucleotides encoding the a green alga Cia8 polypeptide can be conjugated to a nucleic acid encoding a signal or transit (or leader) sequence at the N-terminal end (for example) of the green alga Cia8 polypeptide that co-translationally or post-translationally directs transfer of the green alga Cia8 polypeptide. The polynucleotide sequence can also be altered so that the encoded green alga Cia8 polypeptide is conjugated to a linker, selectable marker, or other sequence for ease of synthesis, purification, and/or identification of the protein. In one embodiment, the recombinant polynucleotide sequence includes at least one regulatory sequence operatively linked to the isolated nucleotide or cDNA sequences or fragments thereof.

To express an exogenous green alga Cia8 gene, fragment thereof, or antisense nucleotide in a cell, the exogenous nucleotide can be combined (e.g., in a vector) with transcriptional and/or translational initiation regulatory sequences, i.e. promoters, that direct the transcription of the gene and/or translation of the encoded protein in a cell. In some embodiments a constitutive promoter may be employed. Suitable constitutive promoters for plant cells include, but are not limited to, the cauliflower mosaic virus (CaMV) 35S transcription initiation region, the 1'- or 2'-promoter derived from T-DNA of *Agrobacterium tumefaciens*, the ACT11 and Cat3 promoters from *Arabidopsis* (Huang et al. Plant Mol. Biol. 1996, 33:125-139 and Zhong et al. Mol. Gen. Genet. 1996, 251:196-203), the stearoyl-acyl carrier protein desaturase gene promoter from *Brassica napus* (Solocombe et al. Plant Physiol. 1994, 104:1167-1176), and the GPc 1 and Gpc2 promoters from maize (Martinez et al. J. Mol. Biol. 1989, 208:551-565 and Manjunath et al. Plant Mol. Biol. 1997, 33:97-112). Suitable constitutive promoters for bacterial cells, yeast cells, fungal cells are generally known in the art, such as a T-7 promoter for bacterial expression and an alcohol dehydrogenase promoter for expression in yeast.

In other embodiments, tissue-specific promoters or inducible promoters may be employed to direct expression of the exogenous nucleic acid in a specific cell type, under certain environmental conditions, and/or during a specific state of development. Examples of environmental conditions that may affect transcription by inducible promoters include anaerobic conditions, elevated temperature, the presence of light, contact with chemicals or hormones, or infection by a pathogen. Suitable plant inducible promoters include the root-specific ANRI promoter (Zhang and Forde. Science. 1998, 279:407), the photosynthetic organ-specific RBCS promoter (Khoudi et al. Gene. 1997, 197:343) and the tomato fruit ripening-specific E8 promoter (Deikman, J., et al. Plant Physiol. 1992, 100: 2013-2017).

A selectable marker can also be included in the recombinant nucleic acid to confer a selectable phenotype on plant cells. For example, the selectable marker may encode a protein that confers biocide resistance, antibiotic resistance (e.g., resistance to kanamycin, G418, bleomycin, hygromycin), or herbicide resistance (e.g., resistance to chlorosulfuron or Basta). Thus, the presence of the selectable phenotype indicates the successful transformation of the host cell. An exemplary selectable marker includes the beta-glucuronidase (GUS) reporter gene.

Suitable recombinant polynucleotides can be obtained by using standard methods known to those of skill in the art, including but not limited to, restriction enzyme digestion, PCR, ligation, and cloning techniques. In some embodiments, the recombinant polynucleotide encodes a peptide or polypeptide that can be capable of binding and/or transporting bicarbonate across a membrane.

Isolated Protein (Polypeptide) and Peptide Sequences

The present disclosure also describes an isolated or synthetic protein (polypeptide) corresponding to a solute carrier from green alga, such as Cia8. In some embodiments, the isolated polypeptide can have an amino acid sequence corresponding to SEQ ID NO: 4. The isolated or synthetic polypeptide can have an amino acid sequence with at least about 99% identity to SEQ ID NO: 4. In some embodiments, the isolated or synthetic polypeptide can have an amino acid sequence having at least about 98% identity to SEQ ID NO: 4. In other embodiments, the isolated polypeptide can have an amino acid sequence having at least about 95%, at least about 90%, at least about 85%, at least about 80%, at least about 70%, or at least about 50% sequence identity to SEQ ID NO: 4. In some embodiments, the isolated or synthetic polypeptide has greater than about 70%, or between about 70% and about 90%, or between about 90% and 100% sequence identity to SEQ ID NO: 4.

In some embodiments, the isolated or synthetic polypeptide can be capable of binding and/or transporting bicarbonate across a membrane. In some embodiments, the isolated or synthetic peptide can be capable for improving growth in low $CO_2$ conditions. In some embodiments, the low $CO_2$ conditions can be atmospheric levels of $CO_2$. In some embodiments, the low $CO_2$ conditions can be less than about 3% $CO_2$.

Modifications and changes can be made in the structure of the polypeptides of the present disclosure that result in a molecule having similar characteristics as the unmodified polypeptide (e.g., a conservative amino acid substitution). Modification techniques are generally known in the art. For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a functional variant. Polypeptides with amino acid sequence substitutes that still retain properties substantially similar to polypeptides corresponding to green alga Cia8 are within the scope of this disclosure.

The present disclosure also includes isolated and synthetic peptides corresponding to a fragment of the polypeptide corresponding to green alga Cia8. In some embodiments the peptides correspond to a portion of SEQ ID NO: 4. The isolated or synthetic peptides can have at least about 90%, or at least about 95%, or at least about 99% sequence identity to any portion of SEQ ID NO: 4. In some embodiments, the isolated or synthetic peptides can have between about 90% and about 95%, or between about 95% and about 99%, or between about 99% and about 100% sequence identity to a sequence within SEQ ID NO: 4.

In some embodiments, the isolated or synthetic peptide can be capable of binding and/or transporting bicarbonate across a membrane. In some embodiments, the isolated or synthetic peptide can be capable for improving growth in low $CO_2$ conditions. In some embodiments, the low $CO_2$ conditions can be atmospheric levels of $CO_2$. In some embodiments, the low $CO_2$ conditions can be less than about 3% $CO_2$.

In other embodiments, the isolated or synthetic peptide or fragment thereof as described herein is suitable for use in production of antibodies against green alga Cia8. In other words, the isolated or synthetic peptide as described herein serves as the antigen to which an antibody is raised against. In some embodiments, the isolated or synthetic peptide sequence or fragment thereof is also the epitope of the antibody. Antibodies raised against green alga Cia8 are suitable for use in methods for at least detection, quantification, and purification of green alga Cia8. Other uses for green alga Cia8 antibodies are generally known in the art.

Vectors

Vectors having one or more of the polynucleotides or antisense polynucleotides described herein can be useful in producing transgenic bacterial, fungal, yeast, plant cells, and transgenic plants that express varying levels of a green alga Cia8. Within the scope of this disclosure are vectors containing one or more of the polynucleotide sequences described herein.

In one embodiment, the vector can include a polynucleotide encoding a green alga Cia8, where the DNA molecule has at least about 90%, or between about 90% and about 95%, or between about 95% and about 100% sequence identity with any one of SEQ ID NOs: 1-3. In some embodiments, the vector can include a DNA molecule encoding a green alga Cia8, where the DNA molecule has at least about 90%, or between about 90% and about 95%, or about 95% and about 100% sequence identity with any one of SEQ ID NOs: 1-3, and where the green alga Cia8 can bind and or transport bicarbonate and/or improve growth of the alga in low $CO_2$ conditions. In some embodiments, the vector has a cDNA molecule that encodes a polypeptide having a sequence with at least about 90%, or between about 90% and about 95%, or between 95% and about 100% sequence identity to SEQ ID NO: 3.

In one embodiment, the vector can have at least one regulatory sequence operatively linked to a DNA molecule or encoding a green alga Cia8 such that the green alga Cia8 is expressed in a bacteria, fungus, yeast, plant, or other cell into which it is transformed. In other embodiments, the vector includes a promoter that serves to initiate expression of the green alga Cia8 such that the green alga Cia8 is over-expressed in a plant cell into which it is transformed relative to a wild-type bacteria, fungus, yeast, or plant cell. In some embodiments, the vector can have at least one regulatory sequence operatively linked to a DNA molecule encoding a green alga Cia8 and a selectable marker.

Transgenic Plants

The polynucleotide sequences and vectors described above can be used to produce transgenic plants. The present disclosure includes transgenic plants having one or more cells where the one or more cells contain any of the recombinant polynucleotides or vectors previously described that have DNA sequences encoding the green alga Cia8. In one embodiment, the recombinant polynucleotide contains at least one regulatory element operatively linked to a green alga Cia8 DNA sequence having at least about 90%, or between about 90% and about 95%, or between about 95% and about 100% sequence identity with any one of SEQ ID NOs: 1-3.

Also described herein are transgenic plants having one or more cells transformed with vectors containing any one or more of the nucleotide sequences described above, and/or fragments of the nucleic acids encoding the green alga Cia8 proteins of the present disclosure. In some embodiments, the vector contains a green alga Cia8 DNA sequence having at least about 90%, or between about 90% and about 95%, or between about 95% and about 100% sequence identity with any one of SEQ ID NOs1-3. The transgenic plant can be made from any suitable plant species or variety including, but not limited to *Arabidopsis*, rice, wheat, corn, maize, tobacco, soybean, Brassicas, tomato, potato, alfalfa, sugarcane, and *sorghum*.

In some embodiments, the transgenic plant having a nucleotide sequence encoding green alga Cia8 can have increased gene and/or protein expression of green alga Cia8 relative to a wild type plant. In other embodiments, the transgenic plant has a nucleotide sequence encoding green alga Cia8 has increased expression of green alga Cia8 relative to a wild type plant and produces a green alga Cia8 polypeptide. The green alga Cia8 polypeptide can be capable of binding and/or transporting bicarbonate across a membrane.

In some embodiments, the transgenic plant produces a green alga Cia8 that can bind and/or transport bicarbonate. In some embodiments, the transgenic plant can produce a green alga Cia8 protein and have improved growth in low $CO_2$ conditions. In some embodiments, the low $CO_2$ conditions can be atmospheric levels of $CO_2$. In some embodiments, the low $CO_2$ conditions can be less than about 3% $CO_2$.

A transformed plant cell of the present disclosure can be produced by introducing into a plant cell on or more vectors as previously described. In one embodiment, transgenic plants of the present disclosure can be grown from a transgenic plant cell transformed with one or more of the vectors previously described. In one embodiment, the cells can be transformed with a vector including a recombinant polynucleotide encoding a green alga Cia8 having at least about 90%, or between about 90% and about 95%, or between about 95% and about 100% sequence identity with any one of SEQ ID NOs: 1-3. In some embodiments, at least one regulatory sequence can be operatively linked to the DNA molecule.

Techniques for transforming a wide variety of plant cells with vectors or naked nucleic acids are well known in the art and described in the technical and scientific literature. See, for example, Weising et al. Ann. Rev. Genet. 1988, 22:421-477. For example, the vector or naked nucleic acid may be introduced directly into the genomic DNA of a plant cell using techniques such as, but not limited to, electroporation and microinjection of plant cell protoplasts, or the recombinant nucleic acid can be introduced directly to plant tissue using ballistic methods, such as DNA particle bombardment.

Microinjection techniques are known in the art and well described in the scientific and patent literature. The introduction of a recombinant nucleic acid using polyethylene glycol precipitation is described in Paszkowski et al. EMBO J. 1984, 3:2717-2722. Electroporation techniques are described in Fromm et al. Proc. Natl. Acad. Sci. USA. 1985, 82:5824. Ballistic transformation techniques are described in Klein et al. Nature. 1987, 327:70-73. The recombinant nucleic acid may also be combined with suitable T-DNA flanking regions and introduced into a conventional *Agrobacterium tumefaciens* host vector, or other suitable vector. The virulence functions of the *Agrobacterium tumefaciens* host will direct the insertion of the recombinant nucleic acid including the exogenous nucleic acid and adjacent marker into the plant cell DNA when the cell is infected by the bacteria. *Agrobacterium tumefaciens*-mediated transformation techniques, including disarming and use of binary vectors, are known to those of skill in the art and are well described in the scientific literature. See, for example, Horsch et al. Science. 1984, 233:496-498; Fraley et al. Proc. Natl. Acad. Sci. USA. 1983, 80:4803; and Gene Transfer to Plants, Potrykus, ed., Springer-Verlag, Berlin, 1995.

A further method for introduction of the vector or recombinant nucleic acid into a plant cell is by transformation of plant cell protoplasts (stable or transient). Plant protoplasts are enclosed only by a plasma membrane and will therefore more readily take up macromolecules like exogenous DNA. These engineered protoplasts can be capable of regenerating whole plants. Suitable methods for introducing exogenous DNA into plant cell protoplasts include electroporation and polyethylene glycol (PEG) transformation. Following electroporation, transformed cells are identified by growth on appropriate medium containing a selective agent.

The presence and copy number of the exogenous nucleic acid in a transgenic plant can be determined using methods well known in the art, e.g., Southern blotting analysis, PCR, and sequencing. Expression of the exogenous green alga Cia8 nucleic acid in a transgenic plant can be confirmed by detecting an increase of green alga Cia8 mRNA and/or the green alga Cia8 polypeptide in the transgenic plant. Methods for detecting and quantifying mRNA or proteins are well known in the art.

Transformed plant cells that are derived by any of the above transformation techniques, or other techniques now known or later developed, can be cultured to regenerate a whole plant. In embodiments, such regeneration techniques may rely on manipulation of certain phytohormones in a tissue culture growth medium, typically relying on a biocide or herbicide selectable marker that has been introduced together with the exogenous nucleic acid. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. Ann. Rev. Plant Phys. 1987, 38:467-486.

Once the exogenous green alga Cia8 has been confirmed to be stably incorporated in the genome of a transgenic plant, it can be introduced into other plants by sexual crossing. Any of a number of standard breeding techniques can be used, depending upon the species to be crossed.

Transformed Cells

This disclosure also encompasses one or more cells transformed with one or more isolated nucleotide or cDNA sequences and/or vectors as previously described. In some embodiments, the transformed cell is a plant, bacterial, fungal, or yeast cell. In one embodiment, a plant, bacterial, fungal or yeast cell contains one or more vectors as previously described. Also, within the scope of this disclosure are populations of cells where about 1% to about 100%, or between about 50% and about 75%, or between about 75% and about 100% of the cells within the population contain a vector as previously described.

In some embodiments, one or more cells within the population contain more than one type of vector. In some embodiments, all (about 100%) the cells that contain a vector have the same type of vector. In other embodiments, not all the cells that contain a vector have the same type of vector or plurality of vectors. In some embodiments, about 1% to about 100%, or between about 50% and about 75%, or between about 75% and about 100% of the cells within the population contain the same vector or plurality of vectors. In some cell populations, all the cells are from the same species. Other cell populations contain cells from different species. Transfection methods for establishing transformed (transgenic) cells are well known in the art.

In one embodiment, the transformed cells produce and/or express a peptide or polypeptide that is capable of binding and/or transporting bicarbonate across a membrane.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

This Example can demonstrate identification and characterization of a gene, designated Cia8 herein (Phytozome ID: Cre09.g395700), encoding a solute carrier protein, identified in a mutagenesis screen. The Cia8 gene encodes a transmembrane protein that belongs to $Na^+$/bile acid symporter family (SBF), a group of conserved transmembrane proteins (Pushkin and Kurtz, 2006) belonging to the solute carrier protein (SLC) superfamily. The results can demonstrate that the Cia8 gene product can be involved in bicarbonate uptake in *C. reinhardtii* and/or improve growth in low $CO_2$ conditions.

Results

The Cia8 Mutant Requires High $CO_2$ Conditions to Grow Well

Figure 1B:
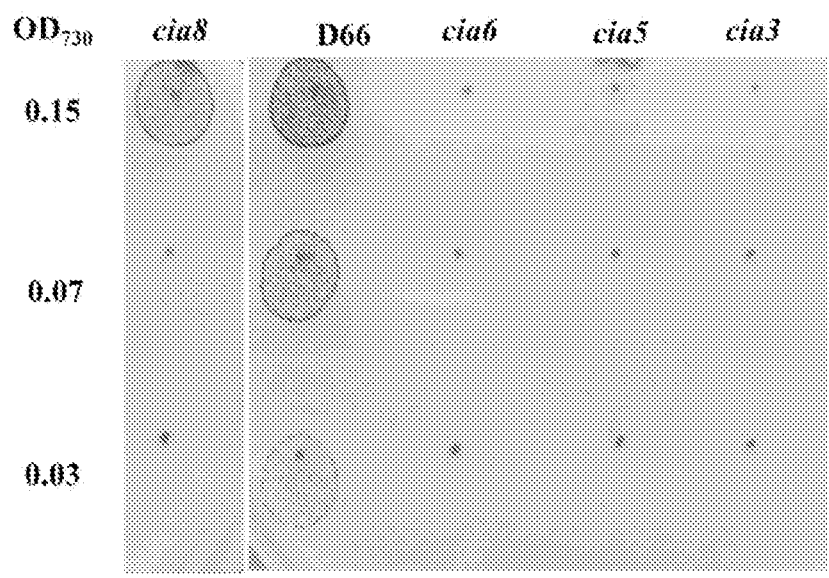
Figure 1C:
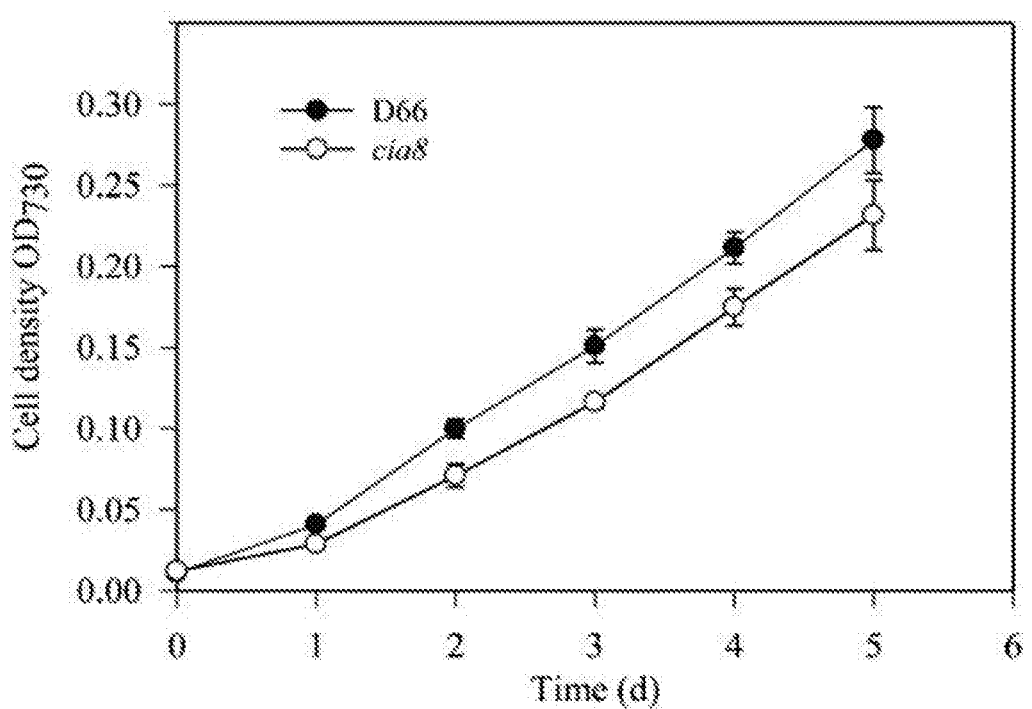

The Cia8 mutant was identified following an insertional mutagenesis screen using a 1.8-kb AphVIII para$^R$ cassette containing the aminoglycoside 3'-phosphotransferase type VIII encoding gene (AphVIII) from *Streptomyces rimosus* which confers paromomycin resistance (Sizova et al., 2001). Mutants were screened by growing them on high $CO_2$ (about 5%) and low $CO_2$ (about 0.01%) on MIN plates in which potential CCM mutants would show slow growth when grown on low $CO_2$ (Jungnick et al., 2014). While the Cia8 mutant grew well on high $CO_2$ conditions (FIG. 1A), it showed weaker growth on low $CO_2$ (FIG. 1B) and was thus taken for further investigation. The slow growing phenotype was also apparent when cells were grown in liquid (MIN) culture at 0.01% C)2, where the doubling tie for the cia8 mutant was about 30 h as compared with 20 h for D66 (FIG. 1C).

Confirmation of Insertion

Figure 2A:
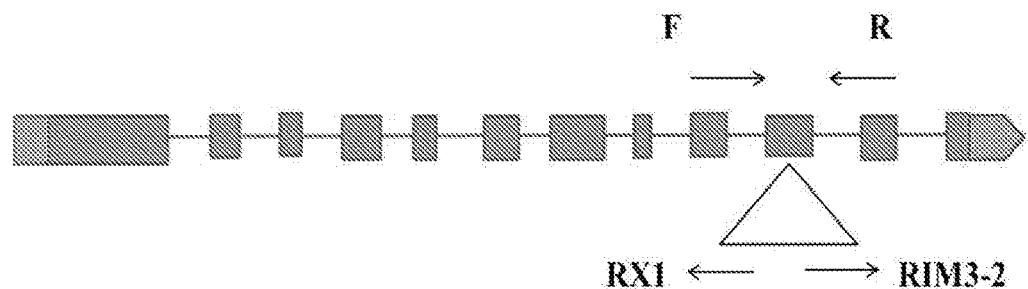
FIGS. 2A-2B shows (FIG. 2A) the genomic structure of the Cia8 gene locus (ID:Cre09.g395700) showing the position of AphVIII insertion. Green bars, spaces and orange bars represent exons, introns and untranslated regions respectively.
Figure 2B:
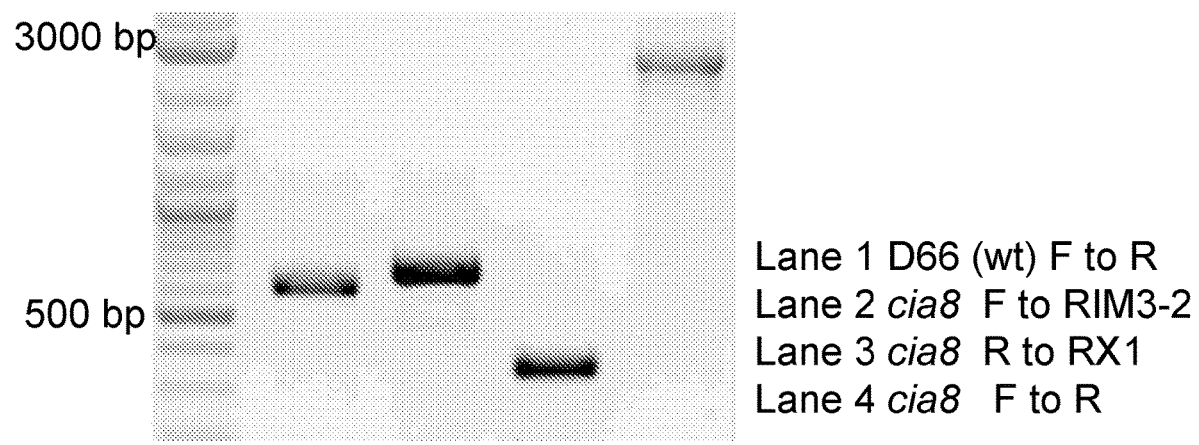

The location of the AphVIII insert in the Cia8 gene was determined using the adaptor PCR described by Pollock et al. (2016). The insertion is located in the 10th exon of the Cia8 gene as shown in the gene model in FIG. 2A. PCR amplification was done to confirm presence of the insertion using 2 primer pairs that amplify the 5'UTR and 3' UTR of the insertion (FIG. 2B). Table 2 shows a list of primers used in the study. The genomic DNA flanking the insertion site in this mutant was isolated and sequenced. Analysis of the sequenced genomic DNA revealed a deletion of 16 bases of the gene sequence at the 5' UTR of the cassette (at the end of the insertion), and a new region of 19 bases was inserted. The 3' UTR of the insertion was intact with no deletion or insertion. The analysis confirmed that the target gene sequence had been disrupted in the 10th exon and that no other large DNA deletions or insertions had occurred.

Gene Expression

Figure 3:
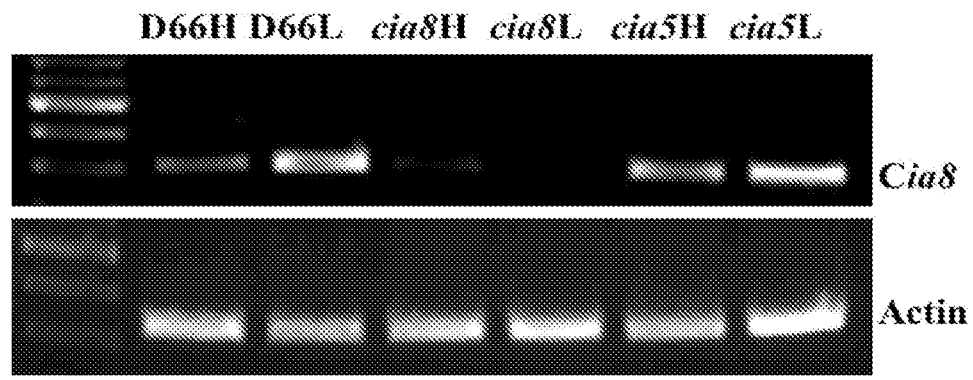
FIG. 3 shows RT-PCR analysis of D66 and Cia8 mutant strains using poly (A) RNA from high and low $CO_2$ grown cells as templates for Reverse Transcriptase PCR. For Cia8, the primers shown in Table 2 amplify a 1,500 bp product from cDNA. Beta actin was used as a loading control.

Disruption of the transcription in the gene was also confirmed by reverse-transcription PCR (RT-PCR) using a gene specific primer pair spanning the insertion site. RT-PCR results show that there is no detectable expression of the intact Cia8 transcript in the Cia8 mutant (FIG. 3), confirming that the transcript has been disrupted and that the gene product in the mutant is below detectable levels. Lici8 mRNA was detected in wildtype high $CO_2$ cells. A marked upregulation of transcript in low $CO_2$ cells was observed (FIG. 3), suggesting that the Cia8 gene is inducible under low $CO_2$ conditions. The result from this RT-PCR also shows that the gene encoding CIA8 does not appear to be regulated by the Cia5 gene, the master regulator of most CCM genes, as the transcript was equally expressed in the Cia5 mutant as in the wild type.

Genetic crosses of the Cia8 mutant with wild-type strain demonstrated a 1:1 segregation ratio of paromomycin resistant to paromomycin-sensitive progeny (data not shown) illustrating that the mutant carries a single insertion. Further investigation by PCR demonstrated that the paromomycin resistant strains carried the cassette. Phenotypic analysis showed the tetrads with resistance to paromomycin were consistently sick on low $CO_2$ conditions. Taking the results together, it was concluded that Cia8 gene locus is segregating with, and therefore responsible for the observed slow growth phenotype under low $CO_2$ conditions.

Prediction of Structure and Transmembrane Domains of the Cia8 Gene

Figure 4:
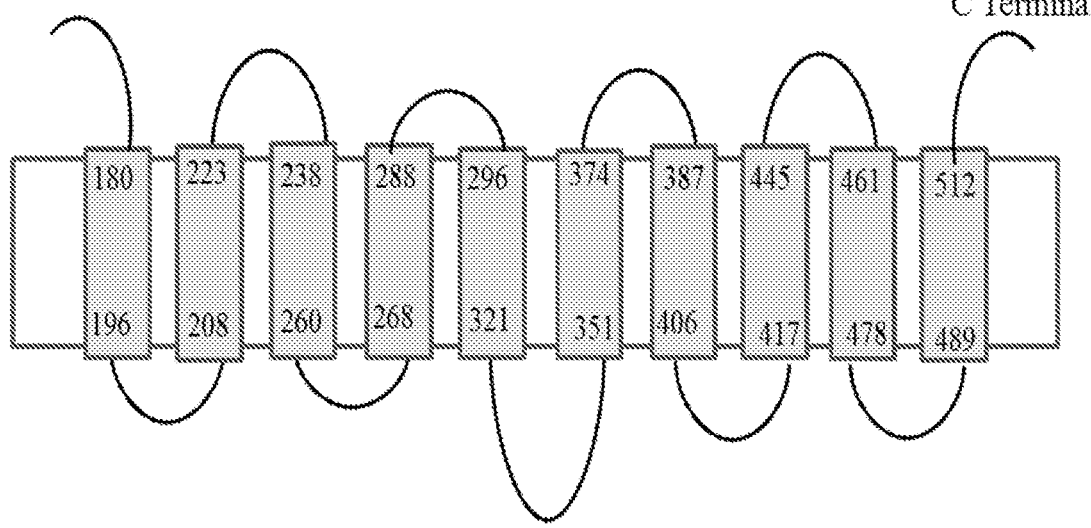
FIG. 4 shows a topology model predictions for CIA8 based on the alignment with Yersinia frederiksenii SLC4. The grey boxes are putative membrane spanning helices connected by loops of variable lengths. 62% of the residues were modelled at >90% confidence level. Predictions were generated by PHYRE2 (Kelley et al., 2015).

A comparison of cDNA and genomic sequences shows that Cia8, located on chromosome 9 in the genome has 12 exons. On the basis of nucleotide sequence, Cia8 encodes a polypeptide of 529 amino acids and aligns best with sodium/bile acid (SBF-like) solute carrier protein group. The PHYRE2 software (Kelley et al., 2015) was used to predict the structure of the protein. Using the core transmembrane part of the protein containing 370 amino acids (amino acids 160-529) gave the highest homology scores. Prediction results revealed 10 putative transmembrane domains with 15-24 amino acid and extracellular loops between the transmembrane helices of 8-30 amino acids as shown in FIG. 4. The third loop between TM 5 and 6 is longer than the rest, and this is a characteristic of SLC4 proteins. The protein threaded best to the crystal structure for a bacteria (*Yersinia frederikseni*) $Na^+$/metabolite symporter (82%), but it also threaded well to HapA proteins ($Na^+/H^+$ antiporters) from several bacteria (56-98%).

Similarity of CIA8 to Other Anion Transporters

Figure 9:
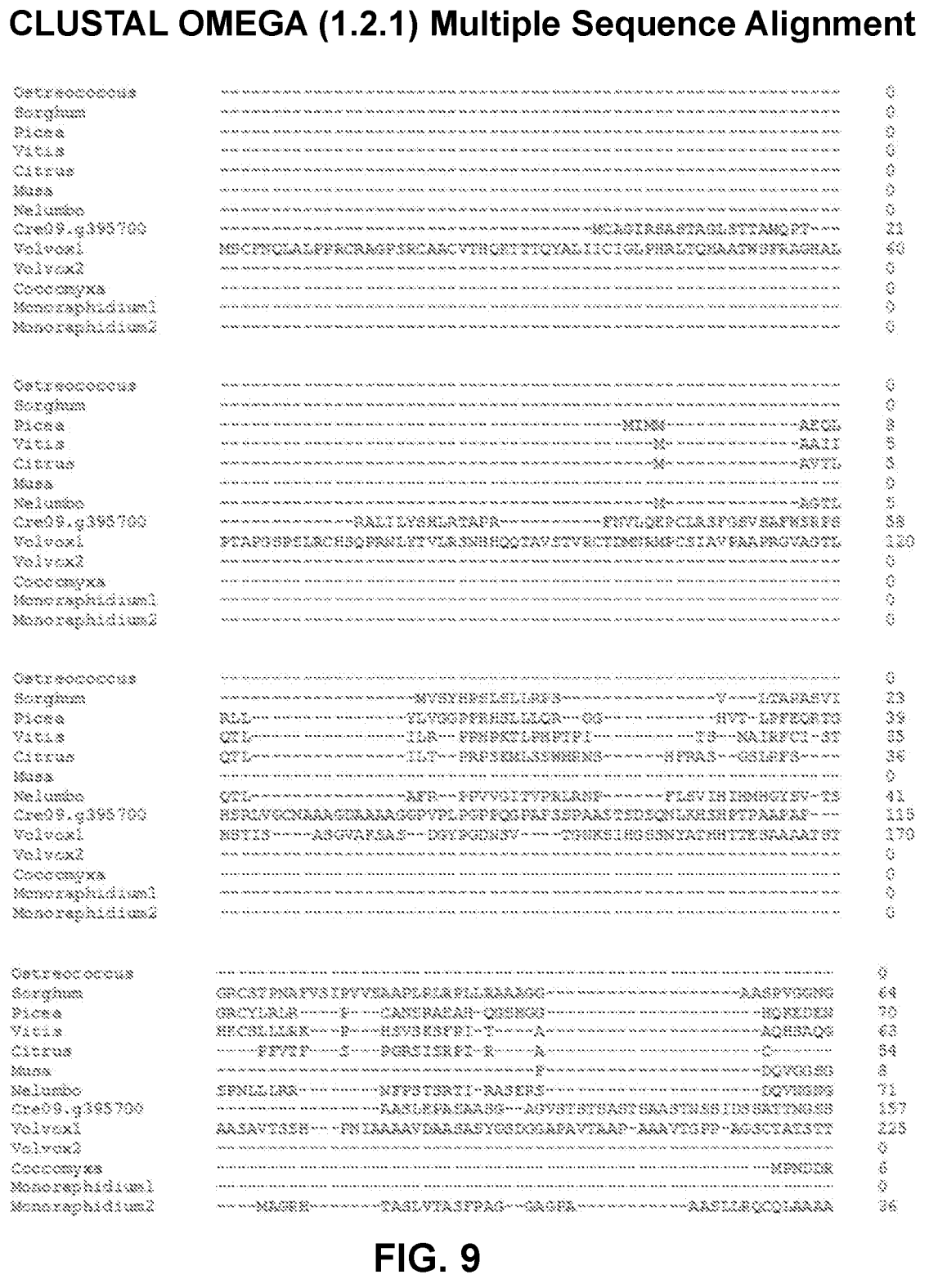

Searches in the PFAM database revealed eight other predicted proteins similar to CIA8: Cre02.g147450; Cre06.g250450; Cre09.g393250; Cre12.g521950; Cre10.g448350; Cre12.g532500; Cre02.g095085 and Cre02.g095086, all annotated as $Na^+$/bile acid transporters. Sequence identity of these proteins to CIA8 varies between 19 and 31%. The number of Na/bile acid transporter genes in *C. reinhardtii* is quite comparable to other species, with six having been reported in *Arabidopsis* (Sawada et al., 2009), seven in humans (He et al., 2009) and five in the marine diatom *Phaeodactylum tricornutum* (Ashworth et al., 2016). The numbers are not surprising considering the numbers of ions that are transported by these types of proteins. The CIA8 protein also shows considerable sequence similarity to several SBF clones from higher plant species, many of which have not yet been characterized (FIG. 9). The closest algal homologue was found in *Volvox carteri* with 76% identity. Another protein showing similarity to CIA8 was the yeast protein YNL275w with 23% identity. This yeast protein belongs to the $HCO_3^-$ transporter superfamily and has been shown to accept several anions, including $HCO_3^-$ as potential substrates (Zhao and Reithmeier, 2001). This analysis suggests that the Cia8 gene product belongs to a family of conserved membrane transport proteins characterized by conserved domains and it may be involved in Ci transport.

CIA8 has a Reduced Affinity for Ci

Figure 5A:
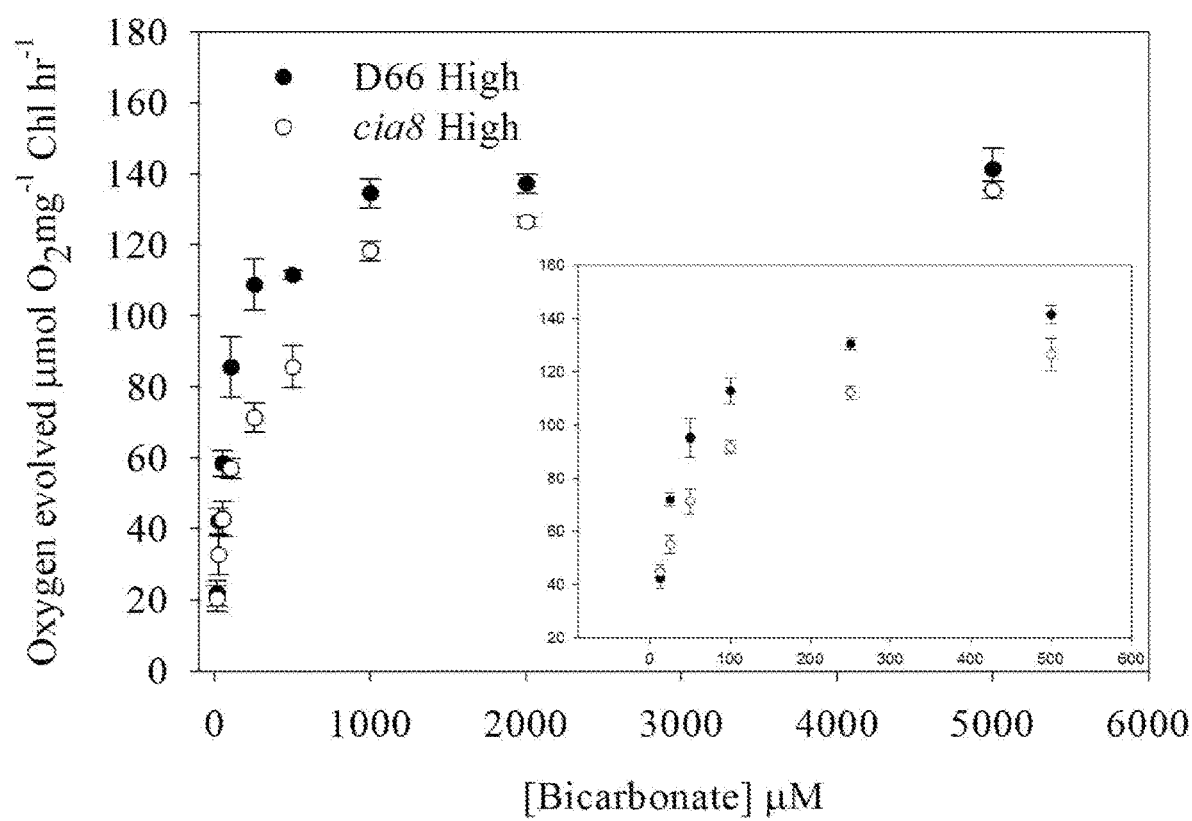
FIGS. 5A-5C show Ci-dependent photosynthetic oxygen evolution in C. reinhardtii wild-type and the Cia8 mutant. A, High $CO_2$-grown cells and B, Low $CO_2$-grown cells assayed at pH 7.3; C, low $CO_2$-grown cells assayed at pH 9.0. Cells were grown at high $CO_2$ and transferred to low $CO_2$ for 4 hr. The inserts in FIGS. 5A and 5B represent lower concentrations below 500 µM used for determination of $K_{(0.5)}$.
Figure 5B:
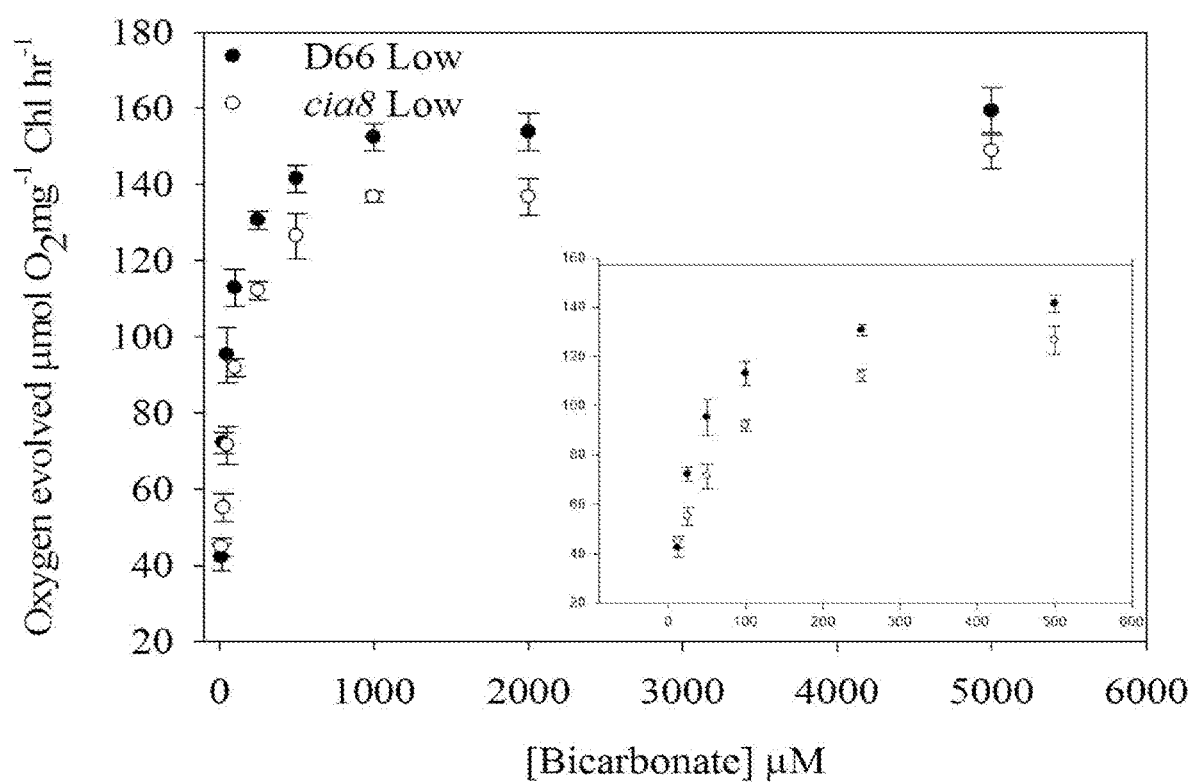
Figure 5C:
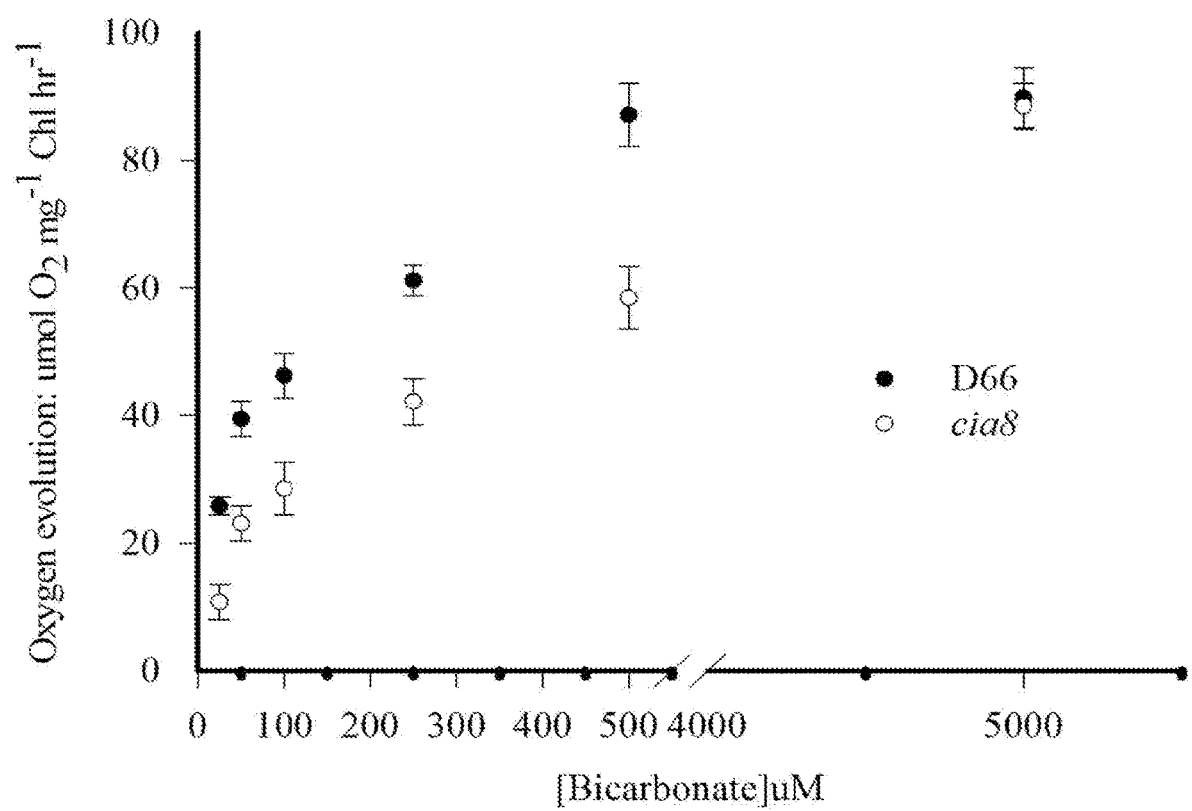

Since the expression of CIA8 is strongly responsive to $CO_2$ limitation, its possible function in the CCM was evaluated using physiological assays. Strains missing CIA8 exhibited a higher $K_{(0.5)}$ (Ci), indicating they had a lower affinity for inorganic carbon than wildtype cells (FIGS. 5A-5B). At pH (7.3) the $K_{(0.5)}$ (Ci) for wildtype cells was 25 µM. In contrast Cia8 mutant cells had a significantly higher $K_{(0.5)}$ (Ci) of 90 µM (Table 1), suggesting a reduced affinity for Ci in the mutant. Oxygen evolution was also measured at pH 9.0 with the presumption that the predominant Ci species in the medium would be bicarbonate hence, oxygen evolution is more dependent on active bicarbonate uptake. The shift in the $K_{(0.5)}$ was also significant at higher pH with Cia8 mutant cells exhibiting a greater $K_{0.5}$ (Ci) of 350 µM as compared to 100 µM in the wild-type cells (FIG. 5C, Table 1). This result confirms a reduced affinity for bicarbonate in the mutant, and consequently, a role for the Cia8 gene product in Ci uptake.

Localization of CIA8 to the Chloroplast in *C. reinhardtii*

Analysis using TargetP/ChloroP (http://www.cbs.dtu.dk/services/ChloroP/) suggested that the CIA8 peptide is a chloroplast membrane protein (score 81%). Another alignment of the N-terminal sequence of this protein was conducted using SCLpred-Bologna Biocomputing Group (schloro.biocomp.unibo.it). The software predicts that CIA8 has a chloroplast transit peptide (cTP; score 0.79) and thylakoid (0.81). It also predicts a location as a thylakoid membrane (0.6). As a control, Kea3.3, an *Arabidopsis* thylakoid antiporter was used, and the software predicts a cTP (score(0.77) and allocation as a thylakoid membrane (0.51). These predictions give the strong indication CIA8 is a chloroplast protein.

Figures 6A, 6B, 6C, 6D, 6E, 6F:
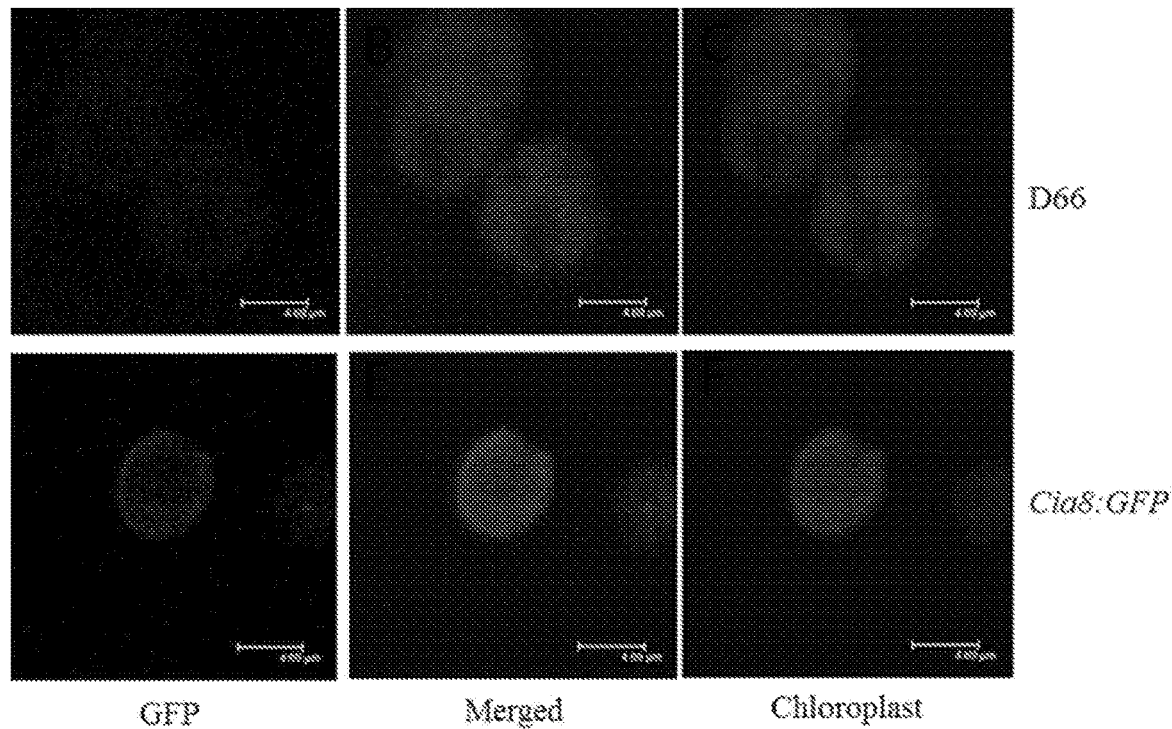
FIGS. 6A-6G show (FIGS. 6A-6F) live imaging of the CIA8-GFP transformant cells showing the localization of the chimeric protein. The top panel is the wt D66 strain, and the lower panel is the D66 strain transformed with the CIA8:CrGFP. The cells were grown on MIN plates and observed with a confocal microscope using the following wavelengths of light: Differential Interference Contrast—GFP:fluorescing at 410-470 nm; chlorophyll autofluorescence at 600-700 nm. Bars correspond to 4.69 µm.
Figure 6G:
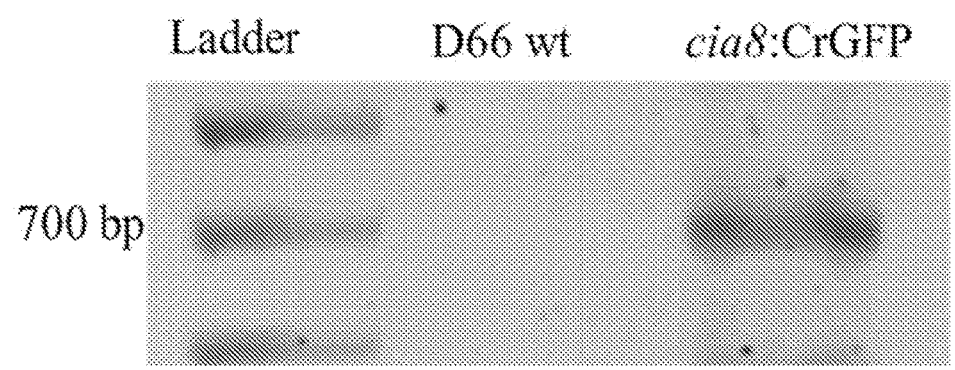

To confirm this subcellular localization, a *C. reinhardtii* line expressing the Cia8 coding sequence fused to GFP (CIA8:CrGFP) under the control of the PsaD promoter was generated. The PsaD promoter is a high expression promoter which drives a nuclear gene encoding an abundant chloroplast protein located on the stromal side of photosystem I in *C. reinhardtii* (Fischer and Rochaix, 2001). RT-PCR analysis revealed that GFP transcript was detectable in this strain (FIG. 6G).

Green fluorescence of the fused protein CIA8:CrGFP was detected in chloroplasts by live imaging on the confocal microscope. This result indicated that the CIA8 protein predominantly accumulates in the chloroplast of *C. reinhardtii* cells (FIGS. 6A-6F). However, the signal does not seem to be confined to the chloroplast envelope, but diffused throughout the organelle, suggesting a thylakoid localization.

CIA8 Transport is not Dependent on $Na^+$

Figure 10:
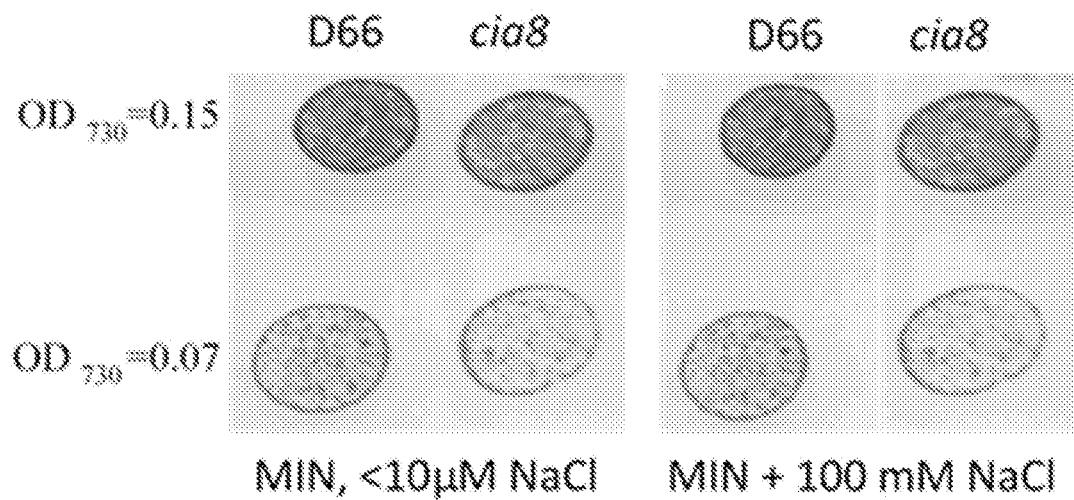
FIG. 10 shows growth of wild type D66 and CIA8 mutant cells of Chlamydomonas on MIN plates with and without 100 mM NaCl. 15 µL of actively growing cell culture was inoculated at each spot and grown for 7 d. ($OD_{730}$= 0.15~1.5×10⁶ cells). No differences in growth were observed in either strain when Na⁺ was added.

Several solute transporters are known to be $Na^+$ dependent, including BicA, a low affinity bicarbonate transporter in cyanobacteria (Price et al., 2004; Price and Howitt, 2011). To determine whether Cia8 gene function could be dependent on $Na^+$ ions, wildtype and mutant cells were grown on different concentrations of $Na^+$ (<10 µM-200 mM). Both cultures grew well on low $Na^+$ concentrations (<10 µM) up to 100 mM on pH 6.8 plates (FIG. 10). Growth of cells was, however, inhibited at 200 mM $Na^+$. The observation that wildtype and Cia8 cells grew well at low $Na^+$ concentration can indicate that $Na^+$ ions are not required for the acquisition of $HCO_3^-$ in *C. reinhardtii* and may reflect that external $Na^+$ concentration in fresh water is generally low <1 mM (Pootakham et al., 2010). However, as some of the transporters, including CIA8, are internal, it is not clear that changing the external $Na^+$ concentration would alter the internal concentration.

Expression of Cia8 is Upregulated on Low $CO_2$ Conditions

Figure 7C:
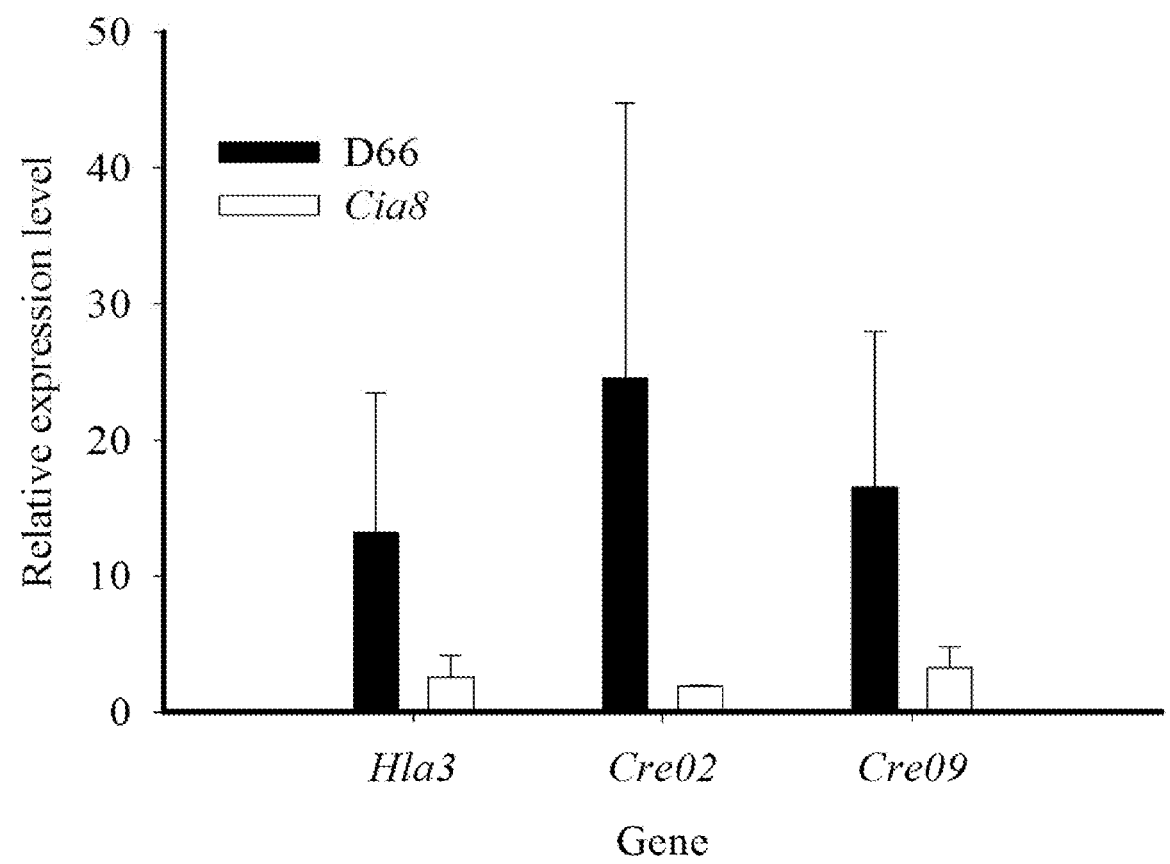

To quantify and compare the expression of the other known transporters in *Chlamydomonas* in the Cia8 mutant and in the wildtype, the expression of Hla3, Nar1.2, Lci1 and Cia8 as well as two other SLC genes (Gene ID:

Cre02.g147450 and Cre09.g393250) were investigated by quantitative RT-PCR analysis. RNA samples were obtained from high $CO_2$ and low $CO_2$ acclimated cultures. Results show the level of expression of these transporter genes in the wildtype (FIG. 7A), and in the Cia8 mutant (FIG. 7B). The results confirm upregulation of the Cia8 gene and the other transporters on acclimation to low $CO_2$ conditions, except for Hla3 which usually increases in expression at times greater than 4 hr (Duanmu et al., 2009). In the wildtype there was a 4-fold upregulation of the Cia8 gene on acclimation to low $CO_2$ conditions. There was also up-regulation of the two SBF genes in the wild-type cells. The relative expression levels of these two SBF genes were also somewhat lower in the cia8 mutant cells as compared with the wild type (FIG. 7C). While the ata confirm that the Cia8 gene product is involved in the CCM, they also suggest that a loss of CIA8 may affect the transcriptional control of the other genes normally up-regulated under low $CO_2$ conditions.

The relative expression levels of the bicarbonate transporters were lower in the Cia8 mutant cells as compared to the wildtype. This down-regulation may suggest a regulatory role of this Cia8 gene on the other transporters. There was also a notable upregulation of two other SLC genes in the wildtype cells. The data seems to be consistent with our premise that Cia8 gene product is involved in the CCM and its expression is controlled at transcriptional level.

Cia8 Gene can be Complemented

Figure 8A:
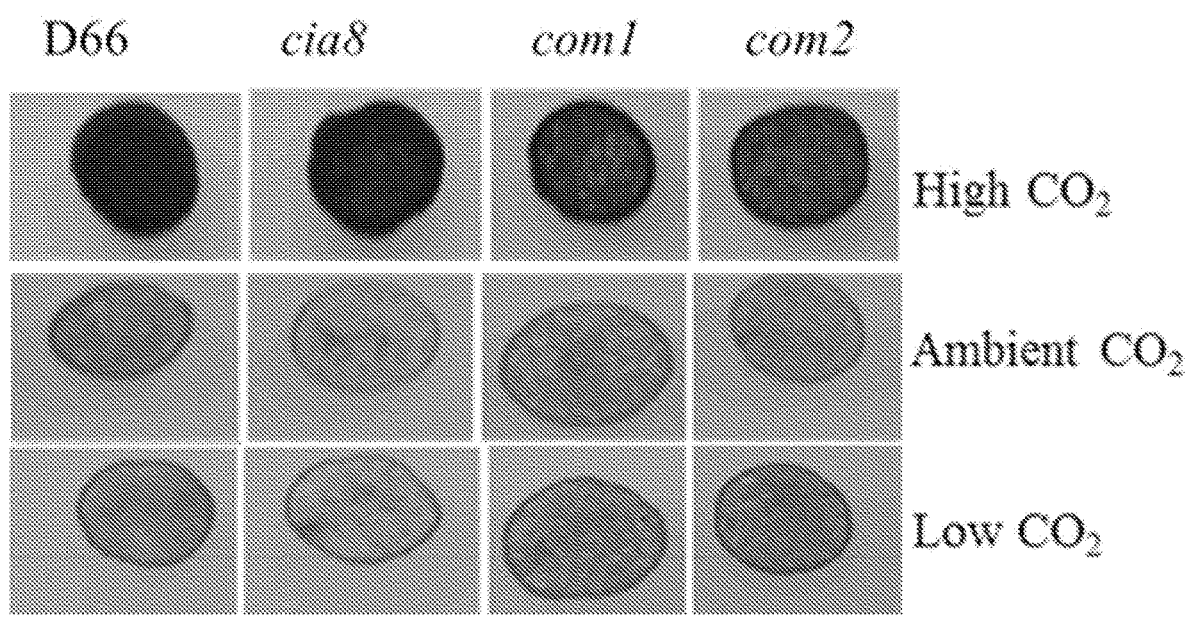
FIGS. 8A-8D show (FIG. 8A) a panel of images demonstrating growth phenotype of complemented Cia8 strains, com1 and com2. These strains had the wildtype Cia8 gene reintroduced into the Cia8 mutant as described herein.
Figure 8B:
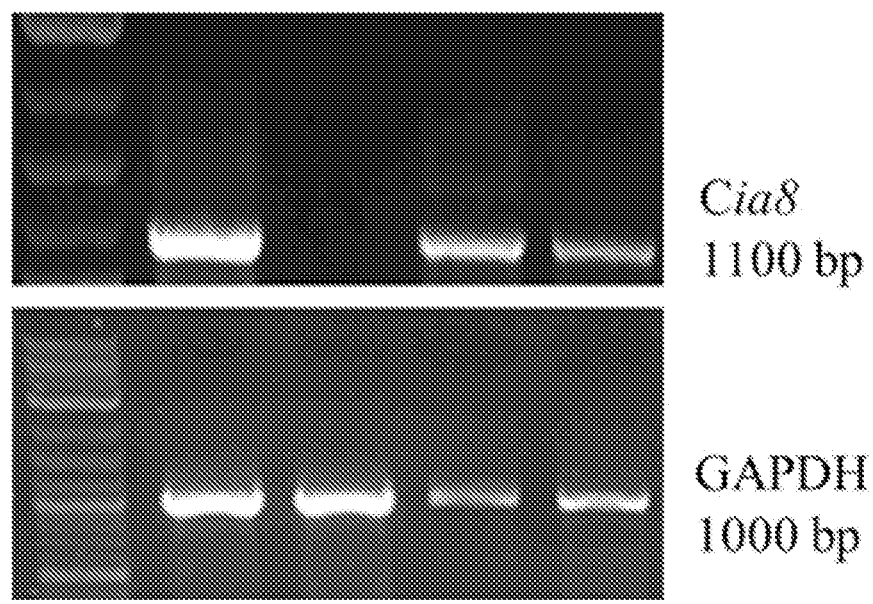
Figure 8C:
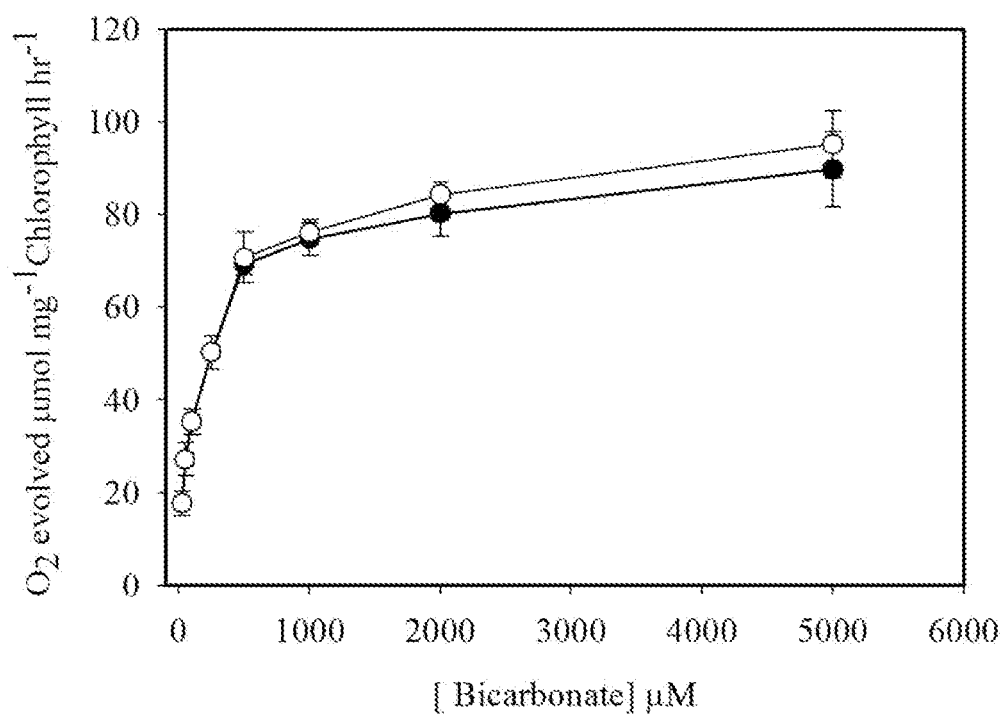
Figure 8D:
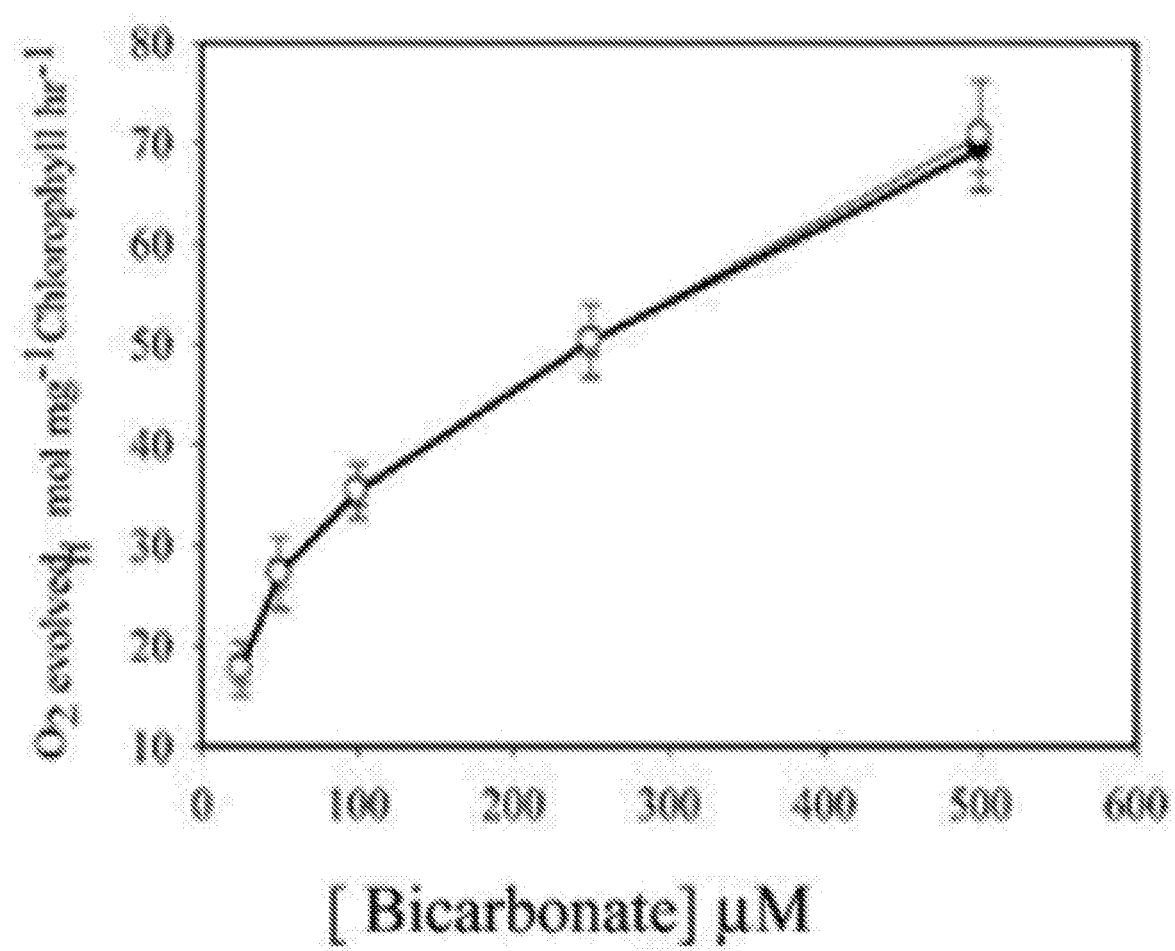

Complementation of CIA8 was achieved by expressing Cia8 cDNA (1,869 bp) including the entire 5'UTR and 3'UTR into the pSP124 vector under the control of its own promoter and terminator into the Cia8 mutant. Transformed cells were selected on bleomycin. Ten transformants were selected and subjected to further growth tests and photosynthesis assays. Results of growth show the wildtype phenotype on low $CO_2$ conditions is restored in complemented lines (referred to as com1 and com2) (FIG. 8A). RNA was extracted from these two complemented strains and cDNA synthesized. The resulting RT-PCR analysis showed that Cia8 transcript had been restored (FIG. 8B). In addition, the Ci-dependent oxygen evolution assay of com1 at pH 9.0 showed the $K_{(0.5)}$ (Ci) in the complemented strain was the same as that of wildtype. Also, the maximal oxygen evolved ($V_{max}$) was not significantly different from wildtype either (FIGS. 8C-8D). These results collectively confirm that this Cre09.g395700 coding sequence complemented growth of the Cia8 mutant, restoring the expression of transcript and functionality in Ci uptake.

Ci Uptake Assays

Figure 11A:
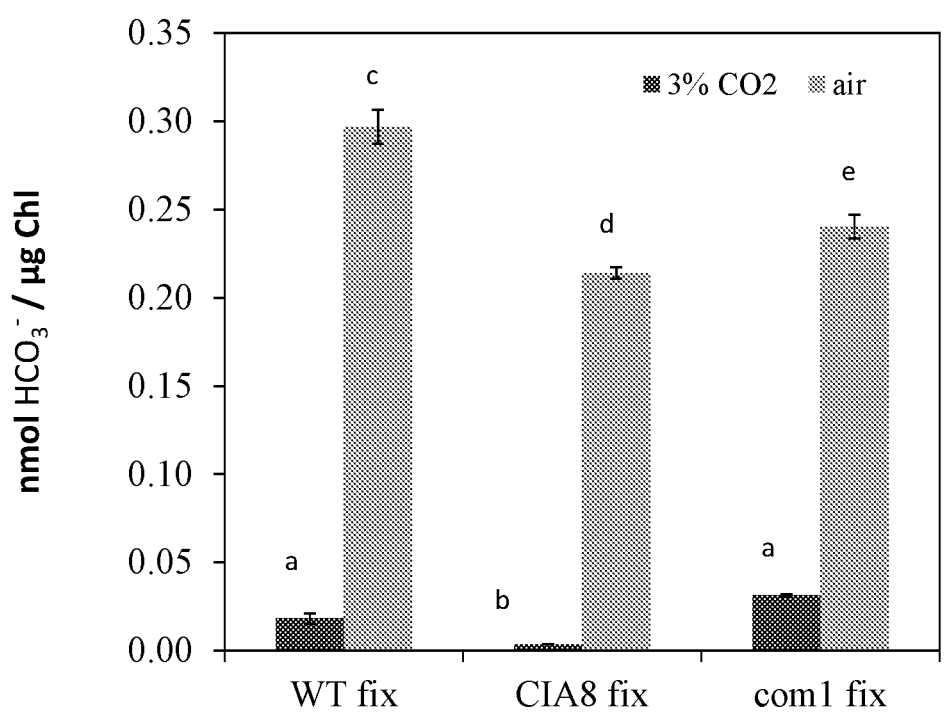
FIGS. 11A-11B show graphs demonstrating accumulation of $^{14}C$ 14C in wild-type (WT) D66, in the cia8 mutant, and in the complemented cell line com1. Cells were grown on elevated $CO_2$ (3% v/v CO2 in and acclimated to low $CO_2$. Analysis was done at pH 9.0.
Figure 11B:
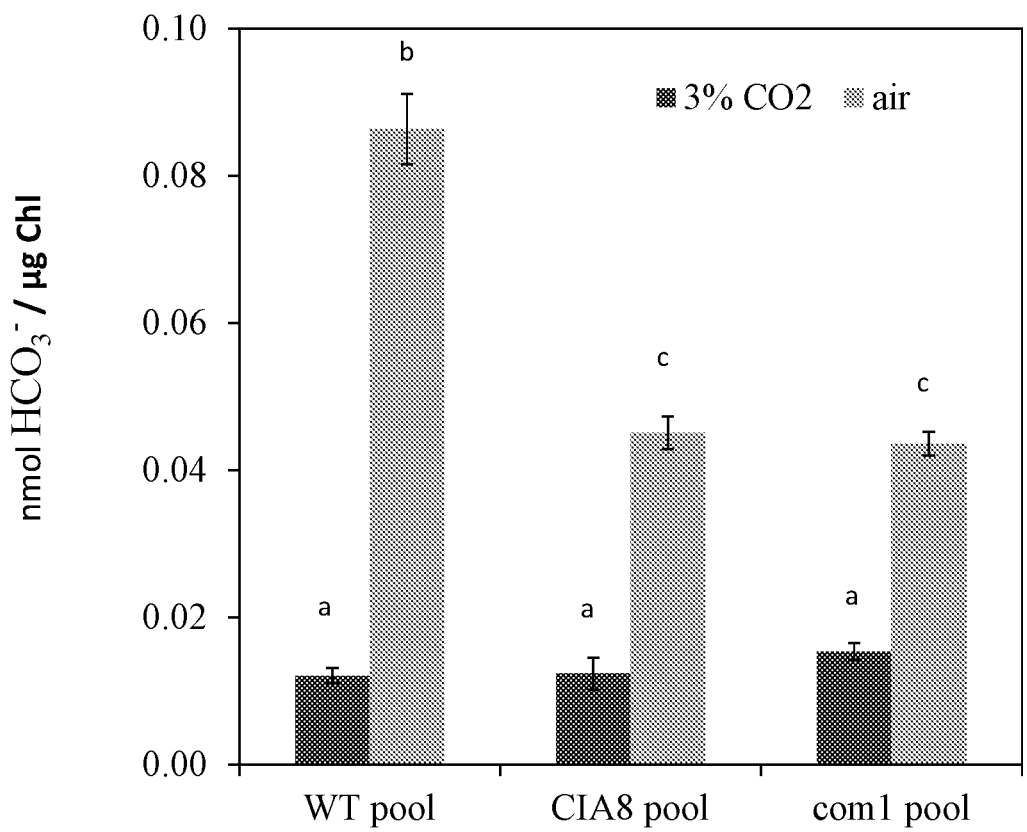

To evaluate the contribution of CIA8 to Ci uptake activity, the silicone oil layer centrifugation method was used to measure isotope discrimination, e.g. accumulation of $^{14}C$ in D66 and in CIA8, and in the complemented cell line com1 (FIGS. 11A-11B). Analysis was done at pH 9.0 to ensure the predominant Ci species was bicarbonate, using cells grown in elevated $CO_2$ (about 3% v/v $CO_2$ in air) or in air (low $CO_2$) cells. In all cases, the cells acclimated to low $CO_2$ had greater amounts of accumulated Ci in the cells than cells grown on elevated CO2 (FIG. 11A). When Ci uptake and photosynthetic rate were compared, wild-type cells had greater Ci accumulation and greater Ci fixation than Cia8 cells (FIG. 11B). In addition photosynthesis was nearly restored to wild-type levels in the com1 cells line although Ci accumulation was not fully restored. These data support the hypothesis that Ci uptake, most probably in the form of bicarbonate, is reduced in Cia8 cells.

Discussion

Bicarbonate transporters and the need for its uptake and accumulation are important features of the C. reinhardtii CCM. The putative bicarbonate transporters in C. reinhardtii are generally induced by limiting $CO_2$ conditions. It also appears that the transporters have overlapping functions. If the expression of only one transporter is reduced, there usually is not a strong growth phenotype, and a small effect on Ci uptake is observed. However, if two or more transporters are reduced, Ci uptake is affected and growth on low $CO_2$ is reduced. In this work, we generated new mutants by insertional mutagenesis and identified a mutant with an insertion in the gene (Phytozome ID: Cre09.g395700) which were named Cia8 (for low $CO_2$ inducible) or Cia8 (for Ci accumulation) and which are used interchangeably herein. The main objective of this Example was to determine whether the CIA8 protein participated in the CCM of C. reinhardtii. It was characterized and demonstrated that the insertion in this gene caused poorer growth on low $CO_2$ and resulted in a significant decrease in Ci affinity when cells were grown on limiting $CO_2$ conditions. In complementation experiments, the expression of the Cia8 coding region from the wildtype gene was able to restore normal growth phenotype and function in photosynthetic assays (FIGS. 8A-8D).

The CIA8 protein belongs to the SLC superfamily which encodes membrane-bound transporters belonging to ~55 sub-families. These SLC proteins transport a diverse number of substrates. Studies have shown that some SLC anion transporters are involved in bicarbonate uptake. Two sub-families namely $Na^+$-dependent $Cl^-/HCO_3^-$ exchangers (SLC4) and sulphate transporters (SLC26) have so far been implicated in bicarbonate transport in a marine diatom, cyanobacteria and mammals, with BAND3 being the prototype in humans (Price et al., 2004; Romero, 2005; Price and Howitt, 2011; Nakajima et al., 2013; Romero et al., 2013). Despite being important bicarbonate transporters in other eukaryotic species, this subfamily of SLC genes remains of unknown function in C. reinhardtii.

The CIA8 protein belongs to the SBF/BASS subfamily which includes membrane-bound transporters designated as bile acid transporters. These proteins transport a diverse number of substrates. In Arabidopsis, two of these genes have been characterized, and BASS2 is involved in pyruvate transport across the chloroplast envelope in methlerythritol 4-phosphate (MEP) pathway, whereas BASS4 transports 2-keto acids during glucosinolate metabolism (Gigolashvili et al., 2009; Furumoto et al., 2011). Bioinformatic searches in the PFAM database reveal that some SBF and SBF-like anion transporters may be involved in bicarbonate uptake. Despite being important transporters in other eukaryotic species, this subfamily of SBF/BASS gene products remains of unknown function in C. reinhardtii.

Physiological characterization of CIA8 in this study supports the idea that it is involved in CCM function and Ci uptake under limiting $CO_2$ conditions. The CIA8 transporter seems to make a significant contribution to CCM function because it is the only transporter so far that shows a distinct phenotype in single knockout mutants (FIG. 1). The other known transporters HLA3 and NAR1.2 did not show a definitive growth phenotype as single knock out mutants (Yamano et al., 2015) and no growth differences were reported for LCI1 transformants either (Ohnishi et al., 2010). The decreased rate of Ci-dependent photosynthesis and reduced affinity for Ci in the Cia8 mutant at pH 7.3 and 9.0 (FIGS. 5A-5C) provide evidence that CIA8 might be involved in Ci uptake.

While SBF transporters are often associated with co-transport of Na$^+$ ions as revealed in some animal proteins (Romero et al., 2013), results in this Example suggest that Na$^+$ ions may not necessarily be essential for the functionality of the CIA8 protein (FIG. 9). Low Na$^+$ ion concentrations (e.g. <10 µM to 100 mM) did not affect the growth of cells in the mutant and wildtype. This may be due to the TAP and MIN media in which the cell cultures are grown contain no added sodium. Thus, C. reinhardtii cells grow well with very low concentrations of sodium. While there is ample support for Nat-coupled transport in marine algae, H$^+$-coupled transport has been thought to play a role in freshwater algae. However, other ions such as Na+ or K+ might be coupled to the bicarbonate movement. Another possibility could involve an exchange (antiport) of bicarbonate for an anion such as chloride.

The analysis of the gene transcript in the mutant showed that the CIA8 mutant is a knockout. In the wildtype the Cia8 transcript was upregulated (4-fold) when high-CO$_2$ cells were acclimated to low CO$_2$ and this induction is consistent with the other transporters (FIGS. 3 and 11A-11B) although the level of induction is not as high as some of the CCM proteins. Regulation of transporters by transcript abundance in C. reinhardtii is well documented (Ohnishi et al., 2010; Gao et al., 2015; Yamano et al., 2015). This type of regulation arguably, prevents expression of HCO$_3^-$ transporters under high CO$_2$ conditions where they would not be required as the CCM is not functional. It was interesting that the relative expression of these other transporters is downregulated in the Cia8 mutant as compared to wildtype. This may be explained by negative feedback mechanism whereby the loss of the CIA8 protein leads to accumulation of HCO$_3^-$ in the cytosol which negatively impacts the two plasma membrane transporters (HLA3 and LCI1), and later NAR1.2. Alternatively, it may be that Cia8 gene may have some form of regulatory control over these other genes, just like the Nar1.2 gene transcript has recently been shown to regulate the expression of Hla3 (Yamano et al., 2015).

Several studies in the past have hypothesized the occurrence of a putative HCO$_3^-$ channel or transporter on the thylakoid membrane of algal CCM (Raven, 1997; Wang et al., 2011; Jungnick et al., 2014). In this study, the signal of the green fluorescent protein fused to CIA8 was evenly diffused throughout the chloroplast (FIG. 7). This localization throughout the organelle suggests that the protein may be on the thylakoid membrane, a strategic location to pump HCO$_3^-$ directly into the thylakoid lumen. At this point it is not clear whether CIA8 is a symporter or antiporter. However if it is on the thylakoid membrane it might transport an ion using the transmembrane H$^+$ gradient set up in the light. If CIA8 is on the thylakoid membrane, the NAR1.2 protein localized on the chloroplast envelope would not be able to make up for the loss of CIA8 and this is consistent with our results in this study. Also with this localization result, the Cia8 gene product would be making significant contribution to CCM function and perhaps, to Ci uptake.

Almost all SLC4-like proteins in plants, fungi and animals have this borate transport ability as the primitive function (Parker and Boron, 2013). The ubiquitous occurrence of SLC4-like proteins with borate transport function suggests that borate transport was the original function of these proteins such that bicarbonate and other ions would be a more recent acquisition (Parker and Boron, 2013). Basing on the phylogeny of the proteins and the binding mechanism, there is an interesting similarity of the borate and HCO$_3^-$ transport systems. Biophysical studies in cells of Chara carolina indicated that borate inhibited bicarbonate influx into cells i.e they compete for the same binding site (Lucas, 1975). Frommer and von Wiren, (2002) have provided a comparison of HCO$_3^-$ transport in the kidney with borate transport in the xylem to support this similarity. In addition, one study has shown that BOR1, the only characterized SLC protein in higher plants, transports boron in Arabidopsis (Takano et al., 2002). According to this study, BOR1 shares 27% identity with the yeast membrane protein YNL275w. Although the YNL275w protein is primarily a borate transporter, a study demonstrated in binding assays its ability to take up several anions as substrates, including HCO$_3^-$ (Zhao and Reithmeier, 2001). It is therefore interesting that the CIA8 protein shares identity with the yeast YNL275w protein suggesting a common origin and perhaps, similarity in physiological function. Analyses of these functional relationships could provide a better understanding of the role of SLC proteins in bicarbonate transport in C. reinhardtii.

In conclusion, the CIA8 protein is a transporter that plays a role in the C. reinhardtii CCM. When the gene is knocked out, the mutant shows a compromised Ci uptake and growth inhibition when grown on limiting CO$_2$ conditions. It was observed that the Cia8 gene encodes a putative bicarbonate transporter that is involved in direct uptake of HCO$_3^-$ into the thylakoid lumen for CO$_2$ fixation. The CIA8 protein is hydrophobic and according to prediction programs, has a topology comparable to other known transporters in the SBF/BASS subfamily.

Materials and Methods

Cell Culture and Growth

Chlamydomonas reinhardtii culture conditions were the same as described in Ma et al., (2011). The D66 strain (nit2$^-$, cw15, mt$^+$) was obtained from Dr Rogene Schnell (University of Arkansas, Little Rock) and the cc124 strain (nit1$^-$, nit2$^-$, m$^-$) was obtained from the C. reinhardtii Duke University Center (http://www.chlamy.org/). Tris-Acetate-Phosphate (TAP) and Minimal (MIN) media (without acetate) were prepared according to Sueoka (1960). Both TAP and MIN plates for the growth medium were prepared by adding about 1.2% (w/v) agar. Cell cultures were initiated by inoculating colonies from TAP plates into about 100 mL TAP liquid medium in Erlenmeyer flasks. Cultures were grown to early log phase on continuous illumination (about 100 µmol m$^{-2}$ s$^{-1}$) and shaking for about 48 hr. The TAP grown cultures were harvested and washed with MIN medium, and re-suspended in MIN media, connected to high CO$_2$ (about 5% [v/v] CO$_2$ in air) bubbling for about 48 hr to reach a cell density OD$_{730}$ between 0.2 and 0.3 (about 2-3×10$^8$ cells mL$^{-1}$). For CCM induction, the cells were transferred to low CO$_2$ (about 0.01% [v/v] CO$_2$ in air) bubbling for 4 hr.

Mutagenesis, Isolation of Sick-On-Low CO$_2$ Mutants, Phenotypic Screen

Mutants were generated in a mutagenesis screen according to Jungnick et al., (2014). A linear plasmid (pSL18) bearing the AphVIII gene conferring paromomycin resistance (para$^R$) was transformed into the D66 strain of C. reinhardtii by electroporation (Shimogawara et al., 1998). Transformed cells were selected on TAP plates containing the antibiotic paromomycin (about 7.5 µg mL$^{-1}$; Invitrogen). Antibiotic resistant strains were screened for growth in a high CO$_2$ chamber (about 5% [v/v]) CO$_2$ in air and a low CO$_2$ chamber (about 0.01% [v/v] CO$_2$ in air) with the same light conditions as mentioned above. Cells were streaked on MIN plates and placed in growth chambers. Spot tests were done by suspending actively growing cells in liquid MIN medium to the same cell densities (OD$_{730}$=0.15, 0.07 and 0.03) and spotting about 15 μl of each suspension onto MIN plates. These were placed in high, ambient and low $CO_2$ chambers for 7 d. $CO_2$ concentration in the growth chambers was measured using an Environmental Gas Monitor (EGM-4, PP systems, Massachusetts).

Identification of Flanking Region

An adaptor-mediated PCR method was used to identify the DNA region flanking the AphVIII insertion (Pollock et al., 2016). Homology searches were done using the Joint Genome Institute *C. reinhardtii* in the Phytozome database version 10.3 (Merchant et al., 2007; Blaby et al., 2014).

Linkage Analysis

Genetic crosses and tetrad analysis were done as described previously (Moroney et al., 1986; Harris, 2009). Briefly, Cia8 ($mt^+$) and cc124 ($mt^-$) cell cultures in log phase were transferred to nitrogen deficient TAP medium in the light, overnight to induce gametogenesis. The next morning about 3 mL of each culture were mixed to allow mating for about 3 hr in the light. Aliquots (about 0.5 mL) were plated on TAP minus-Nitrogen medium containing about 4% agar. The plates were stored in the dark for two weeks to allow zygote maturation. After about 14 days, zygotes were transferred to about 1.2% agar TAP medium plates for meiotic germination. Tetrad dissections were conducted and linkage determined by association of the paromomycin resistance gene with progeny that did not grow well on low $CO_2$.

Photosynthetic Assays

*C. reinhardtii* cultures were started heterotrophically in about 100 mL of TAP medium for 48 hr to reach log phase. The cells were centrifuged and transferred to 250 mL Erlenmeyer flasks and re-suspended in MIN medium, bubbled with about 5% $CO_2$ until they reached a cell density $OD_{730}=0.2$-$0.3$ (about $3\times10^6$ cells $mL^{-1}$). The cultures were then transferred to low $CO_2$ (about 0.01%) for about 4 hr to allow CCM induction. The affinity for external Ci ($K_{0.5}$ [DIC]) (dissolved inorganic carbon) was estimated according to Ma et al., (2011). In the method, cells with an equivalent of about 100 μg of chlorophyll were suspended in about 25 mM HEPES-KOH buffer (pH about 7.3) or about 25 mM CHES-KOH buffer (pH about 9.0) bubbled with inert nitrogen gas i.e. $CO_2$ free. The cells were transferred to an $O_2$ electrode chamber (Rank Brothers, Cambridge UK) illuminated at about 300 μmol $m^{-2}s^{-1}$, and left to deplete any remaining DIC in the buffer and intracellular spaces. Upon depletion of endogenous $CO_2$, no net $O_2$ evolution was observed. Known concentrations of $NaHCO_3$ were injected into the chamber and the rate of $O_2$ evolution was measured. The $K_{0.5}$[DIC] was calculated as the DIC concentration required for half maximal rates of oxygen evolution (Badger, 1985). Chlorophyll content was measured by combining chlorophyll a and b. Chlorophyll was extracted in 100% methanol and measured using the spectrophotometer. The $K_{0.5}$ ($CO_2$) is taken as the $CO_2$ concentration needed to reach half $V_{max}$ $O_2$ evolution.

Intracellular Localization

The whole Cre09.395700 gene (4,846 bp) was amplified and introduced into a modified pSL18CrGFP vector using EcoR1 and NdeI restriction sites. The Cre09.395700 gene was inserted such that it was in frame with *Chlamydomonas* codon optimized GFP gene (Fuhrmann et al., 1999) already in the vector. The vector was linearized with KpnI digestion. Transformation of the wildtype strain D66 with the Cia8 gene fragment was achieved by electroporation with the linearized vector and paromomycin resistant colonies were analyzed using PCR. For imaging GFP-tagged proteins, about 5 μL of cells were mounted onto a slide with about 1.5% low melting point agarose. Cells were imaged using a Leica Sp2 confocal microscope. The Kr/Ar laser was set at wavelength of about 488 nm to excite both eGFP and chlorophyll, with the photomultiplier tube set to about 500-520 nm to detect eGFP fluorescence and about 660-700 nm to detect chlorophyll autofluorescence. A 20× lens was used to image the cells.

Gene Expression Analysis

RNA extraction was done using Triazol reagent following the guidelines provided (Invitrogen). About 1 μg of total RNA was used as template for synthesis of cDNA. Superscript First Strand Synthesis System for transcripts with high GC content (Invitrogen, Carlsbad, Calif.) was used to synthesize cDNA according to manufacturer's instructions. An aliquot of about 100 ng cDNA was used as the template with SYBR Select (Applied Biosystems, Foster City, Calif.) for quantitative PCR in an ABI Prism 7000 sequence detection system following the manufacturer's instructions (Applied Biosystems, Foster City, Calif.). Normalized primers were specific for the GAPDH gene for RT-PCR. For q-RTPCR the CBLP gene was used as a control in these experiments (Mus et al., 2007). The primers used for the respective cDNAs are listed in Table 2.

Complementation of CIA8

Complementation of the Cia8 mutant was achieved by transformation of Cia8 cells with a construct containing a wildtype copy of the Cia8 gene. The construct consisted of the Cia8 CDS fragment including the 5' UTR and 3'UTR regions (2,949 bp) and a 1,080 bp fragment of promoter region. These fragments were ligated using the Not1 restriction site, which was then ligated into pGEM-T. The sequenced fragment was cloned into the shuttle vector pSP124s using BamHI and SacI restriction sites. Sequences were obtained from Phytozome Version 10.2 (phytozome.jgi.doe.gov/pz/portal/html). Primers used to amplify the Cia8 genomic fragment are shown in Table 2. The electroporation method was used for cell transformation and strains were selected for bleomycin resistance (Shimogawara et al., 1998). The presence of complemented DNA in selected *Chlamydomonas* strains was confirmed by using PCR.

Ci Uptake Assay

Active species uptake of $H^{14}CO_3$ was carried out at pH about 9.0 (about 25° C.) with about 15 sec uptake periods terminated by silicone oil centrifugation-filtration (Price et al., 2004). $KHCO_3$ aliquots were added from about 25 mM stock (pH about 9.5). The rate of $CO_2$ supply from $HCO_3^-$ at pH about 9.0 was calculated by applying an experimentally determined rate constant. Table 1 demonstrates the maximal oxygen evolution activity ($V_{max}$) and Ci affinity, $K_{(0.5)}$ values for wildtype D66 and Cia8 mutant cells. Cells were grown on high $CO_2$ for 48 hr and acclimated to low $CO_2$ for 4 hr. In parenthesis: ±SE; n=3.

TABLE 1

| | Vmax (μmol $O_2$ $mgChl^{-1}$ $hr^{-1}$) | | $K_{(0.5)}$ Ci (μM) | |
|---|---|---|---|---|
| | D66 | CIA8 | D66 | CIA8 |
| pH 7.3 | | | | |
| High $CO_2$ cells | 166 (±3.3) | 155 (±4.5) | 95 (±2.8) | 158 (±2.9) |
| Low $CO_2$ cells | 160 (±7.8) | 150 (±5.3) | 20 (±2.7) | 60 (±4.7) |
| pH 9.0 | | | | |
| Low $CO_2$ cells | 92.7 (±1.5) | 90 (±5.2) | 110 (±5.0) | 320 (±10.5) |

TABLE 2

Sequences of primers used in this study

| Primer name | Sequence 5' to 3' end | SEQ ID NO: |
|---|---|---|
| For confirmation of insert | | |
| CIA8-F | GCACATACTATTGAGGTGCCG | 5 |
| CIA8-R | CGGCTGTGTTCAGTCACCT | 6 |
| RIM3-1 | CGGTATCGGAGGAAAAGCTG | 7 |
| RIM3-2 | TACCGGCTGTTGGACGAGTTCTTCTG | 8 |
| RX1 | GCCCTCATAGCCCGCCAAATCAG | 9 |
| RX2 | AAGCCGATAAACACCAGCCC | 10 |
| For RT-PCR | | |
| CIA8CDSF2 | CAGTACCAACAGCAGCATAG | 11 |
| Cre09.g395700_CIA8-F2 | ATGTGCGCCGGCATTCG | 12 |
| Cre09.g395700_CIA8-R2 | CTAGGCCGCCTTGTTGGC | 13 |
| ACTIN F | GCCAGAAGGACTCGTACGTT | 14 |
| ACTIN R | CGCCAGAGTCCAGCACGATA | 15 |
| GAPDH F | ATGGCGCCAAAGAAGGTTCTTC | 16 |
| GAPDH R | CTACATCTTGGCCGCCACGATC | 17 |
| For construction of localization plasmids | | |
| CIA8CDSEcoRIRnostop | GATCGAATTCACGGCCGCCTTGTTGGCTTTG | 18 |
| CIA8CDSNdelF | CATGACCATATGATGTGCGCCGGCATTCGGTC | 19 |
| ShortGFP-F | CCAAGGGCGAGGAGCT | 20 |
| CrGFP-R | CTTGTACAGCTCGTCCATG | 21 |
| For construction of complementation plasmids | | |
| CIA8transcr_R_BamHI | TAGGATCCCTTTCATAGGTTCGTGCCTCC | 22 |
| CIA8prom_F_SacI | CAGAGCTCCTCAGGCAAGGTGATCAAGTG | 23 |
| CIA8prom_R_NotI | ACTAGCGGCCGCGTCCGCATGTTGCTTATTTC | 24 |
| CIA8transcr_F_NotI | ACTAGCGGCCGCGTATACATGATAGCACGCCTTG | 25 |
| For quantitative Real time PCR | | |
| HLA3_4,765F | GAGCGTTGTGTGCACTGTTC | 26 |
| HLA3_4,884R | TCTCTCTGCGGCTACATCCT | 27 |
| Nar1.2_1,736F | AGTTGAGGCAGGTTGAGAGC | 28 |
| Nar1.2_1,855R | CCCTGACCAGTTGTTGCCAT | 29 |
| LCI1_1,125F | TGGTTTACTGGCCGCTTCTG | 30 |
| LCI1_1,244R | TCACACAGCCAATCGAGGTT | 31 |
| CIA8_1,745F | CTGGAGTGAGGGGCATATG | 32 |
| CIA8_1,867R | TTCATAGGTTCGTGCCTCC | 33 |
| SLC_cre09.g393250_1,874F | CGTTACTCCCGTACTCGTACC | 34 |
| SLC_cre09.g393250_1,993R | GCCCACCGAACTACAGAGAG | 35 |

TABLE 2-continued

Sequences of primers used in this study

| Primer name | Sequence 5' to 3' end | SEQ ID NO: |
|---|---|---|
| SLC_cre02.g147450_2,777F | ATAGGCGGCAGGGAAAACTC | 36 |
| SLC_cre02.g147450_2,896R | TTTGTGGAATCCGCGTGACA | 37 |
| CBLPF | 5'-CTTCTCGCCCATGACCAC-3' | 38 |
| CBLPR | 5'-CCCACCAGGTTGTTCTTCAG-3' | 39 |

REFERENCES FOR EXAMPLE 1

Amoroso G, Sültemeyer D, Thyssen C, Fock H P (1998) Uptake of HCO3– and CO2 in cells and chloroplasts from the microalgae *Chlamydomonas reinhardtii* and *Dunaliella tertiolecta*. 116

Atkinson N, Feike D, Mackinder L C, Meyer M T, Griffiths H, Jonikas M C, Smith A M, McCormick A J (2015) Introducing an algal carbon-concentrating mechanism into higher plants: location and incorporation of key components. Plant Biotechnol J 5: 12497

Badger M R (1985) Photosynthetic oxygen exchange. Ann Rev of Plant Physiol 36: 27-53

Badger M R, Palmqvist K, Yu J-W (1994) Measurement of CO2 and HCO3– fluxes in cyanobacteria and microalgae during steady-state photosynthesis. Physiologia Plant 90: 529-536

Blaby I K, et al., (2014) The *Chlamydomonas* genome project: a decade on. Trends Plant Sci 19: 672-680

Borkhsenious O N, Mason C B, Moroney J V (1998) The intracellular localization of Ribulose-1,5-Bisphosphate Carboxylase/Oxygenase in *Chlamydomonas reinhardtii*. Plant Physiol 116: 1585-1591

Duanmu D, Miller A R, Horken K M, Weeks D P, Spalding M H (2009) Knockdown of limiting-CO2-induced gene HLA3 decreases HCO3– transport and photosynthetic Ci affinity in *Chlamydomonas reinhardtii*. Proc Natl Acad Sci USA 106: 5990-5995

Engel B D, Schaffer M, Kuhn Cuellar L, Villa E, Plitzko J M, Baumeister W (2015) Native architecture of the *Chlamydomonas* chloroplast revealed by in situ cryo-electron tomography. Elife 13: 04889

Fischer N, Rochaix J D (2001) The flanking regions of PsaD drive efficient gene expression in the nucleus of the green alga *Chlamydomonas reinhardtii*. Mol Genet Genomics 265: 888-894

Frommer W B, von Wiren N (2002) Plant biology: Ping-pong with boron. Nature 420: 282-283

Fuhrmann M, Oertel W, Hegemann P (1999) A synthetic gene coding for the green fluorescent protein (GFP) is a versatile reporter in *Chlamydomonas reinhardtii*. Plant 19: 353-361

Furumoto T, Yamaguchi T, Ohshima-Ichie Y, et al. 2011. A plastidial sodium-dependent pyruvate transporter. Nature 476, 472-475.

Gao H, Wang Y, Fei X, Wright D A, Spalding M H (2015) Expression activation and functional analysis of HLA3, a putative inorganic carbon transporter in *Chlamydomonas reinhardtii*. Plant 82: 1-11

Gigolashvili T., et al. 2009. The plastidic bile acid transporter 5 is required for the biosynthesis of methionine-derived glucosinolates in *Arabidopsis thaliana*. The Plant Cell 21, 1813-1829.

Giordano M, Beardall J, Raven J A (2005) CO2 concentrating mechanisms in algae: Mechanisms, environmental modulation, and evolution. Ann Rev Plant Bio 56: 99-131

Gutknecht J, Bisson M A, Tosteson F C (1977) Diffusion of carbon dioxide through lipid bilayer membranes. Effects of carbonic anhydrase, bicarbonate, and unstirred layers. J. Gen. Physiol 69: 779-794

Harris E H S, D. B.; Witman, G., ed (2009) The *Chlamydomonas* Sourcebook, Vol Ed 2. Academic Press, Amsterdam Im C S, Grossman A R (2002) Identification and regulation of high light-induced genes in *Chlamydomonas reinhardtii*. Plant 30: 301-313

Jungnick N, Ma Y, Mukherjee B, Cronan J C, Speed D J, Laborde S M, Longstreth D J, Moroney J V (2014) The carbon concentrating mechanism in *Chlamydomonas reinhardtii*: finding the missing pieces. Photosynth Res 121: 159-173

Kelley L A, Mezulis S, Yates C M, Wass M N, Sternberg M J E (2015) The Phyre2 web portal for protein modeling, prediction and analysis. Nat Protocols 10: 845-858

Kuchitsu K, Tsuzuki M, Miyachi S (1988) Changes of starch localization within the chloroplast induced by changes in CO2 concentration during growth of *Chlamydomonas reinhardtii*: Independent regulation of pyrenoid starch and stroma starch. Plant Cell Phys 29: 1269-1278

Lucas W J (1975) Photosynthetic Fixation of 14Carbon by internodal cells of *Chara corallina*. Exp Bot 26: 331-346

Ma Y, Pollock S V, Xiao Y, Cunnusamy K, Moroney J V (2011) Identification of a novel gene, CIA6, required for normal pyrenoid formation in *Chlamydomonas reinhardtii*. Plant Physiol 156: 884-896

Mariscal V, Moulin P, Orsel M, Miller A J, Fernandez E, Galvan A (2006) Differential regulation of the *Chlamydomonas* Nar1 gene family by carbon and nitrogen. Protist 157: 421-433

Merchant S S, et al. (2007) The *Chlamydomonas* genome reveals the evolution of key animal and plant functions. Science 318: 245-250

Mitra M, Mason C B, Xiao Y, Ynalvez R A, Lato S M, Moroney J V (2005) The carbonic anhydrase gene families of *Chlamydomonas reinhardtii*. Can J Bot 83: 780-795

Moroney J, Tolbert N E, Sears B (1986) Complementation analysis of the inorganic carbon concentrating mechanism of *Chlamydomonas reinhardtii*. Mol Gen Gen 204: 199-203

Moroney J V, Kitayama M, Togasaki R K, Tolbert N E (1987) Evidence for inorganic carbon transport by intact chloroplasts of *Chlamydomonas reinhardtii*. Plant Physiol 83: 460-463

Moroney J V, Ma Y, Frey W D, Fusilier K A, Pham T T, Simms T A, DiMario R J, Yang J, Mukherjee B (2011) The carbonic anhydrase isoforms of *Chlamydomonas reinhardtii*: intracellular location, expression, and physiological roles. Photosynth Res 109: 133-149

Moroney J V, Ynalvez R A (2007) Proposed Carbon Dioxide Concentrating Mechanism in *Chlamydomonas reinhardtii*. Eukaryotic Cell 6: 1251-1259

Morth J P, Pedersen B P, Buch-Pedersen M J, Andersen J P, Vilsen B, Palmgren M G, Nissen P (2011) A structural overview of the plasma membrane Na+,K+-ATPase and H+-ATPase ion pumps. Nat Rev Mol Cell Biol 12: 60-70

Mus F, Dubini A, Seibert M, Posewitz M C, Grossman A R (2007) Anaerobic acclimation in *Chlamydomonas reinhardtii*: Anoxic gene expression, hydrogenase induction, and metabolic pathways. J Biol Chem 282: 25475-25486

Nakajima K, Tanaka A, Matsuda Y (2013) SLC4 family transporters in a marine diatom directly pump bicarbonate from seawater. Proc Natl Acad Sci USA 110: 1767-1772

Ohnishi N, Mukherjee B, Tsujikawa T, Yanase M, Nakano H, Moroney J V, Fukuzawa H (2010) Expression of a low CO2-inducible protein, LCI1, increases inorganic carbon uptake in the green alga *Chlamydomonas reinhardtii*. Plant Cell 22: 3105-3117

Parker M D, Boron W F (2013) The Divergence, Actions, Roles, and Relatives of Sodium-Coupled Bicarbonate Transporters. Physiol Rev 93: 803-959

Pootakham W, Gonzalez-Ballester D, Grossman A R (2010) Identification and regulation of plasma membrane sulfate transporters in *Chlamydomonas*. Plant Physiol 153: 1653-1668

Price G D, Howitt S M (2011) The cyanobacterial bicarbonate transporter BicA: its physiological role and the implications of structural similarities with human SLC26 transporters. Biochem Cell Biol 89: 178-188

Price G D, Woodger F J, Badger M R, Howitt S M, Tucker L (2004) Identification of a SulP-type bicarbonate transporter in marine cyanobacteria. Proc Natl Acad Sci USA 101: 18228-18233

Pushkin A, Kurtz I (2006) SLC4 base (HCO3-, CO3 2-) transporters: classification, function, structure, genetic diseases, and knockout models. Am J Physiol Renal Physiol 290: F580-599

Raven J (1997) Putting the C in phycology. Euro J Phycology 32: 319-333

Rawat M, Henk M C, Lavigne L L, Moroney J V (1996) *Chlamydomonas reinhardtii* mutants without ribulose-1,5-bisphosphate carboxylase-oxygenase lack a detectable pyrenoid. Planta 198: 263-270

Romero M F (2005) Molecular pathophysiology of SLC4 bicarbonate transporters. Curr Opin Nephrol Hypertens 14: 495-501

Romero M F, Chen A P, Parker M D, Boron W F (2013) The SLC4 family of bicarbonate (HCO3-) transporters. Mol Aspects Med 34: 159-182

Shimogawara K, Fujiwara S, Grossman A, Usuda H (1998) High-efficiency transformation of *Chlamydomonas reinhardtii* by electroporation. Genetics 148: 1821-1828

Sizova I, Fuhrmann M, Hegemann P (2001) A *Streptomyces rimosus* aphVIII gene coding for a new type phosphotransferase provides stable antibiotic resistance to *Chlamydomonas reinhardtii*. Gene 277: 221-229

Sueoka N (1960) Mitotic replication of de-oxyribonucleic acid in *Chlamydomonas reinhardi*. Proc Nat Acad Sci USA 46: 83-91

Sültemeyer D, Klöck G, Kreuzberg K, Fock H (1988) Photosynthesis and apparent affinity for dissolved inorganic carbon by cells and chloroplasts of *Chlamydomonas reinhardtii* grown at high and low CO2 concentrations. Planta 176: 256-260

Takano J, Noguchi K, Yasumori M, Kobayashi M, Gajdos Z, Miwa K, Hayashi H, Yoneyama T, Fujiwara T (2002) *Arabidopsis* boron transporter for xylem loading. Nature 420: 337-340

Taylor A R, Brownlee C, Wheeler G L (2012) Proton channels in algae: reasons to be excited. Trends Plant Sci 17: 675-684

Wang Y, Duanmu D, Spalding M H (2011) Carbon dioxide concentrating mechanism in *Chlamydomonas reinhardtii*: inorganic carbon transport and CO2 recapture. Photosynth Res 109: 115-122

Wang Y, Spalding M H (2014) Acclimation to very low CO2: Contribution of limiting CO2 inducible proteins, LCIB and LCIA, to inorganic carbon uptake in *Chlamydomonas reinhardtii*. Plant Physiol 166: 2040-2050

Yamano T, Sato E, Iguchi H, Fukuda Y, Fukuzawa H (2015) Characterization of cooperative bicarbonate uptake into chloroplast stroma in the green alga *Chlamydomonas reinhardtii*. Proc Natl Acad Sci USA 112: 7315-7320

Yamano T, Tsujikawa T, Hatano K, Ozawa S, Takahashi Y, Fukuzawa H (2010) Light and low-CO2-dependent LCIB-LCIC complex localization in the chloroplast supports the carbon-concentrating mechanism in *Chlamydomonas reinhardtii*. Plant Cell Physiol 51: 1453-1468

Zhao R, Reithmeier R A F (2001) Expression and characterization of the anion transporter homologue YNL275w in *Saccharomyces cerevisiae*. Am J Physiol Cell Physiol 281: C33-C45

---

We claim:

1. A transgenic plant comprising a recombinant polynucleotide that comprises a cDNA molecule encoding a green alga Cia8 polypeptide having at least 95% sequence identity to SEQ ID NO: 4 and at least one regulatory sequence operatively linked to the cDNA molecule such that the green alga Cia8 polypeptide is expressed in the plant cell, wherein the transgenic plant has improved growth in low $CO_2$ conditions.

2. A method for increasing growth of a plant in low $CO_2$ conditions relative to a wild type plant, the method comprising:

integrating into the genome of at least one cell of the plant a cDNA molecule encoding a green alga Cia8 polypeptide having at least 95% sequence identity to SEQ ID NO: 4 and at least one regulatory sequence operatively linked to the cDNA molecule such that the green alga Cia8 polypeptide is expressed in the plant cell.

3. The transgenic plant of claim 1, wherein the green alga Cia8 protein has at least 99% sequence identity to any one of SEQ ID NO: 4.

4. The transgenic plant of claim 1, wherein the green alga Cia8 protein has 100% sequence identity to any one of SEQ. ID NO: 4.

* * * * *